(12) United States Patent
Vigneault et al.

(10) Patent No.: US 11,572,403 B2
(45) Date of Patent: Feb. 7, 2023

(54) BROADLY NEUTRALIZING ANTI-HIV-1 ANTIBODIES THAT BIND TO AN N-GLYCAN EPITOPE ON THE ENVELOPE

(71) Applicant: AbVitro LLC, Seattle, WA (US)

(72) Inventors: Francois Vigneault, Yarrow Point, WA (US); Adrian Wrangham Briggs, Seattle, WA (US); Stephen J. Goldfless, Seattle, WA (US); Sonia Timberlake, Brookline, MA (US)

(73) Assignee: ABVITRO LLC, Seattle, WA (US)

( * ) Notice: Subject to any disclaimer, the term of this patent is extended or adjusted under 35 U.S.C. 154(b) by 34 days.

(21) Appl. No.: 17/010,755

(22) Filed: Sep. 2, 2020

(65) Prior Publication Data

US 2021/0101963 A1    Apr. 8, 2021

Related U.S. Application Data

(62) Division of application No. 15/762,442, filed as application No. PCT/US2016/053599 on Sep. 24, 2016, now Pat. No. 11,142,565.

(60) Provisional application No. 62/232,279, filed on Sep. 24, 2015.

(51) Int. Cl.
| | |
|---|---|
| *C07K 16/10* | (2006.01) |
| *A61K 39/42* | (2006.01) |
| *A61K 39/395* | (2006.01) |
| *A61P 31/18* | (2006.01) |
| *C07K 16/46* | (2006.01) |
| *C12N 15/113* | (2010.01) |
| *A61K 39/00* | (2006.01) |
| *A61K 47/68* | (2017.01) |

(52) U.S. Cl.
CPC ........ *C07K 16/1063* (2013.01); *A61K 39/395* (2013.01); *A61K 39/42* (2013.01); *A61P 31/18* (2018.01); *C07K 16/46* (2013.01); *C12N 15/1132* (2013.01); *A61K 47/6803* (2017.08); *A61K 2039/505* (2013.01); *A61K 2039/5158* (2013.01); *C07K 2317/21* (2013.01); *C07K 2317/33* (2013.01); *C07K 2317/55* (2013.01); *C07K 2317/56* (2013.01); *C07K 2317/565* (2013.01); *C07K 2317/622* (2013.01); *C07K 2317/76* (2013.01); *C07K 2317/92* (2013.01); *C07K 2319/03* (2013.01); *C07K 2319/33* (2013.01); *C07K 2319/70* (2013.01); *C12N 2740/16023* (2013.01); *C12N 2740/16051* (2013.01); *C12N 2740/16111* (2013.01)

(58) Field of Classification Search
CPC ................................................. C07K 16/1063
See application file for complete search history.

(56) References Cited

U.S. PATENT DOCUMENTS

| | | | |
|---|---|---|---|
| 2013/0274117 A1 | 10/2013 | Church et al. | |
| 2013/0296535 A1 | 11/2013 | Church et al. | |
| 2014/0357500 A1 | 12/2014 | Vigneault et al. | |
| 2016/0244825 A1 | 8/2016 | Vigneault et al. | |
| 2017/0268056 A1 | 9/2017 | Vigneault et al. | |
| 2018/0274021 A1 | 9/2018 | Vigneault et al. | |
| 2019/0024145 A1 | 1/2019 | Vigneault et al. | |
| 2019/0025299 A1 | 1/2019 | Vigneault et al. | |

FOREIGN PATENT DOCUMENTS

| | | |
|---|---|---|
| WO | WO 2010/107939 A2 | 9/2010 |
| WO | WO 2012/030904 A2 | 3/2012 |
| WO | WO 2013/055908 A1 | 4/2013 |
| WO | WO 2014/063059 A1 | 4/2014 |
| WO | WO 2014/184143 A1 | 11/2014 |
| WO | WO 2015/077789 A2 | 5/2015 |

OTHER PUBLICATIONS

Pashov, A., et al., 2007, Defining carbohydrate antigens as HIV vaccine candidates, Curr. Pharm. Design 13:185-201.*
Go, E. P., et al., 2008, Glycosylation site-specific analysis of HIV envelope proteins (JR-FL and CON-S) reveals major differences in glycosylation site occupancy, glycoform profiles, and antigenic epitopes' accessibility, J. Proteome Res. 7:1660-1674.*
Xiang, J., et al., 1999, Light-chain framework region residue Tyr71 of chimeric B72.3 antibody plays an important role in influencing theTAG72 antigen binding, Prot. Engineer. 12(5):417-421.*
Liu, Z., 1999, Fine mapping of the antigen-antibody interaction of scFv215, a recombinant antibody inhibiting RNA polymerase II from *Drosophila melanogaster*, J. Mol. Recog. 12:103-111.*
Dimitrov et al., "A Cryptic Polyreactive Antibody Recognizes Distinct Clades of HIV-1 Glycoprotein 120 by an Identical Binding Mechanism," *Journal of Biological Chemistry*, vol. 289, No. 25, 2014 (13 pages).
Franchini, G., and M. L. Bosch, 1989, Genetic relatedness of the human immunodeficiency viruses type 1 and 2 (HIV-1, HIV-2) and the simian immunodeficiency virus (SIV), Ann. NY Acad. Sci. 554(1):81-87.
Horiya et al., "Directed Evolution of Multivalent Glycopeptides Tightly Recognized by HIV Antibody 2G12," *Journal of The American Chemical Society*, vol. 136, No. 14, 2014 (9 pages).
International Search Report and Written Opinion issued for Application No. PCT/US2016/053599, dated Jan. 3, 2017 (29 pages).
Krumm et al., "Mechanisms of escape from the PGT128 family of anti-HIV broadly neutralizing antibodies," *Retrovirology*, vol. 13, No. 1, 2016 (15 pages).
Liu, Z., et al., 1999, Fine mapping of the antigen-anti body interaction of scFv215, a recombinant antibody inhibiting RNA polymerase II from *Drosophila melanogaster*, J. Mol. Recog. 12:103-111.

(Continued)

*Primary Examiner* — Jeffrey S Parkin
(74) *Attorney, Agent, or Firm* — Finnegan, Henderson, Farabow, Garrett & Dunner, LLP

(57) ABSTRACT

This invention relates to novel anti-HIV antibodies that can be used in the treatment and detection of human immunodeficiency virus (HIV). These antibodies exhibit a high degree of sensitivity and can provide a broad range of specificity.

23 Claims, 8 Drawing Sheets

Specification includes a Sequence Listing.

(56) References Cited

OTHER PUBLICATIONS

Mouquet et al., "Complex-type N-glycan recognition by potent broadly neutralizing HIV antibodies" Proc Natl Acad Sci U.S.A. 109(47): E3268-E3277 (2012).
Pashov, A., et al., 2007, Defining carbohydrate antigens as HIV vaccine candidates, Curr. Pharm. Des. 13:185-201.
Search Report and Written Opinion issued by the Intellectual Property Office of Singapore for Singapore Patent Application No. 11201802255P, dated May 17, 2019 (11 pages).
Sok et al., "A Prominent Site of Antibody Vulnerability on HIV Envelope Incorporates a Motif Associated with CCR5 Binding and Its Camouflaging Glycans," *Immunity*, vol. 45, No. 1, 2016 (16 pages).
Walker et al., "Broad neutralization coverage of HIV by multiple highly potent antibodies," *Nature*, vol. 477, No. 7365, 2011 (14 pages).
Xiang, J., et al., 1999, Light-chain framework region residue Tyr71 of chimeric B72.3 antibody plays an important role in influencing the TAG72 antigen binding, Prat. Engin. 12(5):417-421.
Yasmeen et al., "Differential binding of neutralizing and non-neutralizing antibodies to native-like soluble HIV-1 Env trimers, uncleaved Env proteins, and monomeric subunits," *Retrovirology*, vol. 11, No. 1, 2014 (17 pages).
Yasmeen et al. "Differential binding of neutralizing and non-neutralizing antibodies to native-like soluble HIV-1 Env trimers, uncleaved Env proteins, and monomeric subunits—Supplementary Data: Tables S2-S6," *Retrovirology*, vol. 11, No. 1, 2014 (5 pages).
Barouch et al. Therapeutic efficacy of potent neutralizing HIV-1-specific monoclonal antibodies in SHIV-infected rhesus monkeys, Nature, 2013, vol. 503, pp. 224-228.
GenBank Accession No. PDB: 4JY4_B, dated Feb. 5, 2014, 3 pages.
GenBank Accession No. PDB: 4JY4_A, dated Feb. 5, 2014, 3 pages.
GenBank Accession No. AEN14391.1, dated Sep. 26, 2011, 2 pages.
GenBank Accession No. AEN14409.1, dated Sep. 26, 2011, 2 pages.
Julien et al. Broadly Neutralizing Antibody PGT121 Allosterically Modulates CD4 Binding via Recognition of the HIV-1 gp120 V3 Base and Multiple Surrounding Glycans, PLoS Pathog, 2013, vol. 9, N.5, e1003342.
Sahu et al. Anti-HIV designer T cells progressively eradicate a latently infected cell line by sequentially inducing HIV reactivation then killing the newly gp120-positive cells, Virology, 2013, vol. 446, pp. 268-275.
Sok et al. The Effects of Somatic Hypermutation on Neutralization and Binding in the PGT121 Family of Broadly Neutralizing HIV Antibodies, PLOS Pathogens, 2013, vol. 9, Issue 11, e1003754.

* cited by examiner

```
SEQ ID NO: 69   1  QVQLQESGPGLVKPSETLSLTCTVSGGSISSYYWSWIRQPPGKGLEWIGYIYYSGSTNYNPSLKSRVTISVDTSKNQFSL 80
SEQ ID NO:  1   1  QMQLQESGPGLIVKPSETLSLTCVVSGGSVSGNIWSWIRQSPGKGPEWVGFVSGEY-IEYNPSLKSRLTISRDTSKNQLSL 79
SEQ ID NO:  3   1  QVQLQESGPGLVKPSETLSLTCSVSGDSMNNYYWTWIRQSPGKGLEWIGYVSDRASATYNPSLKSRVISRDTSKNQLSL 80
SEQ ID NO:  5   1  QLQLQESGPGLVKPPETLSLTCSVSGASINDAYWSWIRQSPGKRPEWVGYVHHSGDTNYNPSLKRRVTFSLDTAKNEVSL 80
SEQ ID NO:  7   1  QLQLQESGPGLVKPPETLSLTCSVSGASINDAYWSWIRQSPGKRPEWVGYVHHSGDTNYNPSLKRRVTFSLDTAKNEVSL 80
SEQ ID NO:  9   1  QVHLQESGPGLVKPSETLSLTCNVSGTLVRDNYWSWIRQPLGKQPEWIGYVHDSGDTNYNPSLKSRVHLSLDKSKNLVSL 80
SEQ ID NO: 11   1  QVHLQESGPGLVKPSETLSLTCNVSGTLVRDNYWSWIRQPLGKQPEWIGYVHDSGDTNYNPSLKSRVHLSLDKSKNLVSL 80
SEQ ID NO: 13   1  QMQLQESGPGLVKPSETLSLTCSVSGASISDSYWSWFRRSPGKGLEWIGYVHKSGDTNYSPSLKSRVNLSLDASKNQVSL 80
SEQ ID NO: 15   1  QVHLQESGPGLVKPSETLSLTCVVSGASTSGQYWSWIRQSPGKGLEWIGYRSDSGDANYNPSLKSRVIISLDTSRNQLSL 80
SEQ ID NO: 16   1  QVQLQESGPGLVKPSETLSVTCSVSGDSMNNYYWTWIRQSPGKGLEWIGYISDRASATYNPSLNSRVVISRDTSKNQLSL 80

SEQ ID NO: 69  81  KLSSVTAADTAVYYCARTQQGKRIYGVVSFGDYYYYYMDVWGKGTTVTVSS 132
SEQ ID NO:  1  80  TLRSVTAADTAMYYCAKTLRARRIYGVIAFGEVYDYHYFDVWGKGTMVTVSS 131
SEQ ID NO:  3  81  KLNSVTLADTAVYYCATARRGQRIYGEVAFGEFFYYSMDVWGKGTAVTVSS 132
SEQ ID NO:  5  81  KLIVALTAADSAVYFCARALHGKRIYGTVALGELFVYFHMDVWGKGTAVTVSS 132
SEQ ID NO:  7  81  KLIVALTAADSAVYFCARALHGKRIYGTVALGELFVYFYMDVWGKGTAVTVSS 132
SEQ ID NO:  9  81  RLTGVTAADSAIYYCATTKHGRRIYGVVAFKEWFTYFYMDVWGKGTSVTVSS 132
SEQ ID NO: 11  81  RLTGVTAADSAIYYCATTKHGRRIYGVVAFKEWFTYFYMDVWGKGTSVTVSS 132
SEQ ID NO: 13  81  SIVAATAADSGKYYCARTLHGRRIYGIVAFNEWFTYFYMDVWGNGTQVTVSS 132
SEQ ID NO: 15  81  NVTSVTTADTAMYFCARAQRGKRIYGVVSLGEYHYYIMDVWGTGTPVTVSS 132
SEQ ID NO: 16  81  KLNSVTPADTAVYYCATARRGQRIYGEVSFGEFFYYSMDVWGKGTAVTVSS 132
```

FIG. 6A

```
SEQ ID NO: 70    1 ---SYVLTQppS-VSVAPGQTARITCGGNNIGSKSVHWYQQKPGQAPVLVVYDDSDRPSGIPERFSGS----NSGNTATLTI  74
SEQ ID NO:  2    1 ---TDSVASDV-AMSVAPGDTATISCGEKSNGARAVQWYQQKPGQAPVLLIYNNQDRPSGIPERFSASPDAGFGTTATLTI  77
SEQ ID NO:  4    1 -----GSVTSFVrPLSVALGETASISCGRQALGSRAVQWYQHRPGQAPVLLIYNNQDRPSGIPERFSGTPDINFGTRATLTI  77
SEQ ID NO:  6    1 HCTGAVSSFV----SVAPGQTARITCGEESLGSRSVIWYQQRPGQAPSLIIYNNNDRPSGIPERFSGSPGSTFGTTATLTI  77
SEQ ID NO:  8    1 HCTGAVSSFV----SVAPGQTARITCGEESLGSRSVIWYQQRPGQAPSLIIYNNNDRPSGIPERFSGSPGSTFGTTATLTI  77
SEQ ID NO: 10    1 HCTASLAS----SMSVSPGETAKISCGKESIGSRAVQWYQQKPGQPPSLIIYNNQDRPAGVPERFSASPDFRPGTTATLTI  77
SEQ ID NO: 12    1 HCTGSLAS----SMSVSPGETAKISCGKESIGSRAVQWYQQKPGQPPSLIIYNNQDRPAGVPERFSASPDFRPGTTATLTI  77

SEQ ID NO: 70   75 SRVEAGDEADYYCQVWDSSSDHPWVFGGGTKLTVL 109
SEQ ID NO:  2   78 SRVEAGDEADYYCHIWDSRFPLSWVFAGGTKLTVL 112
SEQ ID NO:  4   78 SGVEAGDEADYYCHMWDSRSGFSWSFGGATRLTVL 112
SEQ ID NO:  6   78 TSVEAGDEADYYCHIWDSRRPTNWVFGEGTTLTVL 112
SEQ ID NO:  8   78 TSVEAGDEADYYCHIWDSRRPTNWVFGEGTTLTVL 112
SEQ ID NO: 10   78 TNVDAEDEADYYCHIYDARGGTNWVFDRGTTLTVL 112
SEQ ID NO: 12   78 TNVDAEDEADYYCHIYDARGGTNWVFDRGTTLTVL 112
```

FIG. 6B

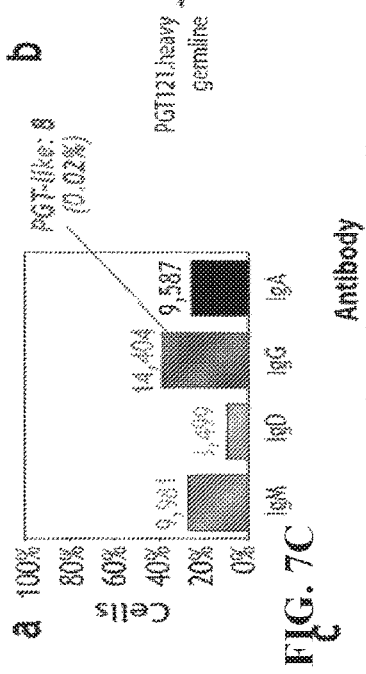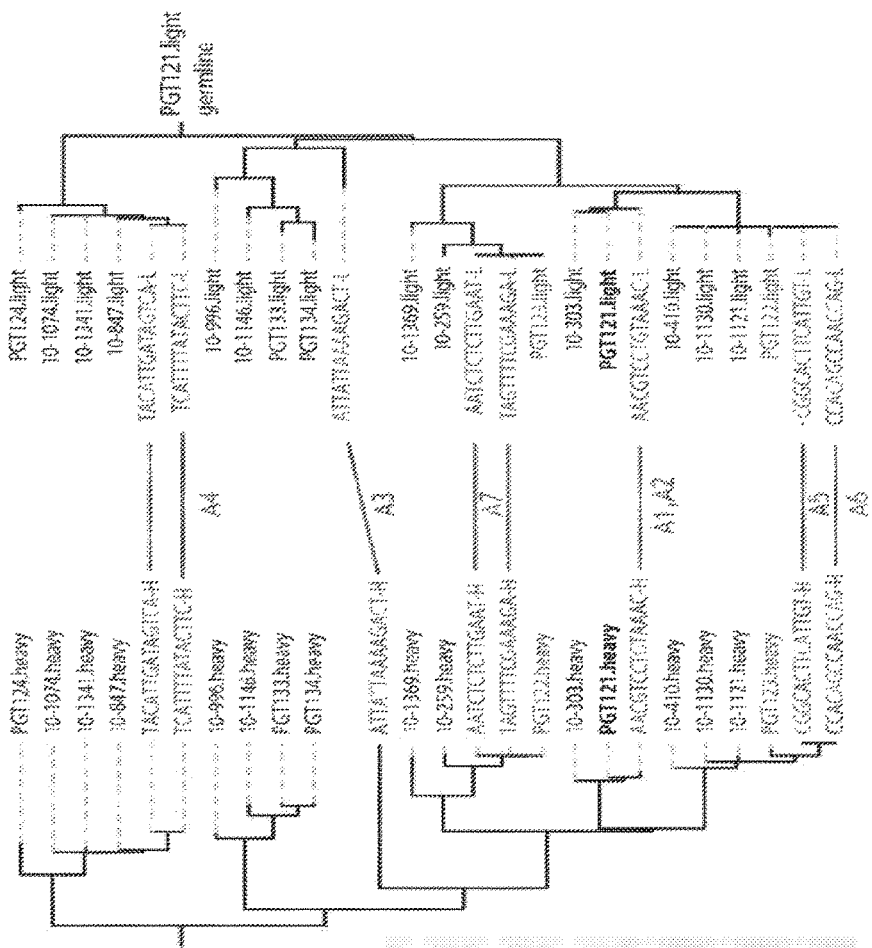
FIG. 7A  FIG. 7B  FIG. 7C
FIG. 7

BROADLY NEUTRALIZING ANTI-HIV-1 ANTIBODIES THAT BIND TO AN N-GLYCAN EPITOPE ON THE ENVELOPE

CROSS-REFERENCE TO RELATED APPLICATIONS

This application is a divisional application of U.S. application Ser. No. 15/762,442, filed Mar. 22, 2018, which is a U.S. National Phase Application under 35 U.S.C. § 371 of International Application No. PCT/US2016/053599, filed on Sep. 24, 2016, which claims priority to U.S. provisional patent application No. 62/232,279, filed Sep. 24, 2015, each of which are herein incorporated by reference in their entireties.

The instant application contains a Sequence Listing which has been filed electronically in ASCII format and is hereby incorporated by reference in its entirety. Said ASCII copy, created on Nov. 24, 2020, is named ABV710_17010755_SL.txt and is 74,260 bytes in size.

GOVERNMENT INTERESTS

The invention disclosed herein was made, at least in part, with government support under Grant No. P01 AI081677 from the National Institutes of Health. Accordingly, the U.S. Government has certain rights in this invention.

FIELD OF THE INVENTION

This invention relates to antibodies against Human Immunodeficiency Virus ("HIV") and methods of their use.

BACKGROUND OF THE INVENTION

HIV causes acquired immunodeficiency syndrome (AIDS), a condition in humans characterized by wasting syndromes, central nervous system degeneration and immunosuppression that results in life-threatening infections and malignancies. HIV type 1 (HIV-1) has resulted in over 25 million deaths since its discovery and 20-60 million people are predicted to become infected over the next two decades. Thus, therapeutic agents and methods for treating or inhibiting HIV infection are needed.

The serum of some HIV infected individuals show broadly neutralizing antibodies (bNAbs) of the IgG isotype. However, the specificity and activity of these antibodies remains largely unknown. Passive transfer of neutralizing antibodies can contribute to protection against virus challenge in animal models.

The success of most vaccines depends on antibodies, and HIV antibodies were correlated with protection in a recent anti-HIV vaccine trial. Although some patients developed broadly neutralizing antibodies against gp160 years after infection, the ability of autologous viruses to mutate prevented protection against HIV infection. Yet, broadly neutralizing activity applies selective pressure on the virus; allowing passive transfer of (bNAbs) to macaques to protect against SHIV infection. Thus, vaccines that elicit such antibodies may protect humans against HIV infection.

SUMMARY

This invention relates in some aspects to broadly-neutralizing anti-HIV antibodies.

In one aspect an anti-HIV antibody, such as an isolated anti-HIV antibody, is provided, wherein the anti-HIV antibody binds to or is capable of binding to an N-glycan epitope of an HIV with an affinity of 1 nM or less. In some embodiments, the antibody neutralizes or is capable of neutralizing HIV. In some embodiments, the antibody is a broadly neutralizing antibody. In other embodiments, HIV is HIV-1. In further embodiments, HIV is HIV-1 group M. The HIV can be HIV-1 Glade A (including A1 and/or A2), B, C, D, E, F (including F1 and/or F2), G, H, I, J, K, or any combination, subtype, or recombinant derivative (including circulating recombinant form (CRF)) thereof. In some embodiments, recombinant HIV-1 clades (in some embodiments referred to as circulating recombinant forms (CRFs)) are represented by a combination of the two clades from which they are derived. In some embodiments, exemplary CRFs include AB, AC, AG, DF, BC, etc.

In some embodiments, the antibody has been glycoengineered to modify the oligosaccharides in the Fc region and wherein the antibody has increased ADCC effector function as compared to a non-glycoengineered antibody. In some embodiments, the antibody is a monoclonal antibody. In some embodiments, the antibody is a human, humanized, or chimeric antibody. In some embodiments, the antibody is a full-length IgG class antibody. In other embodiments, the antibody is an antibody fragment. In further embodiments, the antibody is a single chain variable fragment (scFv).

In some embodiments, the antibody comprises a CDR-H1 comprising the amino acid sequence of SEQ ID NO: 17; a CDR-H2 comprising the amino acid sequence of SEQ ID NO: 18; and a CDR-H3 comprising the amino acid sequence of SEQ ID NO: 19. In some embodiments, the antibody further comprises a CDR-L1 comprising the amino acid sequence of SEQ ID NO: 20; a CDR-L2 comprising the amino acid sequence of SEQ ID NO: 21; and a CDR-L3 comprising the amino acid sequence of SEQ ID NO: 22.

In some embodiments, the antibody comprises a CDR-L1 comprising the amino acid sequence of SEQ ID NO: 20; a CDR-L2 comprising the amino acid sequence of SEQ ID NO: 21; and a CDR-L3 comprising the amino acid sequence of SEQ ID NO: 22.

In some embodiments, the antibody comprises a CDR-H1 comprising the amino acid sequence of SEQ ID NO: 23; a CDR-H2 comprising the amino acid sequence of SEQ ID NO: 24; and a CDR-H3 comprising the amino acid sequence of SEQ ID NO: 25. In some embodiments, the antibody further comprises a CDR-L1 comprising the amino acid sequence of SEQ ID NO: 26; a CDR-L2 comprising the amino acid sequence of SEQ ID NO: 27; and a CDR-L3 comprising the amino acid sequence of SEQ ID NO: 28.

In some embodiments, the antibody comprises a CDR-L1 comprising the amino acid sequence of SEQ ID NO: 26; a CDR-L2 comprising the amino acid sequence of SEQ ID NO: 27; and a CDR-L3 comprising the amino acid sequence of SEQ ID NO: 28.

In some embodiments, the antibody comprises a CDR-H1 comprising the amino acid sequence of SEQ ID NO: 29; a CDR-H2 comprising the amino acid sequence of SEQ ID NO: 30; and a CDR-H3 comprising the amino acid sequence of SEQ ID NO: 31. In some embodiments, the antibody further comprises a CDR-L1 comprising the amino acid sequence of SEQ ID NO: 32; a CDR-L2 comprising the amino acid sequence of SEQ ID NO: 33; and a CDR-L3 comprising the amino acid sequence of SEQ ID NO: 34.

In some embodiments, the antibody comprises a CDR-L1 comprising the amino acid sequence of SEQ ID NO: 32; a CDR-L2 comprising the amino acid sequence of SEQ ID NO: 33; and a CDR-L3 comprising the amino acid sequence of SEQ ID NO: 34.

In some embodiments, the antibody comprises a CDR-H1 comprising the amino acid sequence of SEQ ID NO: 35; a CDR-H2 comprising the amino acid sequence of SEQ ID NO: 36; and a CDR-H3 comprising the amino acid sequence of SEQ ID NO: 37. In some embodiments, the antibody further comprises a CDR-L1 comprising the amino acid sequence of SEQ ID NO: 38; a CDR-L2 comprising the amino acid sequence of SEQ ID NO: 39; and a CDR-L3 comprising the amino acid sequence of SEQ ID NO: 40.

In some embodiments, the antibody comprises a CDR-L1 comprising the amino acid sequence of SEQ ID NO: 38; a CDR-L2 comprising the amino acid sequence of SEQ ID NO: 39; and a CDR-L3 comprising the amino acid sequence of SEQ ID NO: 40.

In some embodiments, the antibody comprises a CDR-H1 comprising the amino acid sequence of SEQ ID NO: 41; a CDR-H2 comprising the amino acid sequence of SEQ ID NO: 42; a CDR-H3 comprising the amino acid sequence of SEQ ID NO: 43; and a $V_L$, sequence having the amino acid sequence of SEQ ID NO: 10.

In some embodiments, the antibody comprises a CDR-H1 comprising the amino acid sequence of SEQ ID NO: 17; a CDR-H2 comprising the amino acid sequence of SEQ ID NO: 18; a CDR-H3 comprising the amino acid sequence of SEQ ID NO: 16; and a $V_L$, sequence having the amino acid sequence of SEQ ID NO: 12.

In some embodiments, the antibody comprises a CDR-H1 comprising the amino acid sequence of SEQ ID NO: 53; a CDR-H2 comprising the amino acid sequence of SEQ ID NO: 54; and a CDR-H3 comprising the amino acid sequence of SEQ ID NO: 55. In some embodiments, the antibody further comprises a CDR-L1 comprising the amino acid sequence of SEQ ID NO: 56; a CDR-L2 comprising the amino acid sequence of SEQ ID NO: 57; and a CDR-L3 comprising the amino acid sequence of SEQ ID NO: 58.

In some embodiments, the antibody comprises a CDR-L1 comprising the amino acid sequence of SEQ ID NO: 56; a CDR-L2 comprising the amino acid sequence of SEQ ID NO: 57; and a CDR-L3 comprising the amino acid sequence of SEQ ID NO: 58.

In some embodiments, the antibody comprises a CDR-H1 comprising the amino acid sequence of SEQ ID NO: 59; a CDR-H2 comprising the amino acid sequence of SEQ ID NO: 60; and a CDR-H3 comprising the amino acid sequence of SEQ ID NO: 61.

In some embodiments, the antibody comprises a CDR-H1 comprising the amino acid sequence of SEQ ID NO: 62; a CDR-H2 comprising the amino acid sequence of SEQ ID NO: 63; and a CDR-H3 comprising the amino acid sequence of SEQ ID NO: 64. In some embodiments, the antibody further comprises a CDR-L1 comprising the amino acid sequence of SEQ ID NO: 26; a CDR-L2 comprising the amino acid sequence of SEQ ID NO: 27; and a CDR-L3 comprising the amino acid sequence of SEQ ID NO: 28. In some embodiments, the antibody further comprises a CDR-L1 comprising the amino acid sequence of SEQ ID NO: 66; a CDR-L2 comprising the amino acid sequence of SEQ ID NO: 67; and a CDR-L3 comprising the amino acid sequence of SEQ ID NO: 68.

In some embodiments, the antibody comprises a $V_H$ sequence having at least 95% sequence identity to the amino acid sequence of SEQ ID NO: 1; a $V_L$, sequence having at least 95% sequence identity to the amino acid sequence of SEQ ID NO: 2; or a $V_H$ sequence as in (a) and a $V_L$, sequence as in (b).

In some embodiments, the antibody comprises a $V_H$ sequence having at least 95% sequence identity to the amino acid sequence of SEQ ID NO: 3; a $V_L$ sequence having at least 95% sequence identity to the amino acid sequence of SEQ ID NO: 4; or a $V_H$ sequence as in (a) and a $V_L$ sequence as in (b).

In some embodiments, the antibody comprises a $V_H$ sequence having at least 95% sequence identity to the amino acid sequence of SEQ ID NO: 5; a $V_L$ sequence having at least 95% sequence identity to the amino acid sequence of SEQ ID NO: 6; or a $V_H$ sequence as in (a) and a $V_L$ sequence as in (b).

In some embodiments, the antibody comprises a $V_H$ sequence having at least 95% sequence identity to the amino acid sequence of SEQ ID NO: 7; a $V_L$ sequence having at least 95% sequence identity to the amino acid sequence of SEQ ID NO: 8; or a $V_H$ sequence as in (a) and a $V_L$ sequence as in (b).

In some embodiments, the antibody comprises a $V_H$ sequence having at least 95% sequence identity to the amino acid sequence of SEQ ID NO: 9; and a $V_L$ sequence having the amino acid sequence of SEQ ID NO: 10.

In some embodiments, the antibody comprises a $V_H$ sequence having at least 95% sequence identity to the amino acid sequence of SEQ ID NO: 11; and a $V_L$ sequence having the amino acid sequence of SEQ ID NO: 12.

In some embodiments, the antibody comprises a $V_H$ sequence having at least 95% sequence identity to the amino acid sequence of SEQ ID NO: 13; a $V_L$ sequence having at least 95% sequence identity to the amino acid sequence of SEQ ID NO: 14; or a $V_H$ sequence as in (a) and a $V_L$ sequence as in (b).

In some embodiments, the antibody comprises a $V_H$ sequence having at least 95% sequence identity to the amino acid sequence of SEQ ID NO: 16; or a $V_H$ sequence as in (a) and a $V_L$ sequence having at least 95% sequence identity to the amino acid sequence of SEQ ID NO: 4.

In some embodiments, the antibody comprises a $V_H$ sequence having at least 95% sequence identity to the amino acid sequence of SEQ ID NO: 16; or a $V_H$ sequence as in (a) and a $V_L$ sequence having at least 95% sequence identity to the amino acid sequence of SEQ ID NO: 65.

In some embodiments, the antibody does not comprise a CDR-H1 of Table 4, a CDR-H2 of Table 4, a CDR-H3 of Table 4, or any combination thereof; a CDR-L1 of Table 5, a CDR-L2 of Table 5, a CDR-L3 of Table 5, or any combination thereof; a $V_H$ sequence of Table 4, a $V_L$ sequence of Table 5, or both; or any combination of (a), (b), or (c).

In one aspect, an isolated nucleic acid is provided encoding any of the antibodies described herein. In one aspect, a vector is provided comprising the nucleic acid. In one aspect, a host cell comprising the vector is provided.

In one aspect, a method of producing an antibody is provided comprising culturing a host cell comprising a nucleic acid encoding any of the antibodies described herein so that the antibody is produced.

In one aspect, an immunoconjugate is provided comprising any of the antibodies described herein and a cytotoxic agent.

In one aspect, a pharmaceutical formulation is provided comprising of the antibodies described herein and a pharmaceutically acceptable carrier.

In one aspect, provided herein are any of the antibodies or immunoconjugates described herein for use as a medicament.

In one aspect, provided herein are any of the antibodies or immunoconjugates described herein for treating HIV infection or AIDS.

In one aspect, provided herein are any of the antibodies or immunoconjugates described herein for use in the manufacture of a medicament. In some embodiments, the medicament is for treatment of HIV infection or AIDS. In other embodiments, the medicament is for neutralizing HIV. In some embodiments, the antibody is a broadly neutralizing antibody. In some embodiments, HIV is HIV-1. In further embodiments, HIV is HIV-1 group M. The HIV can be HIV-1 Glade A (including A1 and/or A2), B, C, D, E, F (including F1 and/or F2), G, H, I, J, K, or any combination subtype, or recombinant derivative (including circulating recombinant form (CRF)) thereof. In some embodiments, recombinant HIV-1 clades (in some embodiments referred to as circulating recombinant forms (CRFs)) are represented by a combination of the two clades from which they are derived. In some embodiments, exemplary CRFs include AB, AC, AG, DF, BC, etc.

In one aspect, provided herein is a method of treating an individual having HIV infection or AIDS comprising administering to the individual an effective amount of any of the antibodies or immunoconjugates described herein. In some embodiments, the method further comprises administering a therapeutic agent. In some embodiments, the therapeutic agent is an antiviral agent.

In one aspect, provided herein is an HIV immunohistochemical assay comprising contacting a sample with any of the antibodies or immunoconjugates described herein under conditions permissive for formation of an antibody-HIV complex between the antibody and HIV present in the sample, and detecting the presence or absence of the complex by an immunodetection method. In some embodiments, the sample is a blood sample or a tissue sample.

In one aspect, provided herein is a method for making an anti-HIV antibody or a fragment thereof comprising culturing a host cell comprising a nucleic acid encoding any of the antibodies described herein in a medium under conditions permitting expression of a polypeptide encoded by the vector and assembling of an antibody or fragment thereof; and purifying the antibody or fragment from the host cell or the medium of the host cell.

In one aspect, provided herein is a kit comprising a pharmaceutically acceptable dosage unit of a pharmaceutically effective amount of at least one isolated anti-HIV antibody or immunoconjugate described herein. In some embodiments, the kit further comprises a pharmaceutically acceptable dosage unit of a pharmaceutically effective amount of an anti-HIV agent. In some embodiments, the anti-HIV agent is one selected from the group consisting of a non-nucleoside reverse transcriptase inhibitor, a protease inhibitor, an entry or fusion inhibitor, and an integrase inhibitor.

In one aspect, provided herein is a kit for the diagnosis, prognosis, or monitoring the treatment of an HIV infection or AIDS in a subject comprising at least one isolated anti-HIV antibody or immunoconjugate described herein, and one or more detection reagents which specifically bind to the anti-HIV antibodies. In some embodiments, the kit further comprises reagents for performing PCR. In some embodiments, the kit further comprises reagents for performing mass spectrometry.

In one aspect, a fusion protein or conjugate comprises any antibody described herein. In some embodiments, the fusion protein or conjugate is or comprises a chimeric receptor, which optionally is a chimeric antigen receptor (CAR).

In some embodiments, a chimeric antigen receptor (CAR) comprises any antibody described herein. In some embodiments, the chimeric antigen receptor is a CAR that further comprises an intracellular signaling domain comprising an ITAM motif. In other embodiments, the chimeric antigen receptor is a CAR that further comprises an intracellular signaling domain from CD3. In some embodiments, the chimeric antigen receptor is a CAR that further comprises an intracellular signaling domain from a costimulatory molecule selected from the group consisting of CD28, CD137, ICOS, and OX40.

INCORPORATION BY REFERENCE

All publications, patents, and patent applications herein are incorporated by reference in their entireties. In the event of a conflict between a term herein and a term in an incorporated reference, the term herein controls.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 3 discloses SEQ ID NOs: 100-108 (left column, from top to bottom) and SEQ ID NOs: 100-101, 103-106, 108, and 107 (right column, from top to bottom).

FIG. 4 discloses SEQ ID NOs: 100-108 (left column, from top to bottom) and SEQ ID NOs: 100-101 and 103-108 (right column, from top to bottom).

FIG. 6A depicts sequence alignments of germline and AbV1-9 clonal variants. (A) Amino acid alignment of the heavy chains (IgH) of the AbV1-9 antibodies, and the germline (GL) $V_H$ for clonal variants. Amino acid numbering based on crystal structures, framework (FWR) and complementary determining regions (CDR) as defined by Kabat (J Exp Med 132(2):21 1-250) are shown.

FIG. 6B depicts sequence alignments of germline and AbV1-9 clonal variants. Amino acid alignment of the light chains (IgL) of the AbV1-9 antibodies, and the germline (GL) $V_L$ for clonal variants. Amino acid numbering based on crystal structures, framework (FWR) and complementary determining regions (CDR) as defined by Kabat (J Exp Med 132(2):21 1-250) are shown.

FIG. 7 exemplifies results from a method of HIV bNAb discovery. B-cells from an HIV elite controller were entered into emulsion and BCR pairs were recovered. (FIG. 7A) Heavy chain isotype distribution of the 38,620 recovered $V_H V_L$ pairs, where a rare proportion of the IgG chains aligned well to previously known bNAbs ("PGT-like"). (FIG. 7B) Phylogenetic trees of complete VDJ amino acid sequences of known bNABs plus the newly recovered ones (connected by lines, labeled with droplet barcode), with heavy (left) and light chains (right) plotted separately. Potentially mismatched antibodies are PGT122.heavy and PGT123.light, and PCT123.heavy and PGT122.light. (FIG. 7C) Both the left and right columns of FIG. 7C disclose nucleotides 1-14 of SEQ ID NOs: 100-101 and 103-108 (from top to bottom). Neutralization activity ($IC_{50}$, μg/mL) of the 8 newly discovered PGT-like variants against ten strains of HIV, compared to a control stock of PGT121.

DETAILED DESCRIPTION OF THE INVENTION

Figure 1:
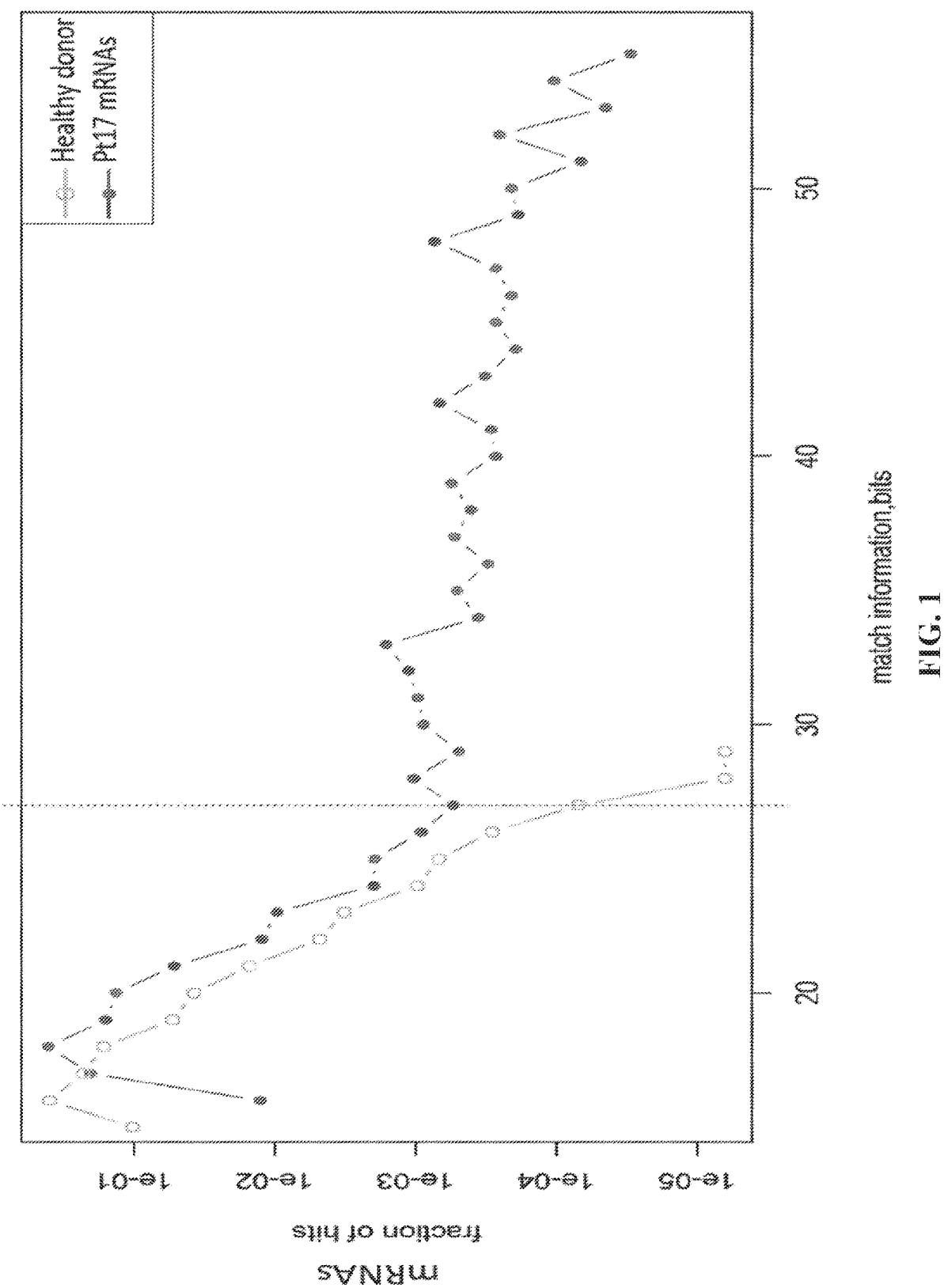
FIG. 1 depicts a graph with the results from a screening by heavy chain CDR3 similarity. Match similarity seen in a healthy volunteer suggests a "significance threshold" (initial permissive cutoff for antibody candidates in heavy chains from a donor).
Figure 2:
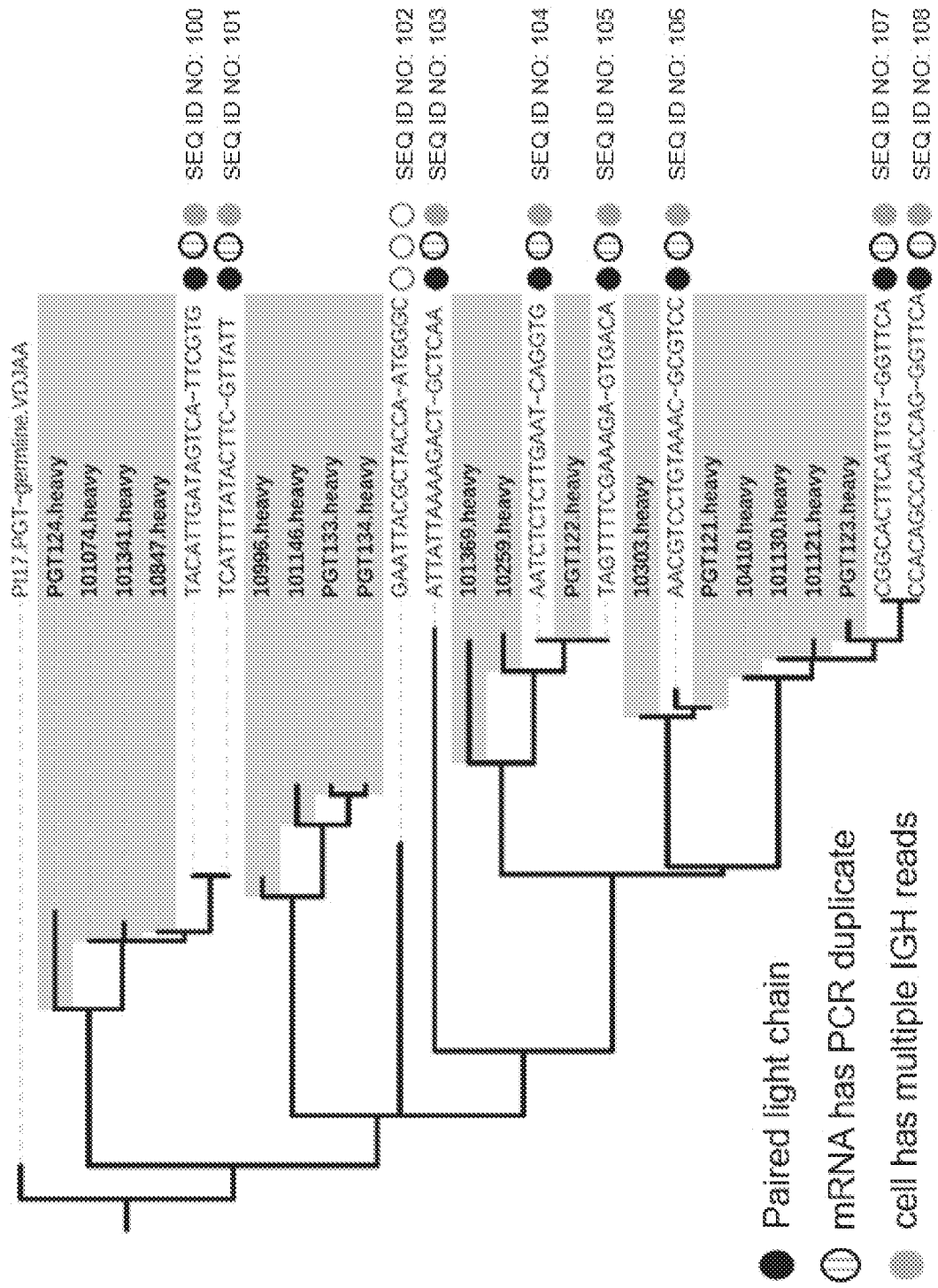
FIG. 2 depicts a chart of showing that the discovered antibodies phylogenetically segregate with known Pt17 BNAbs. Sequences of BNAbs from donor 17 were collected. Novel antibodies phylogenetically interspersed with these BNAbs were determined and likely arise from the same lineage. The phylogenetic relationship to the BNAbs was used to identifying new broadly neutralizing antibodies.
Figure 3:
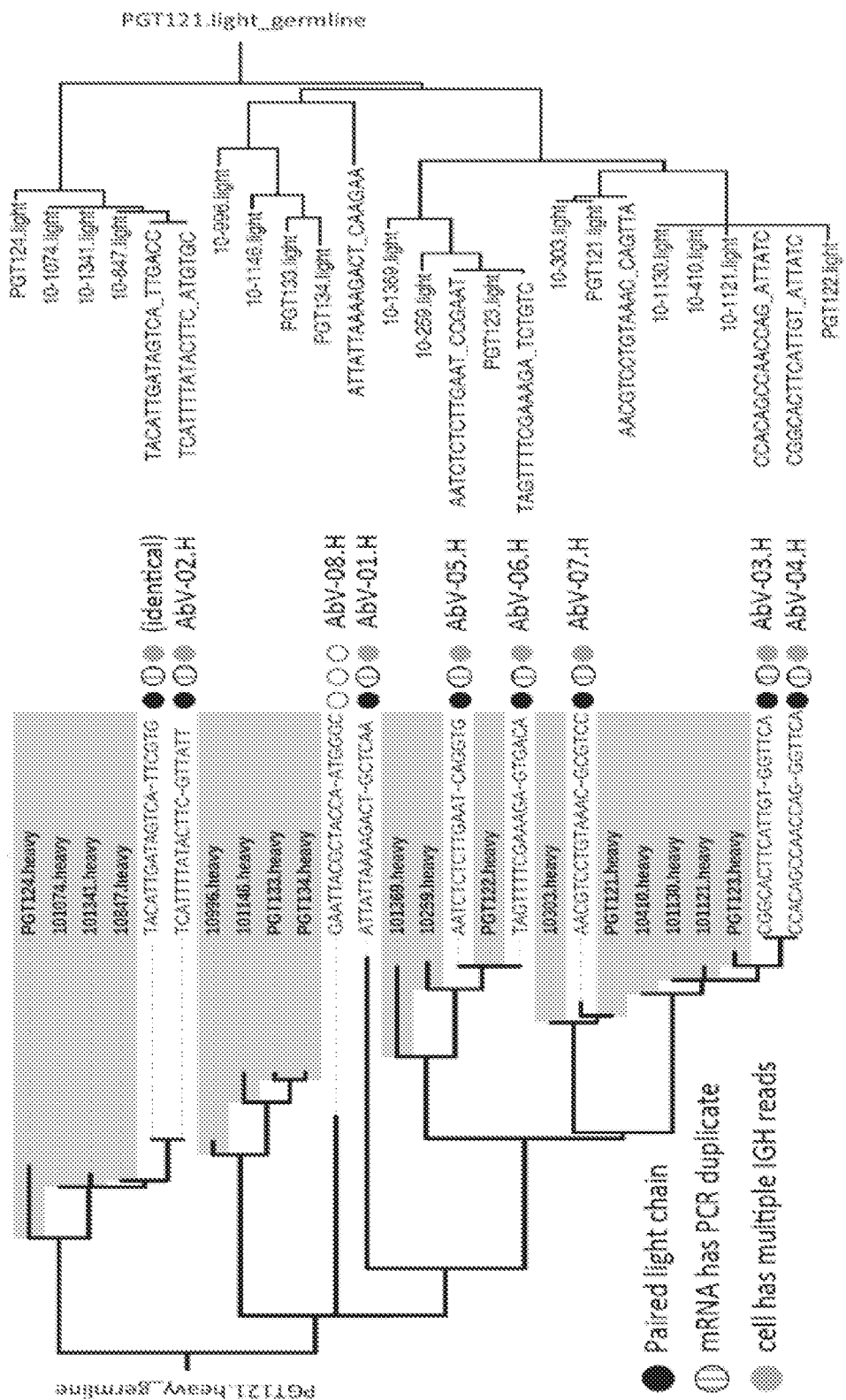
FIG. 3 depicts a chart of known and novel Abs derived from donor 17. New antibody pairs intersperse with known BNAbs (both heavy and light chain).
Figure 4:
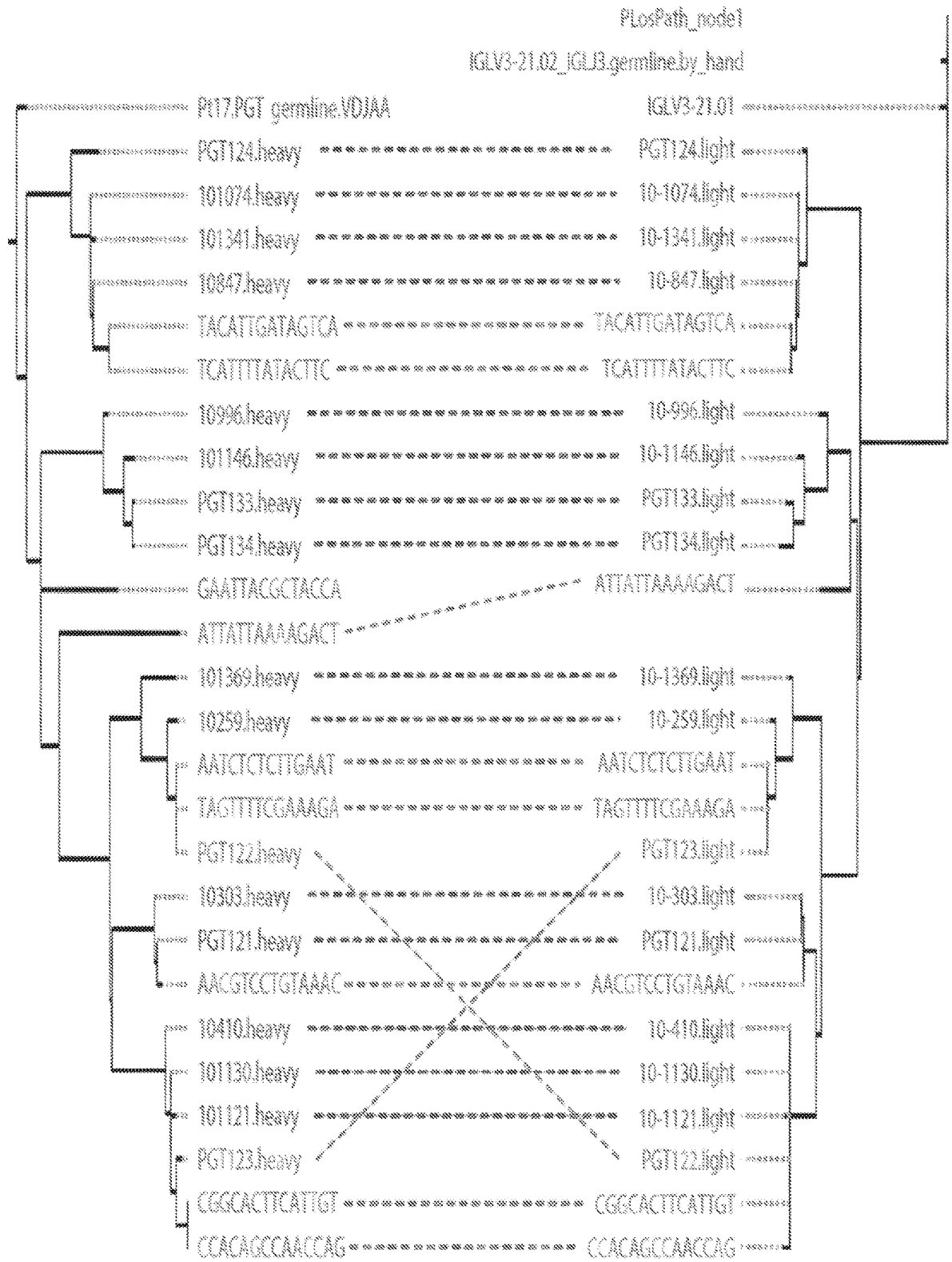
FIG. 4 depicts a chart showing known and discovered antibody heavy and light chain pairings.
Figure 5:
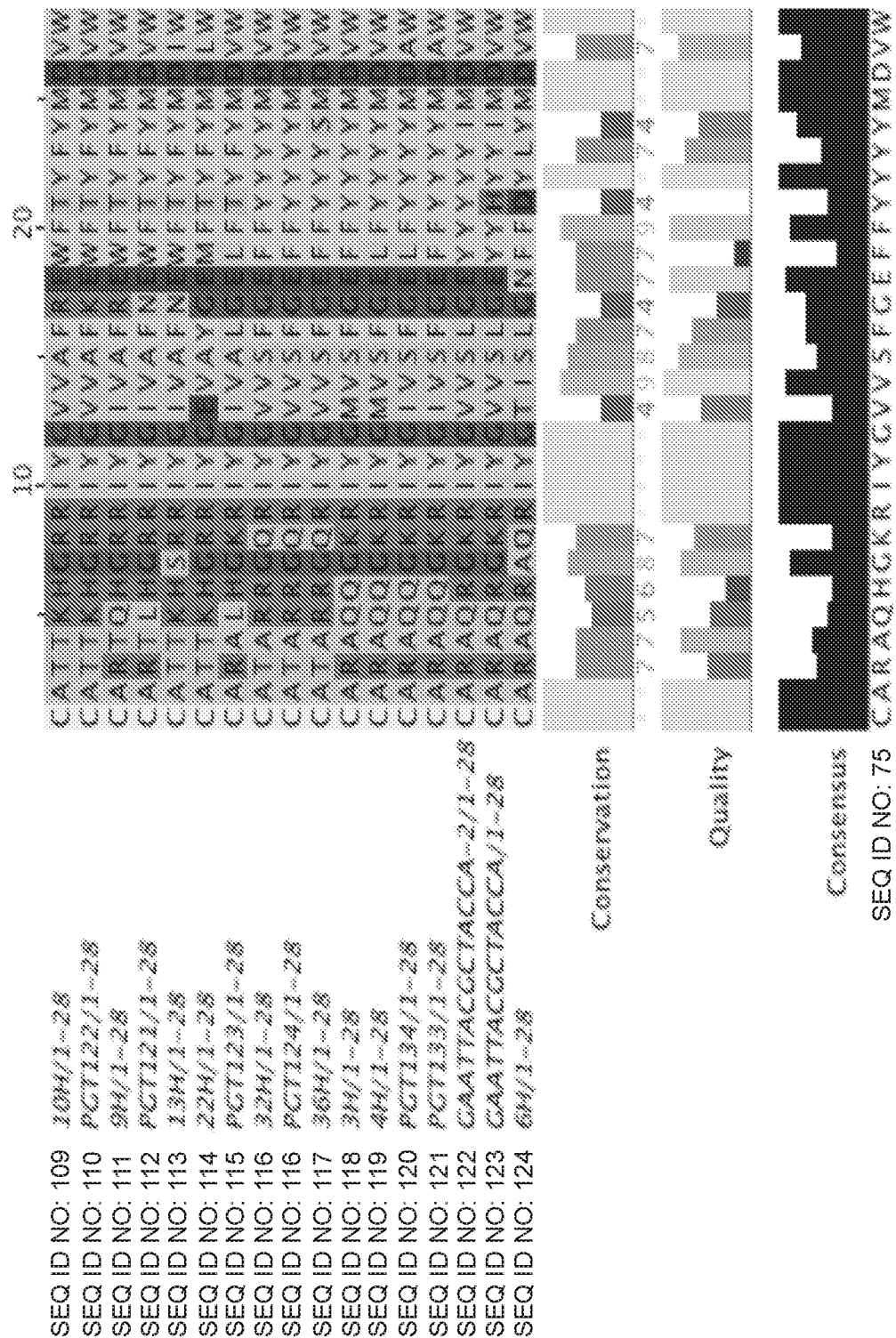
FIG. 5 depicts an alignment of AbV1-9 antibody variable region sequences compared to the variable region sequences of the germ line antibody. The DNA sequences disclosed in FIG. 5 both correspond to SEQ ID NO: 102.

In some aspects, the invention is based, at least in part, on an unexpected discovery of a new category of broadly neutralizing antibodies (bNAbs) against HIV that in some aspects can recognize carbohydrate-dependent epitopes, such as complex-type N-glycan, e.g., on gp120.

Among the provided antibodies are monoclonal antibodies, polyclonal antibodies, multispecific antibodies (for example, bispecific antibodies and polyreactive antibodies), and antibody fragments. The antibodies include antibody-conjugates and molecules comprising the antibodies, such as chimeric molecules; chimeric receptors comprising one or more stimulatory, signaling, and/or costimulatory domains; and chimeric antigen receptors (CARs). Thus, an antibody includes, but is not limited to, full-length and native antibodies, as well as fragments and portions thereof retaining the binding specificities thereof, such as any specific binding portion thereof, including those having any number of, immunoglobulin classes and/or isotypes (e.g., IgG1, IgG2, IgG3, IgG4, IgM, IgA, IgD, IgE and IgM); and biologically relevant (antigen-binding) fragments or specific binding portions thereof, including but not limited to Fab, F(ab')2, Fv, and scFv (single chain or related entity). A monoclonal antibody is generally one within a composition of substantially homogeneous antibodies; thus, any individual antibodies comprised within the monoclonal antibody composition are identical except for possible naturally occurring mutations that may be present in minor amounts. A polyclonal antibody is a preparation that includes different antibodies of varying sequences that generally are directed against two or more different determinants (epitopes).

Also provided are molecules such as chimeric and/or fusion molecules, including receptors, such as recombinant receptors, that include the antibody of any of the embodiments (e.g., contained in or part of an extracellular domain) and additional domains, such as intracellular signaling domains, spacers, linkers, and/or transmembrane domains. In some embodiments, the receptor is a chimeric antigen receptor, comprising an extracellular portion comprising the antibody or fragment of any of the embodiments and an intracellular signaling domain.

The term "antibody" herein thus is used in the broadest sense and includes polyclonal and monoclonal antibodies, including intact antibodies and functional (antigen-binding) antibody fragments thereof, including fragment antigen binding (Fab) fragments, $F(ab')_2$ fragments, Fab' fragments, Fv fragments, recombinant IgG (rIgG) fragments, single chain antibody fragments, including single chain variable fragments (sFv or scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

The terms "complementarity determining region," and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme), MacCallum et al., J. Mol. Biol. 262: 732-745 (1996), "Antibody-antigen interactions: Contact analysis and binding site topography," J. Mol. Biol. 262, 732-745.("Contact" numbering scheme), Lefranc MP et al., "IMGT unique numbering for immunoglobulin and T cell receptor variable domains and Ig superfamily V-like domains," Dev Comp Immunol, 2003 January; 27(1):55-77 ("IMGT" numbering scheme), and Honegger A and Pluckthun A, "Yet another numbering scheme for immunoglobulin variable domains: an automatic modeling and analysis tool," J Mol Biol, 2001 Jun. 8; 309(3):657-70, ("Aho" numbering scheme).

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Table A, below, lists exemplary position boundaries of CDR-L1, CDR-L2, CDR-L3 and CDR-H1, CDR-H2, CDR-H3 as identified by Kabat, Chothia, and Contact schemes, respectively. For CDR-H1, residue numbering is listed using both the Kabat and Chothia numbering schemes. FRs are located between CDRs, for example, with FR-L1 located between CDR-L1 and CDR-L2, and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE A

| CDR | Kabat | Chothia | Contact |
|---|---|---|---|
| CDR-L1 | L24--L34 | L24--L34 | L30--L36 |
| CDR-L2 | L50--L56 | L50--L56 | L46--L55 |
| CDR-L3 | L89--L97 | L89--L97 | L89--L96 |
| CDR-H1 (Kabat Numbering[1]) | H31--H35B | H26--H32 ... 34 | H30--H35B |
| CDR-H1 (Chothia Numbering[2]) | H31--H35 | H26--H32 | H30--H35 |
| CDR-H2 | H50--H65 | H52--H56 | H47--H58 |
| CDR-H3 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273, 927-948

Thus, unless otherwise specified, a "CDR" or "complementary determining region," or individual specified CDRs (e.g., CDR-H1, CDR-H2), of a given antibody or region thereof, such as a variable region thereof, should be understood to encompass a (or the specific) complementary determining region as defined by any of the aforementioned schemes. For example, where it is stated that a particular CDR (e.g., a CDR-H3) contains the amino acid sequence of a corresponding CDR in a given $V_H$ or $V_L$ amino acid sequence, it is understood that such a CDR has a sequence of the corresponding CDR (e.g., CDR-H3) within the variable region, as defined by any of the aforementioned schemes. In some embodiments, specified CDR sequences are specified.

Likewise, unless otherwise specified, a FR or individual specified FR(s) (e.g., FR-H1, FR-H2), of a given antibody or region thereof, such as a variable region thereof, should be understood to encompass a (or the specific) framework region as defined by any of the known schemes. In some instances, the scheme for identification of a particular CDR, FR, or FRs, or CDRs is specified, such as the CDR as defined by the Kabat, Chothia, or Contact method. In other cases, the particular amino acid sequence of a CDR or FR is given.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Among the provided antibodies are antibody fragments. An "antibody fragment" refers to a molecule other than an intact antibody that comprises a portion of an intact antibody that binds the antigen to which the intact antibody binds. Examples of antibody fragments include, but are not limited to, Fv, Fab, Fab', Fab'-SH, F(ab')$_2$; diabodies; linear antibodies; single-chain antibody molecules (e.g. scFv or sFv); and multispecific antibodies formed from antibody fragments. In particular embodiments, the antibodies are single-chain antibody fragments comprising a variable heavy chain region and/or a variable light chain region, such as scFvs.

Single-domain antibodies are antibody fragments comprising all or a portion of the heavy chain variable domain, or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or those that are not produced by enzyme digestion of a naturally-occurring intact antibody. In some aspects, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

Among the provided antibodies are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display, and other antibody display methods.

The terms "polypeptide" and "protein" are used interchangeably to refer to a polymer of amino acid residues, and are not limited to a minimum length. Polypeptides, including the provided antibodies and antibody chains and other peptides, e.g., linkers and binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Compositions and Methods

The invention in some embodiments provides anti-HIV antibodies (including but not limited to antigen-binding fragments of antibodies and conjugates, and/or fusion proteins of the antibodies, e.g., fragments, such as chimeric proteins, or chimeric receptors, e.g., chimeric antigen receptors (CARs) containing one or more of the antibodies). Such antibodies, fusion proteins and/or conjugates in some embodiments find use in treatment, diagnosis, and/or prognosis of HIV. Among the provided antibodies (and fusion proteins and conjugates thereof) are those that can neutralize HIV. The antibodies can be broadly neutralizing antibodies. In some embodiments, the antibodies of the invention can neutralize HIV-1 or HIV-2. For example, in some embodiments, the antibodies of the invention can neutralize HIV-1 group M, HIV-1 group N, HIV-1 group 0, and/or HIV-1 group P. In some embodiments, the antibodies of the invention can neutralize HIV-1 Glade A, B, C, D, E, F, G, H, I, J, K, or any combination, subtype, or recombinant derivative (including circulating recombinant form (CRF)) thereof. In some embodiments, antibodies that bind to a glycoprotein of HIV are provided. In some embodiments, antibodies with enhanced effector function that bind to HIV are provided. Among the provided fusion proteins and conjugates, including chimeric receptors such as chimeric antigen receptors (CARs), are proteins and conjugates that include any one or more of the provided antibodies, alone or in combination.

Exemplary Anti-HIV Antibodies

In one aspect, the invention provides antibodies, such as isolated antibodies, that bind to HIV. The HIV can be HIV-1. The HIV can be HIV-2. The HIV can be HIV-1 group M. The HIV can be HIV-1 group N, HIV-1 group 0, and/or HIV-1 group P. The HIV can be HIV-1 Glade A (including A1 and/or A2), B, C, D, E, F (including F1 and/or F2), G, H, I, J, K, or any combination, subtype, or recombinant derivative (including circulating recombinant form (CRF)) thereof. In some embodiments, recombinant HIV-1 clades (in some embodiments referred to as circulating recombinant forms (CRFs)) are represented by a combination of the two clades from which they are derived. In some embodiments, exemplary CRFs include AB, AC, AG, DF, BC, etc. In particular, the anti-HIV antibodies provided bind to an envelope glycoprotein of HIV. An isolated antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). (See, e.g., Flatman et al., J. Chromatogr. B 848:79-87 (2007)).

In particular, the anti-HIV antibodies provided bind to a complex-type N-glycan epitope of human HIV. In particular, the anti-HIV antibodies provided bind to gp120 of human HIV. The anti-HIV antibodies of the invention bind to an epitope present on the on gp120 domain of human HIV comprising a type N-glycan.

In some embodiments, the invention provides isolated antibodies that can neutralize HIV. A neutralizing antibody can be an antibody that inhibits the infectivity of a virus. In other embodiments, the invention provides isolated antibodies that can broadly neutralize HIV. A broadly neutralizing antibody can be an antibody that inhibits the infectivity of two or more strains or subtypes of a virus. The HIV can be HIV-1. The HIV can be HIV-2. The HIV can be HIV-1 group M. The HIV can be HIV-1 group N, HIV-1 group 0, and/or HIV-1 group P. The HIV can be HIV-1 Glade A (including A1 and/or A2), B, C, D, E, F (including F1 and/or F2), G, H, I, J, K, or any combination, subtype, or recombinant derivative (including circulating recombinant form (CRF)) thereof.

In some embodiments, the anti-HIV antibodies induce lysis of cells expressing HIV. Lysis can be induced by any mechanism, such as by mediating an effector function, such as C1q binding and complement dependent cytotoxicity (CDC); Fc receptor binding; antibody-dependent cell-mediated cytotoxicity (ADCC); phagocytosis; downregulation of cell surface receptors (e.g., B cell receptor); B cell activation, or direct induction of cell apoptosis.

In some embodiments, the anti-HIV antibody is engineered to have at least one increase in effector function as compared to the non-engineered parent anti-HIV antibody. Effector functions are biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation. For example, the anti-HIV antibody can be glycoengineered to have at least one increase in effector function as compared to the non-glycoengineered parent anti-HIV antibody. Antibody-dependent cell-mediated cytotoxicity (ADCC) is the result of the formation of a complex between the IgG Fab portion of the antibody with the viral protein on the cell surface and binding of the Fc portion to the Fc receptors (FcγRs), on effector cells. The increase in effector function can be increased binding affinity to an Fc receptor, increased ADCC; increased phagocytosis; increased cell mediated immunity; increased binding to cytotoxic CD8 T cells; increased binding to NK cells; increased binding to macrophages; increased binding to polymorphonuclear cells; increased binding to monocytes; increased binding to macrophages; increased binding to large granular lymphocytes; increased binding to granulocytes; direct signaling inducing apoptosis; increased dendritic cell maturation; or increased T cell priming. The glycoengineered anti-HIV antibodies provide a survival benefit in subjects suffering from cancers which express HIV as compared to non-glycoengineered antibodies directed to the same epitope of HIV.

AbV 1-9

In one aspect, an anti-HIV antibody comprises a $V_H$ sequence having at least 90%, 91%, 92%, 93%, 94%, 95%, 96%, 97%, 98%, 99%, or 100% sequence identity to the amino acid sequence of SEQ ID NO: 1, 3, 5, 7, 9, 11, 13, 15, and 16. In some embodiments, a $V_H$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. The anti-HIV antibody can retain the ability to bind to HIV-1. The anti-HIV antibody can retain the ability to bind to HIV-2. The anti-HIV antibody can retain the ability to bind to HIV-1 group M. The anti-HIV antibody can retain the ability to bind to HIV-1 group N, HIV-group 0, and/or HIV-1 group P. The anti-HIV antibody can retain the ability to bind to HIV-1 Glade A (including A1 and/or A2), B, C, D, E, F (including F1 and/or F2), G, H, I, J, K, or any combination, subtype, or recombinant derivative (including circulating recombinant form (CRF)) thereof. In some embodiments, a total of 1 to 10 amino acids have been substituted, inserted and/or deleted in the amino acid sequence of SEQ ID NO: 1, 3, 5, 7, 9, 11, 13, 15, and 16. In some embodiments, substitutions, insertions, or deletions occur in regions outside the CDRs (e.g., in the FRs). Optionally, the anti-HIV antibody comprises the $V_H$ sequence of the amino acid sequence of SEQ ID NO: 1, 3, 5, 7, 9, 11, 13, 15, and 16, including post-translational modifications of that sequence. In a particular embodiment, the $V_H$ comprises one, two or three CDRs selected from: (a) CDR-H1 comprising the amino acid sequence of SEQ ID NO: 17, 23, 29, 35, 41, 47, 53, 59, and 61, (b) CDR-H2 comprising the amino acid sequence of SEQ ID NO: 18, 24, 30, 36, 42, 48, 54, 60, and 63, and (c) CDR-H3 comprising the amino acid sequence of SEQ ID NO: 19, 25, 31, 37, 43, 49, 55, 61, and 64.

In one aspect, an anti-HIV antibody is provided, wherein the antibody comprises a light chain variable domain ($V_L$) having at least 90%, 91%, 92%, 93%, 94%, 95%, 96%, 97%, 98%, 99%, or 100% sequence identity to the amino acid sequence of SEQ ID NO: 2, 4, 6, 8, 10, 12, and 14. In some embodiments, a $V_L$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in any one of the amino acid sequence of SEQ ID NO: 2, 4, 6, 8, 10, 12, and 14. In some embodiments, the substitutions, insertions, or deletions occur in regions outside the CDRs (e.g., in the FRs). Optionally, the anti-HIV antibody comprises the $V_L$ sequence of SEQ ID NO: 2, 4, 6, 8, 10, 12, and 14, including post-translational modifications of that sequence. In a particular embodiment, the $V_L$ comprises one, two or three CDRs selected from (a) CDR-L1 comprising the amino acid sequence of SEQ ID NO: 20, 26, 32, 38, 44, 50, and 56; (b) CDR-L2 comprising the amino acid sequence of SEQ ID NO: 21, 27, 33, 39, 45, 51, and 57; and (c) CDR-L3 comprising the amino acid sequence of SEQ ID NO: 22, 28, 34, 40, 46, 52, and 58.

In one aspect, an anti-HIV antibody is provided, wherein the antibody comprises a $V_H$ as in any of the embodiments provided above, and a $V_L$ as in any of the embodiments provided above. In some embodiments, the antibody comprises a $V_H$ comprising the amino acid sequence of SEQ ID NO: 1, 3, 5, 7, 9, 11, 13, 15, and 16, and a $V_L$ sequence in SEQ ID NO: 2, 4, 6, 8, 10, 12, and 14, including post-translational modifications of those sequences.

In one aspect, an anti-HIV antibody is provided, wherein the antibody comprises a $V_H$ selected from any $V_H$ in Table 1. In one aspect, an anti-HIV antibody is provided, wherein the antibody comprises a $V_L$ selected from any $V_L$ in Table 2. In one aspect, an anti-HIV antibody is provided, wherein the antibody comprises a $V_H$ selected from any $V_H$ in Table 1 and a $V_L$ selected from any $V_L$ in Table 2. In one aspect, an anti-HIV antibody is provided, wherein the antibody comprises a $V_H$ selected from any $V_H$ in Table 1 and a $V_L$ selected from any $V_L$ in Table 2, wherein the selected $V_H$ and $V_L$ are paired according to Table 3.

AbV-1

In one aspect, the invention provides an anti-HIV antibody comprising at least one or both variable regions selected from (a) $V_H$ comprising the amino acid sequence of SEQ ID NO: 1 and (b) $V_L$ comprising the amino acid sequence of SEQ ID NO: 2.

In one aspect, the invention provides an anti-HIV antibody comprising at least one, two, three, four, five, or six CDRs selected from (a) CDR-H1 comprising the amino acid sequence of SEQ ID NO: 17; (b) CDR-H2 comprising the amino acid sequence of SEQ ID NO: 18; (c) CDR-H3 comprising the amino acid sequence of SEQ ID NO: 19; (d) CDR-L1 comprising the amino acid sequence of SEQ ID NO: 20; (e) CDR-L2 comprising the amino acid sequence of SEQ ID NO: 21; and (f) CDR-L3 comprising the amino acid sequence of SEQ ID NO: 22.

In one aspect, the invention provides an anti-HIV antibody comprising at least one, at least two, or all three $V_H$ CDR sequences selected from (a) CDR-H1 comprising the amino acid sequence of SEQ ID NO: 14; (b) CDR-H2 comprising the amino acid sequence of SEQ ID NO: 15; and (c) CDR-H3 comprising the amino acid sequence of SEQ ID NO: 16. In one aspect, the invention provides an anti-HIV antibody comprising at least one, at least two, or all three $V_H$ CDR sequences selected from (a) CDR-H1 comprising the amino acid sequence of SEQ ID NO: 14; (b) CDR-H2 comprising the amino acid sequence of SEQ ID NO: 15; and (c) CDR-H3 comprising the amino acid sequence of SEQ ID NO: 16; and (d) a $V_L$ comprising the amino acid sequence of SEQ ID NO: 2.

In one aspect, the invention provides an anti-HIV antibody comprising at least one, at least two, or all three $V_L$ CDR sequences selected from (a) CDR-L1 comprising the amino acid sequence of SEQ ID NO: 20; (b) CDR-L2 comprising the amino acid sequence of SEQ ID NO: 21 and (c) CDR-L3 comprising the amino acid sequence of SEQ ID NO: 22. In one aspect, the invention provides an anti-HIV antibody comprising at least one, at least two, or all three $V_L$ CDR sequences selected from (a) CDR-L1 comprising the amino acid sequence of SEQ ID NO: 20; (b) CDR-L2 comprising the amino acid sequence of SEQ ID NO: 21 and (c) CDR-L3 comprising the amino acid sequence of SEQ ID NO: 22; and (d) a $V_H$ comprising the amino acid sequence of SEQ ID NO: 1.

In one aspect, the invention provides an anti-HIV antibody comprising the CDRs: (a) CDR-H1 comprising the amino acid sequence of SEQ ID NO: 17; (b) CDR-H2 comprising the amino acid sequence of SEQ ID NO: 18; (c) CDR-H3 comprising the amino acid sequence of SEQ ID NO: 19; (d) CDR-L1 comprising the amino acid sequence of SEQ ID NO: 20; (e) CDR-L2 comprising the amino acid sequence of SEQ ID NO: 21; and (f) CDR-L3 comprising the amino acid sequence of SEQ ID NO: 22.

In one aspect, an anti-HIV antibody comprises a $V_H$ sequence having at least 90%, 91%, 92%, 93%, 94%, 95%, 96%, 97%, 98%, 99%, or 100% sequence identity to the amino acid sequence of SEQ ID NO: 1. In some embodiments, a $V_H$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in the amino acid sequence of SEQ ID NO: 1. In some embodiments, substitutions, insertions, or deletions occur in regions outside the CDRs (e.g., in the FRs). Optionally, the anti-HIV antibody comprises the $V_H$ sequence of the amino acid sequence of SEQ ID NO: 1, including post-translational modifications of that sequence. In a particular embodiment, the $V_H$ comprises one, two or three CDRs selected from: (a) CDR-H1 comprising the amino acid sequence of SEQ ID NO: 17, (b) CDR-H2 comprising the amino acid sequence of SEQ ID NO: 18, and (c) CDR-H3 comprising the amino acid sequence of SEQ ID NO: 19.

In one aspect, an anti-HIV antibody is provided, wherein the antibody comprises a light chain variable domain ($V_L$) having at least 90%, 91%, 92%, 93%, 94%, 95%, 96%, 97%, 98%, 99%, or 100% sequence identity to the amino acid sequence of SEQ ID NO: 2. In some embodiments, a $V_L$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in any one of the amino acid sequence of SEQ ID NO: 2. In some embodiments, the substitutions, insertions, or deletions occur in regions outside the CDRs (e.g., in the FRs). Optionally, the anti-HIV antibody comprises the $V_L$ sequence of SEQ ID NO: 2, including post-translational modifications of that sequence. In a particular embodiment, the $V_L$ comprises one, two or three CDRs selected from (a) CDR-L1 comprising the amino acid sequence of SEQ ID NO: 20; (b) CDR-L2 comprising the amino acid sequence of SEQ ID NO: 21; and (c) CDR-L3 comprising the amino acid sequence of SEQ ID NO: 22.

In one aspect, an anti-HIV antibody is provided, wherein the antibody comprises a $V_H$ as in any of the embodiments provided above, and a $V_L$ as in any of the embodiments provided above. In some embodiments, the antibody comprises a $V_H$ comprising the amino acid sequence of SEQ ID NO: 1, and a $V_L$ sequence in SEQ ID NO: 2, including post-translational modifications of those sequences. AbV-2

In one aspect, the invention provides an anti-HIV antibody comprising at least one or both variable regions selected from (a) $V_H$ comprising the amino acid sequence of SEQ ID NO: 3 and (b) $V_L$ comprising the amino acid sequence of SEQ ID NO: 4.

In one aspect, the invention provides an anti-HIV antibody comprising at least one, two, three, four, five, or six CDRs selected from (a) CDR-H1 comprising the amino acid sequence of SEQ ID NO: 23; (b) CDR-H2 comprising the amino acid sequence of SEQ ID NO: 24; (c) CDR-H3 comprising the amino acid sequence of SEQ ID NO: 25; (d) CDR-L1 comprising the amino acid sequence of SEQ ID NO: 26; (e) CDR-L2 comprising the amino acid sequence of SEQ ID NO: 27; and (f) CDR-L3 comprising the amino acid sequence of SEQ ID NO: 28.

In one aspect, the invention provides an anti-HIV antibody comprising at least one, at least two, or all three $V_H$ CDR sequences selected from (a) CDR-H1 comprising the amino acid sequence of SEQ ID NO: 23; (b) CDR-H2 comprising the amino acid sequence of SEQ ID NO: 24; and (c) CDR-H3 comprising the amino acid sequence of SEQ ID NO: 25. In one aspect, the invention provides an anti-HIV antibody comprising at least one, at least two, or all three $V_H$ CDR sequences selected from (a) CDR-H1 comprising the amino acid sequence of SEQ ID NO: 23; (b) CDR-H2 comprising the amino acid sequence of SEQ ID NO: 24; and (c) CDR-H3 comprising the amino acid sequence of SEQ ID NO: 25; and (d) a $V_L$ comprising the amino acid sequence of SEQ ID NO: 4.

In one aspect, the invention provides an anti-HIV antibody comprising at least one, at least two, or all three $V_L$ CDR sequences selected from (a) CDR-L1 comprising the amino acid sequence of SEQ ID NO: 26; (b) CDR-L2 comprising the amino acid sequence of SEQ ID NO: 27 and (c) CDR-L3 comprising the amino acid sequence of SEQ ID NO: 28. In one aspect, the invention provides an anti-HIV antibody comprising at least one, at least two, or all three $V_L$ CDR sequences selected from (a) CDR-L1 comprising the amino acid sequence of SEQ ID NO: 26; (b) CDR-L2 comprising the amino acid sequence of SEQ ID NO: 27 and (c) CDR-L3 comprising the amino acid sequence of SEQ ID NO: 28; and (d) a $V_H$ comprising the amino acid sequence of SEQ ID NO: 3. In one aspect, the invention provides an anti-HIV antibody comprising CDRs: (a) CDR-H1 comprising the amino acid sequence of SEQ ID NO: 23; (b) CDR-H2 comprising the amino acid sequence of SEQ ID NO: 24; (c) CDR-H3 comprising the amino acid sequence of SEQ ID NO: 25; (d) CDR-L1 comprising the amino acid sequence of SEQ ID NO: 26; (e) CDR-L2 comprising the amino acid sequence of SEQ ID NO: 27; and (f) CDR-L3 comprising the amino acid sequence of SEQ ID NO: 28.

In one aspect, an anti-HIV antibody comprises a $V_H$ sequence having at least 90%, 91%, 92%, 93%, 94%, 95%, 96%, 97%, 98%, 99%, or 100% sequence identity to the amino acid sequence of SEQ ID NO: 3. In some embodiments, a $V_H$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in the amino acid sequence of SEQ ID NO: 3. In some embodiments, substitutions, insertions, or deletions occur in regions outside the CDRs (e.g., in the FRs). Optionally, the anti-HIV antibody comprises the $V_H$ sequence of the amino acid sequence of SEQ ID NO: 3, including post-translational modifications of that sequence. In a particular embodiment, the $V_H$ comprises one, two or three CDRs selected from: (a) CDR-H1 comprising the amino acid sequence of SEQ ID NO: 23, (b) CDR-H2 comprising the amino acid sequence of SEQ ID NO: 24, and (c) CDR-H3 comprising the amino acid sequence of SEQ ID NO: 25.

In one aspect, an anti-HIV antibody is provided, wherein the antibody comprises a light chain variable domain ($V_L$) having at least 90%, 91%, 92%, 93%, 94%, 95%, 96%, 97%, 98%, 99%, or 100% sequence identity to the amino acid sequence of SEQ ID NO: 4. In some embodiments, a $V_L$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in any one of the amino acid sequence of SEQ ID NO: 4. In some embodiments, the substitutions, insertions, or deletions occur in regions outside the CDRs (e.g., in the FRs). Optionally, the anti-HIV antibody comprises the $V_L$ sequence of SEQ ID NO: 4, including post-translational modifications of that sequence. In a particular embodiment, the $V_L$ comprises one, two or three CDRs selected from (a) CDR-L1 comprising the amino acid sequence of SEQ ID NO: 26; (b) CDR-L2 comprising the amino acid sequence of SEQ ID NO: 27; and (c) CDR-L3 comprising the amino acid sequence of SEQ ID NO: 28.

In one aspect, an anti-HIV antibody is provided, wherein the antibody comprises a $V_H$ as in any of the embodiments provided above, and a $V_L$ as in any of the embodiments provided above. In some embodiments, the antibody comprises a $V_H$ comprising the amino acid sequence of SEQ ID NO: 3, and a $V_L$ sequence in SEQ ID NO: 4, including post-translational modifications of those sequences.

AbV-3

In one aspect, the invention provides an anti-HIV antibody comprising at least one or both variable regions selected from (a) $V_H$ comprising the amino acid sequence of SEQ ID NO: 5 and (b) $V_L$ comprising the amino acid sequence of SEQ ID NO: 6.

In one aspect, the invention provides an anti-HIV antibody comprising at least one, two, three, four, five, or six CDRs selected from (a) CDR-H1 comprising the amino acid sequence of SEQ ID NO: 29; (b) CDR-H2 comprising the amino acid sequence of SEQ ID NO: 30; (c) CDR-H3 comprising the amino acid sequence of SEQ ID NO: 31; (d) CDR-L1 comprising the amino acid sequence of SEQ ID NO: 32; (e) CDR-L2 comprising the amino acid sequence of SEQ ID NO: 33; and (f) CDR-L3 comprising the amino acid sequence of SEQ ID NO: 34.

In one aspect, the invention provides an anti-HIV antibody comprising at least one, at least two, or all three $V_H$ CDR sequences selected from (a) CDR-H1 comprising the amino acid sequence of SEQ ID NO: 2914; (b) CDR-H2 comprising the amino acid sequence of SEQ ID NO: 30; and (c) CDR-H3 comprising the amino acid sequence of SEQ ID NO: 31. In one aspect, the invention provides an anti-HIV antibody comprising at least one, at least two, or all three $V_H$ CDR sequences selected from (a) CDR-H1 comprising the amino acid sequence of SEQ ID NO: 2914; (b) CDR-H2 comprising the amino acid sequence of SEQ ID NO: 30; and (c) CDR-H3 comprising the amino acid sequence of SEQ ID NO: 31; and (d) a $V_L$ comprising the amino acid sequence of SEQ ID NO: 6.

In one aspect, the invention provides an anti-HIV antibody comprising at least one, at least two, or all three $V_L$ CDR sequences selected from (a) CDR-L1 comprising the amino acid sequence of SEQ ID NO: 32; (b) CDR-L2 comprising the amino acid sequence of SEQ ID NO: 33 and (c) CDR-L3 comprising the amino acid sequence of SEQ ID NO: 34. In one aspect, the invention provides an anti-HIV antibody comprising at least one, at least two, or all three $V_L$ CDR sequences selected from (a) CDR-L1 comprising the amino acid sequence of SEQ ID NO: 32; (b) CDR-L2 comprising the amino acid sequence of SEQ ID NO: 33 and (c) CDR-L3 comprising the amino acid sequence of SEQ ID NO: 34; and (d) a $V_H$ comprising the amino acid sequence of SEQ ID NO: 5.

In one aspect, the invention provides an anti-HIV antibody comprising CDRs: (a) CDR-H1 comprising the amino acid sequence of SEQ ID NO: 29; (b) CDR-H2 comprising the amino acid sequence of SEQ ID NO: 30; (c) CDR-H3 comprising the amino acid sequence of SEQ ID NO: 31; (d) CDR-L1 comprising the amino acid sequence of SEQ ID NO: 32; (e) CDR-L2 comprising the amino acid sequence of SEQ ID NO: 33; and (f) CDR-L3 comprising the amino acid sequence of SEQ ID NO: 34.

In one aspect, an anti-HIV antibody comprises a $V_H$ sequence having at least 90%, 91%, 92%, 93%, 94%, 95%, 96%, 97%, 98%, 99%, or 100% sequence identity to the amino acid sequence of SEQ ID NO: 5. In some embodiments, a $V_H$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in the amino acid sequence of SEQ ID NO: 5. In some embodiments, substitutions, insertions, or deletions occur in regions outside the CDRs (e.g., in the FRs). Optionally, the anti-HIV antibody comprises the $V_H$ sequence of the amino acid sequence of SEQ ID NO: 5, including post-translational modifications of that sequence. In a particular embodiment, the $V_H$ comprises one, two or three CDRs selected from: (a) CDR-H1 comprising the amino acid sequence of SEQ ID NO: 29, (b) CDR-H2 comprising the amino acid sequence of SEQ ID NO: 30, and (c) CDR-H3 comprising the amino acid sequence of SEQ ID NO: 31.

In one aspect, an anti-HIV antibody is provided, wherein the antibody comprises a light chain variable domain ($V_L$) having at least 90%, 91%, 92%, 93%, 94%, 95%, 96%, 97%, 98%, 99%, or 100% sequence identity to the amino acid sequence of SEQ ID NO: 6. In some embodiments, a $V_L$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in any one of the amino acid sequence of SEQ ID NO: 6 In some embodiments, the substitutions, insertions, or deletions occur in regions outside the CDRs (e.g., in the FRs). Optionally, the anti-HIV antibody comprises the $V_L$ sequence of SEQ ID NO: 6, including post-translational modifications of that sequence. In a particular embodiment, the $V_L$ comprises one, two or three CDRs selected from (a) CDR-L1 comprising the amino acid sequence of SEQ ID NO: 32; (b) CDR-L2 comprising the amino acid sequence of SEQ ID NO: 33; and (c) CDR-L3 comprising the amino acid sequence of SEQ ID NO: 34.

In one aspect, an anti-HIV antibody is provided, wherein the antibody comprises a $V_H$ as in any of the embodiments provided above, and a $V_L$ as in any of the embodiments provided above. In some embodiments, the antibody comprises a $V_H$ comprising the amino acid sequence of SEQ ID NO: 5, and a $V_L$ sequence in SEQ ID NO: 6, including post-translational modifications of those sequences.

AbV-4

In one aspect, the invention provides an anti-HIV antibody comprising at least one or both variable regions selected from (a) $V_H$ comprising the amino acid sequence of SEQ ID NO: 7 and (b) $V_L$ comprising the amino acid sequence of SEQ ID NO: 8.

In one aspect, the invention provides an anti-HIV antibody comprising at least one, two, three, four, five, or six CDRs selected from (a) CDR-H1 comprising the amino acid sequence of SEQ ID NO: 35; (b) CDR-H2 comprising the amino acid sequence of SEQ ID NO: 36; (c) CDR-H3 comprising the amino acid sequence of SEQ ID NO: 37; (d) CDR-L1 comprising the amino acid sequence of SEQ ID NO: 38; (e) CDR-L2 comprising the amino acid sequence of SEQ ID NO: 39; and (f) CDR-L3 comprising the amino acid sequence of SEQ ID NO: 40.

In one aspect, the invention provides an anti-HIV antibody comprising at least one, at least two, or all three $V_H$ CDR sequences selected from (a) CDR-H1 comprising the amino acid sequence of SEQ ID NO: 35; (b) CDR-H2 comprising the amino acid sequence of SEQ ID NO: 36; and (c) CDR-H3 comprising the amino acid sequence of SEQ ID NO: 37. In one aspect, the invention provides an anti-HIV antibody comprising at least one, at least two, or all three $V_H$ CDR sequences selected from (a) CDR-H1 comprising the amino acid sequence of SEQ ID NO: 35; (b) CDR-H2 comprising the amino acid sequence of SEQ ID NO: 36; and (c) CDR-H3 comprising the amino acid sequence of SEQ ID NO: 37; and (d) a $V_L$ comprising the amino acid sequence of SEQ ID NO: 8.

In one aspect, the invention provides an anti-HIV antibody comprising at least one, at least two, or all three $V_L$ CDR sequences selected from (a) CDR-L1 comprising the amino acid sequence of SEQ ID NO: 38; (b) CDR-L2 comprising the amino acid sequence of SEQ ID NO: 39 and (c) CDR-L3 comprising the amino acid sequence of SEQ ID NO: 40. In one aspect, the invention provides an anti-HIV antibody comprising at least one, at least two, or all three $V_L$ CDR sequences selected from (a) CDR-L1 comprising the amino acid sequence of SEQ ID NO: 38; (b) CDR-L2 comprising the amino acid sequence of SEQ ID NO: 39 and (c) CDR-L3 comprising the amino acid sequence of SEQ ID NO: 40; and (d) a $V_H$ comprising the amino acid sequence of SEQ ID NO: 7.

In one aspect, the invention provides an anti-HIV antibody comprising CDRs: (a) CDR-H1 comprising the amino acid sequence of SEQ ID NO: 35; (b) CDR-H2 comprising the amino acid sequence of SEQ ID NO: 36; (c) CDR-H3 comprising the amino acid sequence of SEQ ID NO: 37; (d) CDR-L1 comprising the amino acid sequence of SEQ ID NO: 38; (e) CDR-L2 comprising the amino acid sequence of SEQ ID NO: 39; and (f) CDR-L3 comprising the amino acid sequence of SEQ ID NO: 40.

In one aspect, an anti-HIV antibody comprises a $V_H$ sequence having at least 90%, 91%, 92%, 93%, 94%, 95%, 96%, 97%, 98%, 99%, or 100% sequence identity to the amino acid sequence of SEQ ID NO: 7. In some embodiments, a $V_H$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in the amino acid sequence of SEQ ID NO: 7. In some embodiments, substitutions, insertions, or deletions occur in regions outside the CDRs (e.g., in the FRs). Optionally, the anti-HIV antibody comprises the $V_H$ sequence of the amino acid sequence of SEQ ID NO: 7, including post-translational modifications of that sequence. In a particular embodiment, the $V_H$ comprises one, two or three CDRs selected from: (a) CDR-H1 comprising the amino acid sequence of SEQ ID NO: 35, (b) CDR-H2 comprising the amino acid sequence of SEQ ID NO: 36, and (c) CDR-H3 comprising the amino acid sequence of SEQ ID NO: 37.

In one aspect, an anti-HIV antibody is provided, wherein the antibody comprises a light chain variable domain ($V_L$) having at least 90%, 91%, 92%, 93%, 94%, 95%, 96%, 97%, 98%, 99%, or 100% sequence identity to the amino acid sequence of SEQ ID NO: 8. In some embodiments, a $V_L$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in any one of the amino acid sequence of SEQ ID NO: 8. In some embodiments, the substitutions, insertions, or deletions occur in regions outside the CDRs (e.g., in the FRs). Optionally, the anti-HIV antibody comprises the $V_L$ sequence of SEQ ID NO: 8, including post-translational modifications of that sequence. In a particular embodiment, the $V_L$ comprises one, two or three CDRs selected from (a) CDR-L1 comprising the amino acid sequence of SEQ ID NO: 38; (b) CDR-L2 comprising the amino acid sequence of SEQ ID NO: 39; and (c) CDR-L3 comprising the amino acid sequence of SEQ ID NO: 40.

In one aspect, an anti-HIV antibody is provided, wherein the antibody comprises a $V_H$ as in any of the embodiments provided above, and a $V_L$ as in any of the embodiments provided above. In some embodiments, the antibody comprises a $V_H$ comprising the amino acid sequence of SEQ ID NO: 7, and a $V_L$ sequence in SEQ ID NO: 8, including post-translational modifications of those sequences.

Ab V-5

In one aspect, the invention provides an anti-HIV antibody comprising both variable regions selected from (a) $V_H$ comprising the amino acid sequence of SEQ ID NO: 9 and (b) $V_L$ comprising the amino acid sequence of SEQ ID NO: 10.

In one aspect, the invention provides an anti-HIV antibody comprising at least one, at least two, or all three $V_H$ CDR sequences selected from (a) CDR-H1 comprising the amino acid sequence of SEQ ID NO: 41; (b) CDR-H2 comprising the amino acid sequence of SEQ ID NO: 42; and (c) CDR-H3 comprising the amino acid sequence of SEQ ID NO: 43; and at least one, at least two, or all three $V_L$ CDR sequences selected from (d) CDR-L1 comprising the amino acid sequence of SEQ ID NO: 44; (e) CDR-L2 comprising the amino acid sequence of SEQ ID NO: 45; and (f) CDR-L3 comprising the amino acid sequence of SEQ ID NO: 46.

In one aspect, the invention provides an anti-HIV antibody comprising CDRs: (a) CDR-H1 comprising the amino acid sequence of SEQ ID NO: 41; (b) CDR-H2 comprising the amino acid sequence of SEQ ID NO: 42; (c) CDR-H3 comprising the amino acid sequence of SEQ ID NO: 43; (d) CDR-L1 comprising the amino acid sequence of SEQ ID NO: 44; (e) CDR-L2 comprising the amino acid sequence of SEQ ID NO: 45; and (f) CDR-L3 comprising the amino acid sequence of SEQ ID NO: 46.

In one aspect, an anti-HIV antibody comprises a $V_H$ sequence having at least 90%, 91%, 92%, 93%, 94%, 95%, 96%, 97%, 98%, 99%, or 100% sequence identity to the amino acid sequence of SEQ ID NO: 9. In some embodiments, a $V_H$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in the amino acid sequence of SEQ ID NO: 9. In some embodiments, substitutions, insertions, or deletions occur in regions outside the CDRs (e.g., in the FRs). Optionally, the anti-HIV antibody comprises the $V_H$ sequence of the amino acid sequence of SEQ ID NO: 9, including post-translational modifications of that sequence. In a particular embodiment, the $V_H$ comprises one, two or three CDRs selected from: (a) CDR-H1 comprising the amino acid sequence of SEQ ID NO: 41, (b) CDR-H2 comprising the amino acid sequence of SEQ ID NO: 42, and (c) CDR-H3 comprising the amino acid sequence of SEQ ID NO: 43.

In one aspect, an anti-HIV antibody is provided, wherein the antibody comprises a light chain variable domain ($V_L$) having at least 90%, 91%, 92%, 93%, 94%, 95%, 96%, 97%, 98%, 99%, or 100% sequence identity to the amino acid sequence of SEQ ID NO: 10. In some embodiments, a $V_L$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in any one of the amino acid sequence of SEQ ID NO: 10. In some embodiments, the substitutions, insertions, or deletions occur in regions outside the CDRs (e.g., in the FRs). Optionally, the anti-HIV antibody comprises the $V_L$ sequence of SEQ ID NO: 10, including post-translational modifications of that sequence. In a particular embodiment, the $V_L$ comprises one, two or three CDRs selected from (a) CDR-L1 comprising the amino acid sequence of SEQ ID NO: 44: 10; (b) CDR-L2 comprising the amino acid sequence of SEQ ID NO: 45; and (c) CDR-L3 comprising the amino acid sequence of SEQ ID NO: 46.

In one aspect, an anti-HIV antibody is provided, wherein the antibody comprises a $V_H$ as in any of the embodiments provided above, and a $V_L$ as in any of the embodiments provided above. In some embodiments, the antibody comprises a $V_H$ comprising the amino acid sequence of SEQ ID NO: 9, and a $V_L$ sequence in SEQ ID NO: 10, including post-translational modifications of those sequences.

AbV-6

In one aspect, the invention provides an anti-HIV antibody comprising both variable regions selected from (a) $V_H$ comprising the amino acid sequence of SEQ ID NO: 11 and (b) $V_L$ comprising the amino acid sequence of SEQ ID NO: 12.

In one aspect, the invention provides an anti-HIV antibody comprising at least one, at least two, or all three $V_H$ CDR sequences selected from (a) CDR-H1 comprising the amino acid sequence of SEQ ID NO: 47; (b) CDR-H2 comprising the amino acid sequence of SEQ ID NO: 48; and (c) CDR-H3 comprising the amino acid sequence of SEQ ID NO: 49; and at least one, at least two, or all three $V_L$ CDR sequences selected from (d) CDR-L1 comprising the amino acid sequence of SEQ ID NO: 50; (e) CDR-L2 comprising the amino acid sequence of SEQ ID NO: 51; and (f) CDR-L3 comprising the amino acid sequence of SEQ ID NO: 52.

In one aspect, the invention provides an anti-HIV antibody comprising CDRs: (a) CDR-H1 comprising the amino acid sequence of SEQ ID NO: 47; (b) CDR-H2 comprising the amino acid sequence of SEQ ID NO: 48; and (c) CDR-H3 comprising the amino acid sequence of SEQ ID NO: 49; (d) CDR-L1 comprising the amino acid sequence of SEQ ID NO: 50; (e) CDR-L2 comprising the amino acid sequence of SEQ ID NO: 51; and (f) CDR-L3 comprising the amino acid sequence of SEQ ID NO: 52.

In one aspect, an anti-HIV antibody comprises a $V_H$ sequence having at least 90%, 91%, 92%, 93%, 94%, 95%, 96%, 97%, 98%, 99%, or 100% sequence identity to the amino acid sequence of SEQ ID NO: 11. In some embodiments, a $V_H$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in the amino acid sequence of SEQ ID NO: 11. In some embodiments, substitutions, insertions, or deletions occur in regions outside the CDRs (e.g., in the FRs). Optionally, the anti-HIV antibody comprises the $V_H$ sequence of the amino acid sequence of SEQ ID NO: 11, including post-translational modifications of that sequence. In a particular embodiment, the $V_H$ comprises one, two or three CDRs selected from: (a) CDR-H1 comprising the amino acid sequence of SEQ ID NO: 47, (b) CDR-H2 comprising the amino acid sequence of SEQ ID NO: 48, and (c) CDR-H3 comprising the amino acid sequence of SEQ ID NO: 49.

In one aspect, an anti-HIV antibody is provided, wherein the antibody comprises a light chain variable domain ($V_L$) having at least 90%, 91%, 92%, 93%, 94%, 95%, 96%, 97%, 98%, 99%, or 100% sequence identity to the amino acid sequence of SEQ ID NO: 12. In some embodiments, a $V_L$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in any one of the amino acid sequence of SEQ ID NO: 12. In some embodiments, the substitutions, insertions, or deletions occur in regions outside the CDRs (e.g., in the FRs). Optionally, the anti-HIV antibody comprises the $V_L$ sequence of SEQ ID NO: 12, including post-translational modifications of that sequence. In a particular embodiment, the $V_L$ comprises one, two or three CDRs selected from (a) CDR-L1 comprising the amino acid sequence of SEQ ID NO: 50; (b) CDR-L2 comprising the amino acid sequence of SEQ ID NO: 51; and (c) CDR-L3 comprising the amino acid sequence of SEQ ID NO: 52.

In one aspect, an anti-HIV antibody is provided, wherein the antibody comprises a $V_H$ as in any of the embodiments provided above, and a $V_L$ as in any of the embodiments provided above. In some embodiments, the antibody comprises a $V_H$ comprising the amino acid sequence of SEQ ID NO: 11, and a $V_L$ sequence in SEQ ID NO: 12, including post-translational modifications of those sequences.

AbV-7

In one aspect, the invention provides an anti-HIV antibody comprising at least one or both variable regions selected from (a) $V_H$ comprising the amino acid sequence of SEQ ID NO: 13 and (b) $V_L$ comprising the amino acid sequence of SEQ ID NO: 14.

In one aspect, the invention provides an anti-HIV antibody comprising at least one, two, three, four, five, or six CDRs selected from (a) CDR-H1 comprising the amino acid sequence of SEQ ID NO: 53; (b) CDR-H2 comprising the amino acid sequence of SEQ ID NO: 54; (c) CDR-H3 comprising the amino acid sequence of SEQ ID NO: 55; (d) CDR-L1 comprising the amino acid sequence of SEQ ID NO: 56; (e) CDR-L2 comprising the amino acid sequence of SEQ ID NO: 57; and (f) CDR-L3 comprising the amino acid sequence of SEQ ID NO: 58.

In one aspect, the invention provides an anti-HIV antibody comprising at least one, at least two, or all three $V_H$ CDR sequences selected from (a) CDR-H1 comprising the amino acid sequence of SEQ ID NO: 53; (b) CDR-H2 comprising the amino acid sequence of SEQ ID NO: 54; and (c) CDR-H3 comprising the amino acid sequence of SEQ ID NO: 55. In one aspect, the invention provides an anti-HIV antibody comprising at least one, at least two, or all three $V_H$ CDR sequences selected from (a) CDR-H1 comprising the amino acid sequence of SEQ ID NO: 53; (b) CDR-H2 comprising the amino acid sequence of SEQ ID NO: 54; and (c) CDR-H3 comprising the amino acid sequence of SEQ ID NO: 55; and (d) a $V_L$, H comprising the amino acid sequence of SEQ ID NO: 14. In one aspect, the invention provides an anti-HIV antibody comprising at least one, at least two, or all three $V_L$, CDR sequences selected from (a) CDR-L1 comprising the amino acid sequence of SEQ ID NO: 56; (b) CDR-L2 comprising the amino acid sequence of SEQ ID NO: 57 and (c) CDR-L3 comprising the amino acid sequence of SEQ ID NO: 58. In one aspect, the invention provides an anti-HIV antibody comprising at least one, at least two, or all three $V_L$, CDR sequences selected from (a) CDR-L1 comprising the amino acid sequence of SEQ ID NO: 56; (b) CDR-L2 comprising the amino acid sequence of SEQ ID NO: 57 and (c) CDR-L3 comprising the amino acid sequence of SEQ ID NO: 58; and (d) a $V_H$ comprising the amino acid sequence of SEQ ID NO: 13.

In one aspect, the invention provides an anti-HIV antibody comprising CDRs: (a) CDR-H1 comprising the amino acid sequence of SEQ ID NO: 53; (b) CDR-H2 comprising the amino acid sequence of SEQ ID NO: 54; (c) CDR-H3 comprising the amino acid sequence of SEQ ID NO: 55; (d) CDR-L1 comprising the amino acid sequence of SEQ ID NO: 56; (e) CDR-L2 comprising the amino acid sequence of SEQ ID NO: 57; and (f) CDR-L3 comprising the amino acid sequence of SEQ ID NO: 58.

In one aspect, an anti-HIV antibody comprises a $V_H$ sequence having at least 90%, 91%, 92%, 93%, 94%, 95%, 96%, 97%, 98%, 99%, or 100% sequence identity to the amino acid sequence of SEQ ID NO: 13. In some embodiments, a $V_H$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in the amino acid sequence of SEQ ID NO: 13. In some embodiments, substitutions, insertions, or deletions occur in regions outside the CDRs (e.g., in the FRs). Optionally, the anti-HIV antibody comprises the $V_H$ sequence of the amino acid sequence of SEQ ID NO: 13, including post-translational modifications of that sequence. In a particular embodiment, the $V_H$ comprises one, two or three CDRs selected from: (a) CDR-H1 comprising the amino acid sequence of SEQ ID NO: 53, (b) CDR-H2 comprising the amino acid sequence of SEQ ID NO: 54, and (c) CDR-H3 comprising the amino acid sequence of SEQ ID NO: 55.

In one aspect, an anti-HIV antibody is provided, wherein the antibody comprises a light chain variable domain ($V_L$) having at least 90%, 91%, 92%, 93%, 94%, 95%, 96%, 97%, 98%, 99%, or 100% sequence identity to the amino acid sequence of SEQ ID NO: 14. In some embodiments, a $V_L$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in any one of the amino acid sequence of SEQ ID NO: 14. In some embodiments, the substitutions, insertions, or deletions occur in regions outside the CDRs (e.g., in the FRs). Optionally, the anti-HIV antibody comprises the $V_L$ sequence of SEQ ID NO: 14, including post-translational modifications of that sequence. In a particular embodiment, the $V_L$ comprises one, two or three CDRs selected from (a) CDR-L1 comprising the amino acid sequence of SEQ ID NO: 56: 10; (b) CDR-L2 comprising the amino acid sequence of SEQ ID NO: 57; and (c) CDR-L3 comprising the amino acid sequence of SEQ ID NO: 58.

In one aspect, an anti-HIV antibody is provided, wherein the antibody comprises a $V_H$ as in any of the embodiments provided above, and a $V_L$ as in any of the embodiments provided above. In some embodiments, the antibody comprises a $V_H$ comprising the amino acid sequence of SEQ ID NO: 13, and a $V_L$ sequence in SEQ ID NO: 14, including post-translational modifications of those sequences.

AbV-8

In one aspect, the invention provides an anti-HIV antibody comprising the variable regions $V_H$ comprising the amino acid sequence of SEQ ID NO: 15. In one aspect, the invention provides an anti-HIV antibody comprising the variable regions $V_H$ comprising the amino acid sequence of SEQ ID NO: 15; and a paired $V_L$ region.

In one aspect, the invention provides an anti-HIV antibody comprising at least one, at least two, or all three $V_H$ CDR sequences selected from (a) CDR-H1 comprising the amino acid sequence of SEQ ID NO: 59; (b) CDR-H2 comprising the amino acid sequence of SEQ ID NO: 60; and (c) CDR-H3 comprising the amino acid sequence of SEQ ID NO: 61.

In one aspect, the invention provides an anti-HIV antibody comprising at least one, at least two, or all three $V_H$ CDR sequences selected from (a) CDR-H1 comprising the amino acid sequence of SEQ ID NO: 59; (b) CDR-H2 comprising the amino acid sequence of SEQ ID NO: 60; and (c) CDR-H3 comprising the amino acid sequence of SEQ ID NO: 61; and (b) a paired $V_L$ region.

In one aspect, the invention provides an anti-HIV antibody comprising at least one, at least two, or all three $V_H$ CDR sequences selected from (a) CDR-H1 comprising the amino acid sequence of SEQ ID NO: 59; (b) CDR-H2 comprising the amino acid sequence of SEQ ID NO: 60; and (c) CDR-H3 comprising the amino acid sequence of SEQ ID NO: 61; and at least one, at least two, or all three $V_L$ CDR sequences selected from a paired $V_L$ region.

In one aspect, the invention provides an anti-HIV antibody comprising CDRs: (a) CDR-H1 comprising the amino acid sequence of SEQ ID NO: 59; (b) CDR-H2 comprising the amino acid sequence of SEQ ID NO: 60; and (c) CDR-H3 comprising the amino acid sequence of SEQ ID NO: 61; and all three $V_L$ CDR sequences selected from a paired $V_L$ region.

In one aspect, an anti-HIV antibody comprises a $V_H$ sequence having at least 90%, 91%, 92%, 93%, 94%, 95%, 96%, 97%, 98%, 99%, or 100% sequence identity to the amino acid sequence of SEQ ID NO: 15. In some embodiments, a $V_H$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in the amino acid sequence of SEQ ID NO: 15. In some embodiments, substitutions, insertions, or deletions occur in regions outside the CDRs (e.g., in the FRs). Optionally, the anti-HIV antibody comprises the $V_H$ sequence of the amino acid sequence of SEQ ID NO: 15, including post-translational modifications of that sequence. In a particular embodiment, the $V_H$ comprises one, two or three CDRs selected from: (a) CDR-H1 comprising the amino acid sequence of SEQ ID NO: 59, (b) CDR-H2 comprising the amino acid sequence of SEQ ID NO: 60, and (c) CDR-H3 comprising the amino acid sequence of SEQ ID NO: 61.

In one aspect, an anti-HIV antibody is provided, wherein the antibody comprises a $V_H$ as in any of the embodiments provided above, and a $V_L$ as in any of the embodiments provided above. In some embodiments, the antibody comprises a $V_H$ comprising the amino acid sequence of SEQ ID NO: 15, and a paired $V_L$ sequence, including post-translational modifications of those sequences.

AbV-9

In one aspect, the invention provides an anti-HIV antibody comprising the variable regions $V_H$ comprising the amino acid sequence of SEQ ID NO: 16. In one aspect, the invention provides an anti-HIV antibody comprising the variable regions selected from (a) $V_H$ comprising the amino acid sequence of SEQ ID NO: 16 and (b) a $V_L$ comprising the amino acid sequence of SEQ ID NO: 4. In one aspect, the invention provides an anti-HIV antibody comprising the variable regions selected from (a) $V_H$ comprising the amino acid sequence of SEQ ID NO: 16 and (b) a $V_L$ comprising the amino acid sequence of SEQ ID NO: 65.

In one aspect, the invention provides an anti-HIV antibody comprising at least one, at least two, or all three $V_H$ CDR sequences selected from (a) CDR-H1 comprising the amino acid sequence of SEQ ID NO: 62; (b) CDR-H2 comprising the amino acid sequence of SEQ ID NO: 63; and (c) CDR-H3 comprising the amino acid sequence of SEQ ID NO: 64.

In one aspect, the invention provides an anti-HIV antibody comprising at least one, at least two, or all three $V_H$ CDR sequences selected from (a) CDR-H1 comprising the amino acid sequence of SEQ ID NO: 62; (b) CDR-H2 comprising the amino acid sequence of SEQ ID NO: 63; and (c) CDR-H3 comprising the amino acid sequence of SEQ ID NO: 64; and (d) a $V_L$ comprising the amino acid sequence of SEQ ID NO: 16.

In one aspect, the invention provides an anti-HIV antibody comprising at least one, at least two, or all three $V_H$ CDR sequences selected from (a) CDR-H1 comprising the amino acid sequence of SEQ ID NO: 62; (b) CDR-H2 comprising the amino acid sequence of SEQ ID NO: 63; and (c) CDR-H3 comprising the amino acid sequence of SEQ ID NO: 64; and (d) a $V_L$ comprising the amino acid sequence of SEQ ID NO: 65.

In one aspect, the invention provides an anti-HIV antibody comprising at least one, two, three, four, five, or six CDRs selected from (a) CDR-H1 comprising the amino acid sequence of SEQ ID NO: 62; (b) CDR-H2 comprising the amino acid sequence of SEQ ID NO: 63; (c) CDR-H3 comprising the amino acid sequence of SEQ ID NO: 64; (d) CDR-L1 comprising the amino acid sequence of SEQ ID NO: 26; (e) CDR-L2 comprising the amino acid sequence of SEQ ID NO: 27; and (f) CDR-L3 comprising the amino acid sequence of SEQ ID NO: 28.

In one aspect, the invention provides an anti-HIV antibody comprising CDRs: (a) CDR-H1 comprising the amino acid sequence of SEQ ID NO: 62; (b) CDR-H2 comprising the amino acid sequence of SEQ ID NO: 63; (c) CDR-H3 comprising the amino acid sequence of SEQ ID NO: 64; (d) CDR-L1 comprising the amino acid sequence of SEQ ID NO: 26; (e) CDR-L2 comprising the amino acid sequence of SEQ ID NO: 27; and (f) CDR-L3 comprising the amino acid sequence of SEQ ID NO: 28.

In one aspect, the invention provides an anti-HIV antibody comprising at least one, two, three, four, five, or six CDRs selected from (a) CDR-H1 comprising the amino acid sequence of SEQ ID NO: 62; (b) CDR-H2 comprising the amino acid sequence of SEQ ID NO: 63; (c) CDR-H3 comprising the amino acid sequence of SEQ ID NO: 64; (d) CDR-L1 comprising the amino acid sequence of SEQ ID NO: 66; (e) CDR-L2 comprising the amino acid sequence of SEQ ID NO: 67; and (f) CDR-L3 comprising the amino acid sequence of SEQ ID NO: 68.

In one aspect, the invention provides an anti-HIV antibody comprising CDRs: (a) CDR-H1 comprising the amino acid sequence of SEQ ID NO: 62; (b) CDR-H2 comprising the amino acid sequence of SEQ ID NO: 63; (c) CDR-H3 comprising the amino acid sequence of SEQ ID NO: 64; (d) CDR-L1 comprising the amino acid sequence of SEQ ID NO: 66; (e) CDR-L2 comprising the amino acid sequence of SEQ ID NO: 67; and (f) CDR-L3 comprising the amino acid sequence of SEQ ID NO: 68.

AbV-9a

In one aspect, an anti-HIV antibody comprises a $V_H$ sequence having at least 90%, 91%, 92%, 93%, 94%, 95%, 96%, 97%, 98%, 99%, or 100% sequence identity to the amino acid sequence of SEQ ID NO: 16. In some embodiments, a $V_H$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in the amino acid sequence of SEQ ID NO: 16. In some embodiments, substitutions, insertions, or deletions occur in regions outside the CDRs (e.g., in the FRs). Optionally, the anti-HIV antibody comprises the $V_H$ sequence of the amino acid sequence of SEQ ID NO: 16, including post-translational modifications of that sequence. In a particular embodiment, the $V_H$ comprises one, two or three CDRs selected from: (a) CDR-H1 comprising the amino acid sequence of SEQ ID NO: 62, (b) CDR-H2 comprising the amino acid sequence of SEQ ID NO: 63, and (c) CDR-H3 comprising the amino acid sequence of SEQ ID NO: 64.

In one aspect, an anti-HIV antibody is provided, wherein the antibody comprises a light chain variable domain ($V_L$) having at least 90%, 91%, 92%, 93%, 94%, 95%, 96%, 97%, 98%, 99%, or 100% sequence identity to the amino acid sequence of SEQ ID NO: 4. In some embodiments, a V1_, sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in any one of the amino acid sequence of SEQ ID NO: 4. In some embodiments, the substitutions, insertions, or deletions occur in regions outside the CDRs (e.g., in the FRs). Optionally, the anti-HIV antibody comprises the $V_L$ sequence of SEQ ID NO: 4, including post-translational modifications of that sequence. In a particular embodiment, the $V_L$ comprises one, two or three CDRs selected from (a) CDR-L1 comprising the amino acid sequence of SEQ ID NO: 26; (b) CDR-L2 comprising the amino acid sequence of SEQ ID NO: 27; and (c) CDR-L3 comprising the amino acid sequence of SEQ ID NO: 28.

In one aspect, an anti-HIV antibody is provided, wherein the antibody comprises a $V_H$ as in any of the embodiments provided above, and a $V_L$ as in any of the embodiments provided above. In some embodiments, the antibody comprises a $V_H$ comprising the amino acid sequence of SEQ ID NO: 16, and a $V_L$ sequence in SEQ ID NO: 4, including post-translational modifications of those sequences.

AbV-9b

In one aspect, an anti-HIV antibody comprises a $V_H$ sequence having at least 90%, 91%, 92%, 93%, 94%, 95%, 96%, 97%, 98%, 99%, or 100% sequence identity to the amino acid sequence of SEQ ID NO: 16. In some embodiments, a $V_H$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in the amino acid sequence of SEQ ID NO: 16. In some embodiments, substitutions, insertions, or deletions occur in regions outside the CDRs (e.g., in the FRs). Optionally, the anti-HIV antibody comprises the $V_H$ sequence of the amino acid sequence of SEQ ID NO: 16, including post-translational modifications of that sequence. In a particular embodiment, the $V_H$ comprises one, two or three CDRs selected from: (a) CDR-H1 comprising the amino acid sequence of SEQ ID NO: 62, (b) CDR-H2 comprising the amino acid sequence of SEQ ID NO: 63, and (c) CDR-H3 comprising the amino acid sequence of SEQ ID NO: 64.

In one aspect, an anti-HIV antibody is provided, wherein the antibody comprises a light chain variable domain ($V_L$) having at least 90%, 91%, 92%, 93%, 94%, 95%, 96%, 97%, 98%, 99%, or 100% sequence identity to the amino acid sequence of SEQ ID NO: 65. In some embodiments, a $V_L$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HIV antibody comprising that sequence retains the ability to bind to HIV. In some embodiments, a total of 1 to 10 amino acids have been substituted, inserted and/or deleted in any one of the amino acid sequence of SEQ ID NO: 65. In some embodiments, the substitutions, insertions, or deletions occur in regions outside the CDRs (e.g., in the FRs). Optionally, the anti-HIV antibody comprises the $V_L$ sequence of SEQ ID NO: 65, including post-translational modifications of that sequence. In a particular embodiment, the $V_L$ comprises one, two or three CDRs selected from (a) CDR-L1 comprising the amino acid sequence of SEQ ID NO: 66; (b) CDR-L2 comprising the amino acid sequence of SEQ ID NO: 67; and (c) CDR-L3 comprising the amino acid sequence of SEQ ID NO: 68.

In one aspect, an anti-HIV antibody is provided, wherein the antibody comprises a $V_H$ as in any of the embodiments provided above, and a $V_L$ as in any of the embodiments provided above. In some embodiments, the antibody comprises a $V_H$ comprising the amino acid sequence of SEQ ID NO: 16, and a $V_L$ sequence in SEQ ID NO: 68, including post-translational modifications of those sequences.

In some embodiments, the anti-HIV antibody is a human monoclonal antibody AbV-1. The amino acid sequences for the heavy and light chains of this antibody are presented in SEQ ID NOs: 1 and 2, respectively. In some embodiments, the anti-HIV antibody is a human monoclonal antibody AbV-2. The amino acid sequences for the heavy and light chains of this antibody are presented in SEQ ID NOs: 3 and 4, respectively. In some embodiments, the anti-HIV antibody is a human monoclonal antibody AbV-3. The amino acid sequences for the heavy and light chains of this antibody are presented in SEQ ID NOs: 5 and 6, respectively. In some embodiments, the anti-HIV antibody is a human monoclonal antibody AbV-4. The amino acid sequences for the heavy and light chains of this antibody are presented in SEQ ID NOs: 7 and 8, respectively. In some embodiments, the anti-HIV antibody is a human monoclonal antibody AbV-5. The amino acid sequences for the heavy and light chains of this antibody are presented in SEQ ID NOs: 9 and 10, respectively. In some embodiments, the anti-HIV antibody is a human monoclonal antibody AbV-6. The amino acid sequences for the heavy and light chains of this antibody are presented in SEQ ID NOs: 11 and 12, respectively. In some embodiments, the anti-HIV antibody is a human monoclonal antibody AbV-7. The amino acid sequences for the heavy and light chains of this antibody are presented in SEQ ID NOs: 13 and 14, respectively. In some embodiments, the anti-HIV antibody is a human monoclonal antibody AbV-8. The nucleic acid sequence for the heavy chain of this antibody is presented in SEQ ID NOs: 15. In some embodiments, the anti-HIV antibody is a human monoclonal antibody AbV-9a. The amino acid sequences for the heavy and light chains of this antibody are presented in SEQ ID NOs: 16 and 4, respectively. In some embodiments, the anti-HIV antibody is a human monoclonal antibody AbV-9b. The amino acid sequences for the heavy and light chains of this antibody are presented in SEQ ID NOs: 16 and 65, respectively.

In some embodiments, the anti-HIV antibody is a chimeric antibody derived from any of the above mentioned human antibodies. In some embodiments, the anti-HIV antibody is a humanized antibody. In some embodiments, the anti-HIV antibody is a human antibody.

In a further aspect, an anti-HIV antibody according to any of the above embodiments may incorporate any of the features, singly or in combination, as described below.

Antibody Properties
Mutation Frequency

The antibodies of the invention can comprise a heavy chain sequence with a mutation frequency of at least about 5%, 6%, 7%, 8%, 9%, 10%, 11%, 12%, 13%, 14%, 15%, 16%, 17%, 18%, 19%, or 20%, or higher from a germline sequence. The antibodies of the invention can The antibodies of the invention can comprise a CDR3 region that is a light chain sequence with a mutation frequency of at least about 5%, 6%, 7%, 8%, 9%, 10%, 11%, 12%, 13%, 14%, 15%, 16%, 17%, 18%, 19%, or 20%, or higher from a germline sequence. The antibodies of the invention can comprise a heavy chain and a light chain sequence with a mutation frequency of at least about 5%, 6%, 7%, 8%, 9%, 10%, 11%, 12%, 13%, 14%, 15%, 16%, 17%, 18%, 19%, or 20%, or higher from a germline sequence. The antibodies of the invention can comprise a $V_H$ region from a $V_H$ family selected from the group consisting of any one of $V_H$ family 4-59.

Heavy and Light Chain Lengths

The antibodies of the invention can comprise a CDR3 region that is a length of at least about 10, 11, 12, 13, 14, 15, 16, 17, 18, 19, 20, 21, 22, 23, 24, 25, 26, 27, 28, 29, or 30 amino acids in length. The antibodies of the invention can comprise a CDR3 region that is at least about 18 amino acids in length.

The antibodies of the invention can comprise a deletion at an end of a light chain. The antibodies of the invention can comprise a deletion of 3 or more amino acids at an end of the light chain. The antibodies of the invention can comprise a deletion of 7 or less amino acids at an end of the light chain. The antibodies of the invention can comprise a deletion of 3, 4, 5, 6, or 7 amino acids at an end of the light chain.

The antibodies of the invention can comprise an insertion in a light chain. The antibodies of the invention can comprise an insertion of 1, 2, 3, 4, 5, 6, 7, 8, 9, or 10, or more amino acids in the light chain. The antibodies of the invention can comprise an insertion of 3 amino acids in the light chain.

Affinity

Affinity is the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($k_d$). Affinity can be measured by any of a number of known methods, including those commonly used and/or those described herein. Specific illustrative and exemplary embodiments for measuring binding affinity are described in the following.

In some embodiments, an antibody provided herein has a dissociation constant ($K_D$) of about 1 µM, 100 nM, 10 nM, 5 nM, 2 nM, 1 nM, 0.5 nM, 0.1 nM, 0.05 nM, 0.01 nM, or 0.001 nM or less (e.g., $10^{-8}$M or less, e.g., from $10^{-8}$M to $10^{-13}$M, e.g., from $10^{-9}$M to $10^{-13}$M) for the antibody target. The antibody target can be an HIV target. The antibody target can be an HIV-1 target. The antibody target can be an HIV-2 target. The antibody target can be an HIV-1 group M target. The antibody target can be an HIV-1 group N target, HIV-1 group O target, and/or HIV-1 P target. The antibody target can be an HIV Glade A (including A1 and/or A2), B, C, D, E, F (including F1 and/or F2), G, H, I, J, K, or any combination, subtype, or recombinant derivative (including circulating recombinant form (CRF)) thereof. Another aspect of the invention provides for an anti-HIV antibody with an increased affinity for its HIV target, for example, an affinity matured anti-HIV antibody. An affinity matured antibody is an antibody with one or more alterations in one or more hypervariable regions (HVRs), compared to a parent antibody which does not possess such alterations, such alterations resulting in an improvement in the affinity of the antibody for antigen. These antibodies can bind to HIV with a $K_D$ of about $5\times10^{-9}$M, $2\times10^{-9}$M, $1\times10^{-9}$M, $5\times10^{-1}$ $2\times10^{-9}$M, $1\times10^{-10}$M, $5\times10^{-11}$M, $1\times10^{-11}$M, $5\times10^{-12}$M, $1\times10^{-12}$M, or less. In some embodiments, the invention provides an anti-HIV antibody which has an increased affinity of at least 1.5 fold, 2 fold, 2.5 fold, 3 fold, 4 fold, 5 fold, 10 fold, 20 fold or greater as compared to a germline anti-HIV antibody containing the heavy chain sequence of SEQ ID NO: 69, the light chain sequence of SEQ ID NO: 70, or both. In other embodiments, an antibody is provided that competes for binding to the same epitope as an anti-HIV antibody as described herein. In some embodiments, the antibody that binds to the same epitope, and/or competes for binding to the same epitope as an anti-HIV antibody exhibits effector function activities, such as, for example, Fc-mediated cellular cytotoxicity, including ADCC activity.

$K_D$ can be measured by any suitable assay. For example, $K_D$ can be measured by a radiolabeled antigen binding assay (RIA) (See, e.g., Chen et al., J. Mol. Biol. 293:865-881 (1999); Presta et al., Cancer Res. 57:4593-4599 (1997)). For example, $K_D$ can be measured using surface plasmon resonance assays (e.g., using a BIACORE®-2000 or a BIACOREe-3000).

Antibody Fragments

An antibody fragment comprises a portion of an intact antibody, such as the antigen binding or variable region of the intact antibody. In a further aspect of the invention, an anti-HIV antibody according to any of the above embodiments is a monoclonal antibody, including a chimeric, humanized or human antibody. Antibody fragments include, but are not limited to, Fab, Fab', Fab'-SH, F(ab')$_2$, Fv, diabody, linear antibodies, multispecific formed from antibody fragments antibodies and scFv fragments, and other fragments described below. In another embodiment, the antibody is a full length antibody, e.g., an intact IgG1 antibody or other antibody class or isotype as described herein. (See, e.g., Hudson et al. Nat. Med. 9:129-134 (2003); Pluckthiin, The Pharmacology of Monoclonal Antibodies, vol. 113, pp. 269-315 (1994); Hollinger et al., Proc. Natl. Acad. Sci. USA 90: 6444-6448 (1993); WO93/01161; and U.S. Pat. Nos. 5,571,894, 5,869,046, 6,248,516, and 5,587,458). A full length antibody, intact antibody, or whole antibody is an antibody having a structure substantially similar to a native antibody structure or having heavy chains that contain an Fc region as defined herein. Antibody fragments can be made by various techniques, including but not limited to proteolytic digestion of an intact antibody as well as production by recombinant host cells (e.g., *E. coli* or phage), as described herein.

An Fv is the minimum antibody fragment that contains a complete antigen-recognition and antigen-binding site. This fragment contains a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable region (or half of an Fv comprising only three CDRs specific for an antigen) has the ability to recognize and bind antigen, although at a lower affinity than the entire binding site.

A single-chain Fv (sFv or scFv) is an antibody fragment that comprises the $V_H$ and $V_L$ antibody domains connected into a single polypeptide chain. The sFv polypeptide can further comprise a polypeptide linker between the $V_H$ and $V_L$ domains that enables the sFv to form the desired structure for antigen binding. (See, e.g., Pluckthun in The Pharmacology of Monoclonal Antibodies, vol. 113, Rosenburg and Moore eds., Springer-Verlag, New York, pp. 269-315 (1994); Borrebaeck 1995, infra. In some embodiments, the sFv can be present in a chimeric antigen receptor (CAR).

A diabody is a small antibody fragment prepared by constructing an sFv fragment with a short linker (about 5-10 residues) between the $V_H$ and $V_L$ domains such that interchain but not intra-chain pairing of the V domains is achieved, resulting in a bivalent fragment. Bispecific diabodies are heterodimers of two crossover sFv fragments in which the $V_H$ and $V_L$ domains of the two antibodies are present on different polypeptide chains. (See, e.g., EP 404,097; WO 93/11161; and Hollinger et al, Proc. Natl. Acad. Sci. USA, 90:6444-6448 (1993)).

Domain antibodies (dAbs), which can be produced in fully human form, are the smallest known antigen-binding fragments of antibodies, ranging from about 11 kDa to about 15 kDa. DAbs are the robust variable regions of the heavy and light chains of immunoglobulins ($V_H$ and $V_L$, respectively). They are highly expressed in microbial cell culture, show favorable biophysical properties including, for example, but not limited to, solubility and temperature stability, and are well suited to selection and affinity maturation by in vitro selection systems such as, for example, phage display. DAbs are bioactive as monomers and, owing to their small size and inherent stability can be formatted into larger molecules to create drugs with prolonged serum half-lives or other pharmacological activities. (See, e.g., WO9425591 and US20030130496).

Fv and sFv are species with intact combining sites that are devoid of constant regions. Thus, they are suitable for reduced nonspecific binding during in vivo use. sFv fusion proteins can be constructed to yield fusion of an effector protein at either the amino or the carboxy terminus of an sFv. The antibody fragment also can be a linear antibody. (See, e.g., U.S. Pat. No. 5,641,870). Such linear antibody fragments can be monospecific or bispecific.

Chimeric Antigen Receptors (CARs)

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) *PLoS ONE* 8(4): e61338; Turtle et al., *Curr. Opin. Immunol.*, 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No.: WO/2014055668 Al. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, *Nature Reviews Clinical Oncology*, 10, 267-276 (2013); Wang et al. (2012) *J. Immunother*. 35(9): 689-701; and Brentj ens et al., *Sci Transl Med.* 2013 5(177). See also WO2014031687, U.S. Pat. Nos. 8,339,645, 7,446,179, US 2013/0149337, U.S. Pat. Nos. 7,446,190, 8,389,282. The chimeric receptors, such as CARs, generally include an extracellular antigen binding domain, such as a portion of an antibody molecule, generally a variable heavy ($V_H$) chain region and/or variable light ($V_L$) chain region of the antibody, e.g., an scFv antibody fragment.

In some embodiments, a chimeric antigen receptor (CAR) can comprise an intracellular domain comprising an intracellular domain of a T cell receptor, and an extracellular portion comprising an antigen binding portion of an antibody, e.g., an sFv of an antibody. Generally, a chimeric receptor (e.g., a CAR) comprises a linker or spacer domain between the antigen binding portion and the transmembrane domain. In some embodiments, the linker or spacer is derived from an immunoglobulin hinge region. In some embodiments, a nucleic acid encoding a CAR construct, in some embodiments a CAR vector, in addition to encoding an intracellular domain comprising an intracellular domain of a T cell receptor, and an extracellular portion comprising an antigen binding portion of an antibody, e.g., an sFv of an antibody, can comprise a promoter. For example, a promoter can be a synthetic promoter that contins a U3 region of a modified MoMuLV LTR with myleloproliferative sarcoma virus enhancer. In other embodiments, a promoter can be an EFla promoter or an EF1 promoter. In some embodiments, a CAR can comprise an intracellular domain comprising a co-stimulatory domain and an intracellular domain of a T cell receptor, and an extracellular portion comprising an antibody, such as one or more antibodies provided herein, which may be a single-chain antibody or fragment thereof. In some embodiments, the antibody is or comprises an sFv or an scFv. In some embodiments, the CAR may further include additional extracellular portion(s), such as a spacer and/or hinge region.

In any of the above embodiments, the antibody within the chimeric molecule, e.g., chimeric receptor, e.g., CAR, such as the sFv can comprise a $V_H$ domain and a $V_L$ domain of an antibody. For example, an sFv can comprise a $V_H$ domain from any one of AbV-1, AbV-2, AbV-3, AbV-4, AbV-5, AbV-6, AbV-7, AbV-8, AbV-9, AbV-9a, or AbV-9b in combination with a $V_L$ domain from any one of Ab-V1, AbV-2, AbV-3, AbV-4, AbV-5, AbV-6, AbV-7, AbV-8, AbV-9, AbV-9a, or Abv-9b. For example, an sFv can be created by the synthesis of codon-optimized sequences for the heavy and light chains separated by one of a number of linkers.

In some aspects, the linkers rich in glycine and serine (and/or threonine) include at least 80%, 85%, 90%, 91%, 92%, 93%, 94%, 95%, 96%, 97%, 98%, or 99% such amino acid(s). In some embodiments, they include at least at or about 50%, 55%, 60%, 70%, or 75%, glycine, serine, and/or threonine. In some embodiments, the linker is comprised substantially or entirely of glycine, serine, and/or threonine. The linkers generally are from about 5 amino acids to about 50 amino acids in length, typically between, at, or about 10 amino acids and at or about 30 amino acids, e.g., 10, 11, 12, 13, 14, 15, 16, 17, 18, 19, 20, 21, 22, 23, 24, 25, 26, 27, 28, 29, or 30 amino acids, and in some examples between 10 amino acids and 25 amino acids in length. Exemplary linkers include linkers having various numbers of repeats of the sequence GGGGS (4GS) (SEQ ID NO: 71) or GGGS (3GS) (SEQ ID NO: 72), such as from 2, 3, 4, to 5 repeats of such a sequence. Exemplary linkers include those having or consisting of a GGGGSGGGGSGGGGS (SEQ ID NO: 73). Exemplary linkers further include those having or consisting of the sequence GSTSGSGKPGSGEGSTKG (SEQ ID NO: 74).

In some embodiments, the intracellular signaling domain includes intracellular signaling domains of costimulatory receptors such as CD28, CD137 (4-1 BB), OX40, and/or ICOS. In some embodiments, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCRζ, FcRγ, FcRβ, CD3γ, CD3δ, CD3ε, CD8, CD22, CD79a, CD79b, and CD66d. In some embodiments, cytoplasmic signaling molecule(s) in the CAR contain(s) a cytoplasmic signaling domain, portion thereof, or sequence derived from CD3ζ.

An exemplary CAR vector (including a nucleic acid encoding a CAR) can be transfected into T cells. The T cells can be CD8$^+$ T cells. In some embodiments, CD8$^+$ T cells that were transfected and express the CAR can recognize infected cells for proliferation, killing, and/or suppression of viral replication. In other embodiments, the T cell transfected with a CAR can be a CD4$^+$ T cell. In some embodiments, CAR modified CD4$^+$ T cells can be further modified such that they no longer express CD4. In some embodiments, a T cell tranfected with a CAR can be further modified to lack coreceptors involved in HIV infection, such as CCR2b, CCR3, CXCR4, and/or CCR5. For example, T cells can be transfected with reagents, such as siRNA, to decrease or knock-down expression of one or more coreceptors involved in HIV infection, such as CCR2b, CCR3, CXCR4, and/or CCR5. In some embodiments, the expression of one or more of these coreceptors involved in HIV infection can be decreased or knocked-down by a targeted genome editing tool, such as a zinc finger nuclease (ZFN), a trancription activator-like effector nuclease (TALEN), the CRISPR/Cas system, RNA guided endo nucleases, and/or engineered meganuclease re-engineered homing endonuclease.

Chimeric and Humanized Antibodies

In some embodiments, an antibody provided herein is a chimeric antibody (See, e.g., U.S. Pat. No. 4,816,567; and Morrison et al., Proc. Natl. Acad. Sci. USA, 81:6851-6855 (1984)). A chimeric antibody generally refers to an antibody in which a portion of the heavy and/or light chain is derived from a particular source or species, while the remainder of the heavy and/or light chain is derived from a different source or species. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments, the antibody is a humanized antibody (See, e.g., Almagro and Fransson, Front. Biosci.13: 1619-1633 (2008); Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982, 321, and 7,087,409; Kashmiri et al., Methods 36:25-34 (2005); Padlan, Mol. Immunol.28:489-498 (1991); Dall'Acqua et al., Methods 36:43-60 (2005); Osbourn et al., Methods 36:61-68 (2005); and Klimka et al., Br. J. Cancer, 83:252-260 (2000)).

A non-human antibody can be humanized to reduce immunogenicity to humans, while retaining the specificity and affinity of the parental non-human antibody. A humanized antibody can comprise one or more variable domains comprising one or more CDRs, or portions thereof, derived from a non-human antibody. A humanized antibody can comprise one or more variable domains comprising one or more FRs, or portions thereof, derived from human antibody sequences. A humanized antibody can optionally comprise at least a portion of a human constant region. In some embodiments, one or more FR residues in a humanized antibody are substituted with corresponding residues from a non-human antibody (e.g., the antibody from which the CDR residues are derived), e.g., to restore or improve antibody specificity or affinity.

Human framework regions that may be used for humanization include but are not limited to: framework regions selected using a "best-fit" method; framework regions derived from the consensus sequence of human antibodies of a particular subgroup of light or heavy chain variable regions; human mature (somatically mutated) framework regions or human germline framework regions; and framework regions derived from screening FR libraries (See, e.g., Sims et al. J. Immunol. 151:2296 (1993); Carter et al. Proc. Natl. Acad. Sci. USA, 89:4285 (1992); Presta et al. J. Immunol, 151:2623 (1993); Baca et al., J. Biol. Chem. 272:10678-10684 (1997); and Rosok et al., J. Biol. Chem. 271:22611-22618 (1996)).

Human Antibodies

In some embodiments, an antibody provided herein is a human antibody. Human antibodies can be produced using various known techniques (See, e.g., van Dijk and van de Winkel, Curr. Opin. Pharmacol. 5: 368-74 (2001); and Lonberg, Curr. Opin. Immunol. 20:450-459 (2008)). Human antibodies in some aspects may be prepared by administering an immunogen (e.g., an HIV immunogen) to a transgenic animal that has been modified to produce intact human antibodies or intact antibodies with human variable regions in response to antigenic challenge. (See, e.g., Lonberg, Nat. Biotech. 23:1117-1125 (2005); U.S. Pat. Nos. 6,075,181, 6,150,584, 5,770,429, and 7,041,870; and U.S. Pat. App. Pub. No. US 2007/0061900). Human variable regions from intact antibodies generated by such animals may be further modified, e.g., by combining with a different human constant region.

Human antibodies can in some aspects also be made by hybridoma-based methods. For example, human antibodies can be produced from human myeloma and mouse-human heteromyeloma cell lines, using human B-cell hybridoma technology, and other methods (See, e.g., Kozbor J. Immunol., 133: 3001 (1984); Brodeur et al., Monoclonal Antibody Production Techniques and Applications, pp. 51-63 (1987); Boerner et al., J. Immunol., 147: 86 (1991); Li et al., Proc. Natl. Acad., 103:3557-3562 (2006); U.S. Pat. No. 7,189,826; Ni, Xiandai Mianyixue, 26(4):265-268 (2006); Vollmers and Brandlein, Histology and Histopathology, 20(3): 927-937 (2005); and Vollmers and Brandlein, Methods and Findings in Experimental and Clinical *Pharmacology*, 27(3): 185-91 (2005)). Human antibodies may also be generated by isolating Fv clone variable domain sequences selected from human-derived phage display libraries. Such variable domain sequences may then be combined with a desired human constant domain.

Library-Derivation

Antibodies may be isolated by screening combinatorial libraries for antibodies with the desired activity or activities. (See, e.g., in Hoogenboom et al., *Methods in Molecular Biology* 178:1-37 (2001); McCafferty et al., Nature 348:552-554; Clackson et al., *Nature* 352: 624-628 (1991); Marks et al., J. Mol. Biol. 222: 581-597 (1992); Marks and Bradbury, Methods in Molecular Biology 248:161-175 (2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004)). Repertoires of $V_H$ and $V_L$ genes can be cloned separately (e.g., by PCR) and recombined randomly in libraries (e.g., phage libraries), and screened (See, e.g., Winter et al., Ann. Rev. Immunol., 12: 433-455 (1994)). Alternatively, the naive repertoire can be cloned (e.g., from human) to provide a single source of antibodies to a wide range of non-self and also self-antigens without any immunization (See, e.g., Griffiths et al., EMBO J, 12: 725-734 (1993). Alternatively, naive libraries can be synthetically made by cloning unrearranged V-gene segments from stem cells, and encoding the CDR3 regions using random primers or to rearrange the V-gene segments in vitro (See, e.g., Hoogenboom and Winter, J. Mol. Biol., 227: 381-388 (1992); U.S. Pat. No. 5,750,373, and U.S. Pat. Pub. Nos. US 2005/0079574, US 2005/0119455, US 2005/0266000, US 2007/0117126, US 2007/0160598, US 2007/0237764, US 2007/0292936, and US 2009/0002360. Antibodies or antibody fragments isolated from human antibody libraries are considered human antibodies or human antibody fragments herein.

Multispecificity

In some embodiments, an antibody provided herein is a multispecific antibody, e.g., a bispecific antibody. Multispecific antibodies are generally monoclonal antibodies that have binding specificities for at least two different sites (See, e.g., U.S. Pat. Pub. No. US 2008/0069820). In some embodiments, one of the binding specificities is for HIV and the other is for any other antigen. In some embodiments, bispecific antibodies may bind to two different epitopes of HIV. Bispecific antibodies may also be used to localize cytotoxic agents to cells infected with HIV. Bispecific antibodies can be prepared as full length antibodies or antibody fragments.

Exemplary techniques for making multispecific antibodies include recombinant co-expression of two immunoglobulin heavy chain-light chain pairs having different specificities, engineering electrostatic steering effects for making antibody Fc-heterodimeric molecules, cross-linking two or more antibodies or fragments, using leucine zippers to produce bi-specific antibodies, using "diabody" technology for making bispecific antibody fragments, using single-chain Fv (sFv) dimers, preparing trispecific antibodies, and "knob-in-hole" engineering (See, e.g., Milstein and Cuello, Nature 305: 537 (1983); WO09/089004A1; WO93/08829; Traunecker et al., EMBO J. 10: 3655 (1991); U.S. Pat. Nos. 4,676,980 and 5,731,168; Brennan et al., Science, 229: 81 (1985); Kostelny et al., J. Immunol., 148(5):1547-1553 (1992); Hollinger et al., Proc. Natl. Acad. Sci. USA, 90:6444-6448 (1993); Gruber et al., J. Immunol., 152:5368 (1994)); and Tutt et al. J. Immunol. 147: 60 (1991)). Engineered antibodies with three or more functional antigen binding sites are also included (See, e.g., US 2006/0025576).

Variants

In some embodiments, amino acid sequence variants of the antibodies provided herein are contemplated. A variant typically differs from a polypeptide specifically disclosed herein in one or more substitutions, deletions, additions and/or insertions. Such variants can be naturally occurring or can be synthetically generated, for example, by modifying one or more of the above polypeptide sequences of the invention and evaluating one or more biological activities of the polypeptide as described herein and/or using any of a number of known techniques. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Substitution, Insertion, and Deletion Variants In some embodiments, antibody variants having one or more amino acid substitutions are provided. Sites of interest for mutagenesis by substitution include the CDRs and FRs. Amino acid substitutions may be introduced into an antibody of interest and the products screened for a desired activity, e.g., retained/improved antigen binding, decreased immunogenicity, or improved ADCC or CDC.

| Original Residue | Exemplary Conserved Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |

| Original Residue | Exemplary Conserved Substitutions |
| --- | --- |
| Trp (W) | Tyr; Phe |
| Tyr (Y) | Trp; Phe; Thr; Ser |
| Val (V) | Ile; Leu; Met; Phe; Ala; Norleucine |

Hydrophobic amino acids include: Norleucine, Met, Ala, Val, Leu, and Ile. Neutral hydrophilic amino acids include: Cys, Ser, Thr, Asn, and Gln. Acidic amino acids include: Asp and Glu. Basic amino acids include: His, Lys, and Arg. Amino acids with residues that influence chain orientation include: Gly and Pro. Aromatic amino acids include: Trp, Tyr, and Phe.

In some embodiments, substitutions, insertions, or deletions may occur within one or more CDRs, wherein the substitutions, insertions, or deletions do not substantially reduce antibody binding to antigen. For example, conservative substitutions that do not substantially reduce binding affinity may be made in CDRs. Such alterations may be outside of CDR "hotspots" or SDRs. In some embodiments of the variant $V_H$ and $V_L$ sequences, each CDR either is unaltered, or contains no more than one, two or three amino acid substitutions.

Alterations (e.g., substitutions) may be made in CDRs, e.g., to improve antibody affinity. Such alterations may be made in CDR encoding codons with a high mutation rate during somatic maturation (See, e.g., Chowdhury, Methods Mol. Biol. 207:179-196 (2008)), and the resulting variant can be tested for binding affinity. Affinity maturation (e.g., using error-prone PCR, chain shuffling, randomization of CDRs, or oligonucleotide-directed mutagenesis) can be used to improve antibody affinity (See, e.g., Hoogenboom et al. in Methods in Molecular Biology 178:1-37 (2001)). CDR residues involved in antigen binding may be specifically identified, e.g., using alanine scanning mutagenesis or modeling (See, e.g., Cunningham and Wells Science, 244:1081-1085 (1989)). CDR-H3 and CDR-L3 in particular are often targeted. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions and deletions include amino- and/or carboxyl-terminal fusions ranging in length from one residue to polypeptides containing a hundred or more residues, as well as intrasequence insertions and deletions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody. Examples of intrasequence insertion variants of the antibody molecules include an insertion of 3 amino acids in the light chain. Examples of terminal deletions include an antibody with a deletion of 7 or less amino acids at an end of the light chain.

Glycosylation Variants

In some embodiments, the antibodies are altered to increase or decrease their glycosylation (e.g., by altering the amino acid sequence such that one or more glycosylation sites are created or removed). A carbohydrate attached to an Fc region of an antibody may be altered. Native antibodies from mammalian cells typically comprise a branched, biantennary oligosaccharide attached by an N-linkage to Asn297 of the CH2 domain of the Fc region (See, e.g., Wright et al. TIBTECH 15:26-32 (1997)). The oligosaccharide can be various carbohydrates, e.g., mannose, N-acetyl glucosamine (GlcNAc), galactose, sialic acid, fucose attached to a GlcNAc in the stem of the biantennary oligosaccharide structure. Modifications of the oligosaccharide in an antibody can be made, for example, to create antibody variants with certain improved properties. Antibody glycosylation variants can have improved ADCC and/or CDC function.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn297 (See, e.g., WO 08/077546). Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants can have improved ADCC function (See, e.g., Pat. Pub. Nos. US 2003/0157108; US 2004/0093621; US 2003/0157108; WO00/61739; WO01/29246; US 2003/0115614; US 2002/0164328; 2004/0093621; US 2004/0132140; US 2004/0110704; US 2004/0110282; US 2004/0109865; WO03/085119; WO03/084570; WO05/035586; WO05/035778; WO05/053742; WO02/031140; Okazaki et al. *J. Mol. Biol.* 336:1239-1249 (2004); and Yamane-Ohnuki et al. Biotech. Bioeng. 87: 614 (2004)). Cell lines, e.g., knockout cell lines and methods of their use can be used to produce defucosylated antibodies, e.g., Lec13 CHO cells deficient in protein fucosylation and alpha-1,6-fucosyltransferase gene (FUT8) knockout CHO cells (See, e.g., Ripka et al. Arch. Biochem. Biophys. 249:533-545 (1986); Yamane-Ohnuki et al. Biotech. Bioeng. 87: 614 (2004); Kanda, Y. et al., Biotechnol. Bioeng., 94(4):680-688 (2006); WO03/085107; EP 1176195A1, WO04/056312; WO04/057002; WO03/084570; WO03/085119; WO03/05691;4 WO04/024927; and U.S. Pat. Pub. Nos. US 2003/0157108; US 2003/0115614, US 2004/093621, US 2004/110282, US 2004/110704, and US 2004/132140). Other antibody glycosylation variants are also included (See, e.g., U.S. Pat. No. 6,602,684; Pat. Pub. No. US 2005/0123546; WO03/011878; WO97/30087; WO98/58964; and WO99/22764.

Accordingly, the anti-HIV antibodies of the present invention can be produced by a host cell with one or more of exogenous and/or high endogenous glycosyltransferase activities. Genes with glycosyltransferase activity include β(1,4)-N-acetylglucosaminyltransferase III (GnTII), α-mannosidase II (ManII), β(1,4)-galactosyltransferase (GalT), β(1,2)-N-acetylglucosaminyltransferase I (GnTI), and β(1,2)-N-acetylglucosaminyltransferase II (GnTII). The glycotranferases can comprise a fusion comprising a Golgi localization domain (See, e.g., Lifely et al., Glycobiology 318:813-22 (1995); Schachter, Biochem. Cell Biol. 64:163-81 (1986); U.S. Prov. Pat. App. Nos. 60/495,142 and 60/441,307; Pat. Pub. Nos. US 2003/0175884 and US 2004/0241817; and WO04/065540). In some embodiments, an anti-HIV antibody can be expressed in a host cell comprising a disrupted or deactivated glycosyltransferase gene. Accordingly, in some embodiments, the present invention is directed to a host cell comprising (a) an isolated nucleic acid comprising a sequence encoding a polypeptide having a glycosyltransferase activity; and (b) an isolated polynucleotide encoding an anti-HIV antibody of the present invention that binds human HIV. In a particular embodiment, the modified anti-HIV antibody produced by the host cell has an IgG constant region or a fragment thereof comprising the Fc region. In another particular embodiment the anti-HIV antibody is a humanized antibody or a fragment thereof comprising an Fc region. An isolated nucleic acid is a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

Anti-HIV antibodies with altered glycosylation produced by the host cells of the invention can exhibit increased Fc receptor binding affinity (e.g., increased binding to a Fcγ activating receptor, such as the FcγRIIIa receptor) and/or increased effector function. The increased effector function can be an increase in one or more of the following: increased antibody-dependent cellular cytotoxicity, increased antibody-dependent cellular phagocytosis (ADCP), increased cytokine secretion, increased immune-complex-mediated antigen uptake by antigen-presenting cells, increased Fc-mediated cellular cytotoxicity, increased binding to NK cells, increased binding to macrophages, increased binding to polymorphonuclear cells (PMNs), increased binding to monocytes, increased crosslinking of target-bound antibodies, increased direct signaling inducing apoptosis, increased dendritic cell maturation, and increased T cell priming. Accordingly, in one aspect, the present invention provides glycoforms of an anti-HIV antibody having increased effector function as compared to the anti-HIV antibody that has not been glycoengineered. (See, e.g., Tang et al., J. Immunol. 179:2815-2823 (2007)).

The present invention is also directed to a method for producing an anti-HIV antibody of the present invention having modified oligosaccharides, comprising (a) culturing a host cell engineered to express at least one nucleic acid encoding a polypeptide having glycosyltransferase activity under conditions which permit the production of an anti-HIV antibody according to the present invention, wherein said polypeptide having glycosyltransferase activity is expressed in an amount sufficient to modify the oligosaccharides in the Fc region of said anti-HIV antibody produced by said host cell; and (b) isolating said anti-HIV antibody. In another embodiment, there are two polypeptides having glycosyltransferase activity. The anti-HIV antibodies produced by the methods of the present invention can have increased Fc receptor binding affinity and/or increased effector function.

In some embodiments, the percentage of bisected N-linked oligosaccharides in the Fc region of the anti-HIV antibody is at least about 10% to about 100%, specifically at least about 50%, more specifically, at least about 60%, at least about 70%, at least about 80%, or at least about 90-95% of the total oligosaccharides. In yet another embodiment, the antibody produced by the methods of the invention has an increased proportion of nonfucosylated oligosaccharides in the Fc region as a result of the modification of its oligosaccharides by the methods of the present invention. In some embodiments, the percentage of nonfucosylated oligosaccharides is at least about 20% to about 100%, specifically at least about 50%, at least about 60% to about 70%, and more specifically, at least about 75%. The nonfucosylated oligosaccharides may be of the hybrid or complex type. In yet another embodiment, the antibody produced by the methods of the invention has an increased proportion of bisected oligosaccharides in the Fc region as a result of the modification of its oligosaccharides by the methods of the present invention. In some embodiments, the percentage of bisected oligosaccharides is at least about 20% to about 100%, specifically at least about 50%, at least about 60% to about 70%, and more specifically, at least about 75%.

In another embodiment, the present invention is directed to an anti-HIV antibody engineered to have increased effector function and/or increased Fc receptor binding affinity, produced by the methods of the invention. In some embodiments, the antibody is an intact antibody. In some embodiments, the antibody is an antibody fragment containing the Fc region, or a fusion protein that includes a region equivalent to the Fc region of an immunoglobulin.

In one aspect, the present invention provides host cell expression systems for the generation of the antibodies of the present invention having modified glycosylation patterns. In particular, the present invention provides host cell systems for the generation of glycoforms of the antibodies of the present invention having an improved therapeutic value. Therefore, the invention provides host cell expression systems selected or engineered to express a polypeptide having a glycosyltransferase activity.

Generally, any type of cultured cell line, including the cell lines discussed above, can be used as a background to engineer the host cell lines of the present invention. In some embodiments, CHO cells, BHK cells, NSO cells, SP2/0 cells, YO myeloma cells, P3X63 mouse myeloma cells, PER cells, PER.C6 cells or hybridoma cells, other mammalian cells, yeast cells, insect cells, or plant cells are used as the background cell line to generate the engineered host cells of the invention.

The host cells which contain the coding sequence of an antibody of the invention and which express the biologically active gene products may be identified by at least four general approaches; (a) DNA-DNA or DNA-RNA hybridization; (b) the presence or absence of "marker" gene functions; (c) assessing the level of transcription as measured by the expression of the respective mRNA transcripts in the host cell; and (d) detection of the gene product as measured by immunoassay or by its biological activity.

Fc Region Variants

In some embodiments, one or more amino acid modifications may be introduced into the Fc region of an antibody provided herein, thereby generating an Fc region variant. An Fc region herein is a C-terminal region of an immunoglobulin heavy chain that contains at least a portion of the constant region. An Fc region includes native sequence Fc regions and variant Fc regions. The Fc region variant may comprise a human Fc region sequence (e.g., a human IgG1, IgG2, IgG3 or IgG4 Fc region) comprising an amino acid modification (e.g., a substitution) at one or more amino acid positions.

In some embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. Non-limiting examples of in vitro assays to assess ADCC activity of a molecule of interest is described in U.S. Pat. Nos. 5,500,362 and 5,821,337. Alternatively, non-radioactive assays methods may be employed (e.g., ACTI™ and CytoTox 96® non-radioactive cytotoxicity assays). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model (See, e.g., Clynes et al. Proc. Nat'l Acad. Sci. USA 95:652-656 (1998). C1q binding assays may also be carried out to confirm that the antibody is able or unable bind C1q and hence contains or lacks CDC activity (See, e.g., WO06/029879, WO99/51642, and WO05/100402; U.S. Pat. No. 6,194,551; and Idusogie et al. J. Immunol. 164: 4178-4184 (2000)). To assess complement activation, a CDC assay may be performed (See, e.g., Gazzano-Santoro et al., J. Immunol. Methods 202:163 (1996); Cragg, M. S. et al., Blood 101: 1045-1052 (2003); and Cragg et al., Blood 103:2738-2743 (2004)). FcRn binding and in vivo clearance/half-life determinations can also be performed using known methods (See, e.g., Petkova, S. B. et al., Int'l. Immunol. 18(12):1759-1769 (2006)). Antibodies with reduced effector function include those with substitution of one or more of Fc region residues 238, 265, 269, 270, 297, 327 and 329; or two or more of amino acid positions 265, 269, 270, 297 and 327, such as an Fc mutant with substitution of residues 265 and 297 to alanine (See, e.g., U.S. Pat. Nos. 6,737,056 and 7,332,581). Antibody variants with improved or diminished binding to FcRs are also included (See, e.g., U.S. Pat. No. 6,737,056; WO04/056312, and Shields et al., J. Biol. Chem. 9(2): 6591-6604 (2001)). In some embodiments, an antibody variant comprises an Fc region with one or more amino acid substitutions which improve ADCC, e.g., substitutions at positions 298, 333, and/or 334 of the Fc region.

Antibodies can have increased half-lives and improved binding to the neonatal Fc receptor (FcRn) (See, e.g., US 2005/0014934). Such antibodies can comprise an Fc region with one or more substitutions therein which improve binding of the Fc region to FcRn, and include those with substitutions at one or more of Fc region residues: 238, 256, 265, 272, 286, 303, 305, 307, 311, 312, 317, 340, 356, 360, 362, 376, 378, 380, 382, 413, 424 or 434 (See, e.g., U.S. Pat. No. 7,371,826). Other examples of Fc region variants are also contemplated (See, e.g., Duncan & Winter, Nature 322:738-40 (1988); U.S. Pat. Nos. 5,648,260 and 5,624,821; and WO94/29351).

Cysteine Engineered Antibody Variants

In some embodiments, it may be desirable to create cysteine engineered antibodies, e.g., "thioMAbs," in which one or more residues of an antibody are substituted with cysteine residues. In some embodiments, the substituted residues occur at accessible sites of the antibody. Reactive thiol groups can be positioned at sites for conjugation to other moieties, such as drug moieties or linker-drug moieties, to create an immunoconjugate. In some embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described (See, e.g., U.S. Pat. No. 7,521,541.

Antibody Derivatives

In some embodiments, an antibody provided herein may be further modified to contain additional nonproteinaceous moieties that are known and available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water.

The polymer may be of any molecular weight, and may be branched or unbranched. The number of polymers attached to the antibody may vary, and if two or more polymers are attached, they can be the same or different molecules.

In another embodiment, conjugates of an antibody and nonproteinaceous moiety that may be selectively heated by exposure to radiation are provided. In some embodiments, the nonproteinaceous moiety is a carbon nanotube (See, e.g., Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Recombinant Methods And Compositions

Antibodies may be produced using recombinant methods and compositions (See, e.g., U.S. Pat. No. 4,816,567). In some embodiments, an isolated nucleic acid encoding an anti-HIV antibody, or fragment thereof, described herein is provided. Such nucleic acid may encode an amino acid sequence comprising the $V_L$, and/or an amino acid sequence comprising the $V_H$ of the antibody. In a further embodiment, one or more vectors comprising such nucleic acid are provided. A vector is a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. In some embodiments, a nucleic acid and/or vector encoding a CAR comprising a binding domain derived from an anti-HIV antibody disclosed herein is provided.

In a further embodiment, a host cell comprising such nucleic acid is provided. Host cells are cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. In one such embodiment, a host cell comprises (e.g., has been transformed with) a vector comprising a nucleic acid that encodes an amino acid sequence comprising the $V_L$ of the antibody and an amino acid sequence comprising the $V_H$ of the antibody or a first vector comprising a nucleic acid that encodes an amino acid sequence comprising the $V_L$ of the antibody and a second vector comprising a nucleic acid that encodes an amino acid sequence comprising the $V_H$ of the antibody. In some embodiments, the host cell comprises a vector comprising a nucleic acid that encodes a CAR. In some embodiments, the host cell is eukaryotic, e.g., a Chinese Hamster Ovary (CHO) cell or lymphoid cell (e.g., YO, NS0, Sp20 cell). In some embodiments, a method of making an anti-HIV antibody is provided, wherein the method comprises culturing a host cell comprising a nucleic acid encoding the antibody, as provided above, under conditions suitable for expression of the antibody, and optionally recovering the antibody from the host cell or host cell culture medium. In some embodiments the host cell is a primary immune cell, e.g., a T cell, obtained from a patient. In some embodiments, the T cell is a CD4$^+$ T cell, a CD8$^+$ T cell, a regulatory T cell, or an NK cell.

For recombinant production of an anti-HIV antibody, an isolated nucleic acid encoding an antibody, e.g., as described above, is inserted into one or more vectors for further cloning and/or expression in a host cell. Such nucleic acid may be readily isolated and sequenced using conventional procedures.

Suitable host cells for cloning or expression of antibody-encoding vectors include prokaryotic or eukaryotic cells described herein. For example, antibodies may be produced in bacteria, e.g., when glycosylation and Fc effector function are not needed (See, e.g., U.S. Pat. Nos. 5,648,237, 5,789,199, and 5,840,523; Charlton, Methods in Molecular Biology, Vol. 248, pp. 245-254 (2003)). After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors (See, e.g., Gerngross, Nat. Biotech. 22:1409-1414 (2004), and Li et al., Nat. Biotech. 24:210-215 (2006)). Suitable host cells for the expression of glycosylated antibody are also derived from multicellular organisms, including invertebrates and vertebrates. Examples of invertebrates include plant and insect cells (See, e.g., U.S. Pat. Nos. 5,959,177, 6,040,498, 6,420,548, 7,125,978, and 6,417,429). Examples of vertebrate cells include mammalian cell lines, monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells; MRC 5 cells; FS4 cells; Chinese hamster ovary (CHO) cells, including DHFR$^-$CHO cells; and myeloma cell lines such as YO, NSO and Sp2/0. (See, e.g., Yazaki and Wu, Methods in Molecular Biology, Vol. 248, pp. 255-268 (2003).

Assays

Anti-HIV antibodies provided herein may be identified, screened for, or characterized for their physical/chemical properties and/or biological activities by various known assays.

In one aspect, an antibody of the invention is tested for its antigen binding activity, e.g., by ELISA, Western blot, etc. In one aspect, competition assays may be used to identify an antibody that competes with the anti-HIV antibodies described herein for binding to HIV. In some embodiments, such a competing antibody binds to the same epitope (e.g., a linear or a conformational epitope) that is bound by the anti-HIV antibodies described herein. Exemplary epitope mapping methods are known (See, e.g., Morris "Epitope Mapping Protocols," in Methods in Molecular Biology vol. 66 (1996)).

In an exemplary competition assay, immobilized HIV is incubated in a solution comprising a first labeled antibody that binds to HIV and a second unlabeled antibody that is being tested for its ability to compete with the first antibody for binding to HIV. The second antibody may be present in a hybridoma supernatant. As a control, immobilized HIV is incubated in a solution comprising the first labeled antibody but not the second unlabeled antibody. After incubation under conditions permissive for binding of the first antibody to HIV, excess unbound antibody is removed, and the amount of label associated with immobilized HIV is measured. If the amount of label associated with immobilized HIV is substantially reduced in the test sample relative to the control sample, then that indicates that the second antibody is competing with the first antibody for binding to HIV (See, e.g., Harlow and Lane Antibodies: A Laboratory Manual ch. 14 (1996)).

In one aspect, assays are provided for identifying anti-HIV antibodies thereof having biological activity. In some embodiments, assays are provided for identifying anti-HIV antibodies thereof having neutralization activity for HIV. Antibodies having such biological activity in vivo and/or in vitro are also provided. In some embodiments, an antibody of the invention is tested for such biological activity.

Immunoconjugates

The invention also provides immunoconjugates comprising an anti-HIV antibody herein. An immunoconjugate is an antibody conjugated to one or more heterologous molecule(s). For example, an immunoconjugate can comprise an anti-HIV antibody conjugated to one or more cytotoxic agents, such as chemotherapeutic agents or drugs, growth inhibitory agents, protein domains, toxins (e.g., protein toxins, enzymatically active toxins of bacterial, fungal, plant, or animal origin, or fragments thereof), or radioactive isotopes. In some embodiments, an immunoconjugate can comprise an anti-HIV antibody, or fragment thereof (e.g., an scFv).

In some embodiments, an immunoconjugate is an antibody-drug conjugate (ADC) in which an antibody is conjugated to one or more drugs, including but not limited to a maytansinoid; an auristatin such as monomethylauristatin drug moieties DE and DF (MMAE and MMAF); a dolastatin; a calicheamicin or derivative thereof; an anthracycline such as daunomycin or doxorubicin; methotrexate; vindesine; a taxane such as docetaxel, paclitaxel, larotaxel, tesetaxel, and ortataxel; a trichothecene; and CC1065 (See, e.g., U.S. Pat. Nos. 5,208,020, 5,416,064, 5,635,483, 5,780,588, 7,498,298, 5,712,374, 5,714,586, 5,739,116, 5,767,285, 5,770,701, 5,770,710, 5,773,001, 6,630,579, and 5,877,296; EP0425235B1; Hinman et al., Cancer Res. 53:3336-3342 (1993); Lode et al., Cancer Res. 58:2925-2928 (1998); Kratz et al., Current Med. Chem. 13:477-523 (2006); Jeffrey et al., Bioorganic & Med. Chem. Letters 16:358-362 (2006); Torgov et al., Bioconj. Chem.16:717-721 (2005); Nagy et al., Proc. Natl. Acad. Sci. USA 97:829-834 (2000); Dubowchik et al., Bioorg. & Med. Chem. Letters 12:1529-1532 (2002); and King et al., J. Med. Chem. 45:4336-4343 (2002)).

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, Phytolaca americana proteins (PAPI, PAPII, and PAP-S), *Momordica Charantia* inhibitor, curcin, crotin, Sapaonaria Officinalis Inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. Exemplary radioactive isotopes available for the production of radioconjugates include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. A radioconjugate can comprise a radioactive atom for scintigraphic detection (e.g., tc99m or 1123, or a spin label for nuclear magnetic resonance (NMR) imaging, such as iodine-123 again, iodine-131, indium-111, fluorine-19, carbon-13, nitrogen-15, oxygen-17, gadolinium, manganese or iron).

Conjugates of an antibody and cytotoxic agent can be made using bifunctional protein coupling agents, such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (e.g., disuccinimidyl suberate), aldehydes (e.g., glutaraldehyde), bis-azido compounds (e.g., bis(p-azidobenzoyl) hexanediamine), bis-diazonium derivatives (e.g., bis-(p-diazoniumbenzoyl)-ethylenediamine), diisocyanates (such as toluene 2,6-diisocyanate), and bis-active fluorine compounds (e.g., 1,5-difluoro-2,4-dinitrobenzene). For example, a ricin immunotoxin can be prepared (See, e.g., Vitetta et al., Science 238:1098 (1987)). Carbon-14-labeled 1-isothiocyanatobenzyl-3-methyldiethylene triaminepentaacetic acid (MX-DTPA) is an exemplary chelating agent for conjugation of radionucleotide to the antibody (See, e.g., WO94/11026). The linker may be cleavable, facilitating release of a cytotoxic drug in the cell. Exemplary cleavable linkers include an acid-labile linker, peptidase-sensitive linker, photolabile linker, dimethyl linker and disulfide-containing linker (See, e.g., Chari et al., Cancer Res. 52:127-131 (1992); U.S. Pat. No. 5,208,020).

Immunoconjugates or ADCs herein expressly contemplate conjugates prepared with cross-linker reagents. Exemplary cross-linker reagents include BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate).

Methods and Compositions for Diagnostics and Detection

In some embodiments, any of the anti-HIV antibodies provided herein is useful for detecting the presence of HIV in a biological sample. Detecting encompasses quantitative or qualitative detection.

The antibodies and compositions disclosed herein can be used for a variety of purposes, such as for detecting an HIV infection or diagnosing AIDS in a subject. These methods can include contacting a sample from the subject diagnosed with HIV or AIDS with an antibody described herein, and detecting binding of the antibody to the sample. An increase in binding of the antibody to the sample relative to binding of the antibody to a control sample confirms that the subject has an HIV-1 infection and/or AIDS. In some embodiments, the methods further comprise contacting a second antibody that binds HIV with the sample, and detecting binding of the second antibody. In some non-limiting examples an increase in binding of the antibody to the sample relative to a control sample detects HIV in the subject. In some non-limiting examples, the antibody specifically binds soluble gp120 in the sample. In some embodiments, the methods further comprise contacting a second antibody that specifically recognizes the HIV antibody with the sample and detecting binding of the second antibody.

According to another embodiment, the present invention provides diagnostic methods. Diagnostic methods generally involve contacting a biological sample obtained from a patient, such as, for example, blood, serum, saliva, urine, sputum, a cell swab sample, or a tissue biopsy, with an HIV antibody and determining whether the antibody preferentially binds to the sample as compared to a control sample or predetermined cut-off value, thereby indicating the presence of the HIV virus.

According to another embodiment, the present invention provides methods to detect the presence of the HIV antibodies of the present invention in a biological sample from a patient. Detection methods generally involve obtaining a biological sample from a patient, such as, for example, blood, serum, saliva, urine, sputum, a cell swab sample, or a tissue biopsy and isolating HIV antibodies or fragments thereof, or the nucleic acids that encode an HIV antibody, and assaying for the presence of an HIV antibody in the biological sample. Also, the present invention provides methods to detect the nucleotide sequence of an HIV antibody in a cell. The nucleotide sequence of an HIV antibody may also be detected using the primers disclosed herein. The presence of the HIV antibody in a biological sample from a patient may be determined utilizing known recombinant techniques and/or the use of a mass spectrometer.

In some embodiments, an anti-HIV antibody for use in a method of diagnosis or detection is provided. In a further aspect, a method of detecting the presence of HIV in a biological sample is provided. In some embodiments, the method comprises contacting the biological sample with an anti-HIV antibody as described herein under conditions permissive for binding of the anti-HIV antibody to HIV, and detecting whether a complex is formed between the anti-HIV antibody and HIV. Such method may be an in vitro or in vivo method. In some embodiments, an anti-HIV antibody is used to select subjects eligible for therapy with an anti-HIV antibody, e.g., where HIV is a biomarker for selection of patients.

Exemplary disorders that may be diagnosed using an antibody of the invention include disorders characterized by infection of HIV, including AIDS.

In some embodiments, labeled anti-HIV antibodies are provided. Labels include, but are not limited to, labels or moieties that are detected directly (e.g., fluorescent, chromophoric, electron-dense, chemiluminescent, and radioactive labels), as well as moieties detected indirectly, e.g., through an enzymatic reaction or molecular interaction (e.g., enzymes or ligands). Exemplary labels include radioisotopes (e.g., 32P, 14C, 1251 41, and $^{131}$I), fluorophores (e.g., rare earth chelates or fluorescein and its derivatives, rhodamine and its derivatives, dansyl, umbelliferone, luceriferases (See, e.g., U.S. Pat. No. 4,737,456), luciferin, 2,3-dihydrophthalazinediones, horseradish peroxidase (HRP), alkaline phosphatase, 0-galactosidase, glucoamylase, lysozyme, saccharide oxidases, heterocyclic oxidases, coupled with an enzyme that employs hydrogen peroxide to oxidize a dye precursor, biotin/avidin, spin labels, bacteriophage labels, stable free radicals, and the like.

Pharmaceutical Formulations

Also provided are pharmaceutical formulations of an anti-HIV antibody as described herein are prepared by mixing such antibody having the desired degree of purity with one or more optional pharmaceutically acceptable carriers (See, e.g., Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed. Exemplary pharmaceutical acceptable carriers include buffers (e.g., phosphate, citrate, and other organic acids); antioxidants (e.g., ascorbic acid and methionine); preservatives (e.g., octadecyldimethylbenzyl ammonium chloride); hexamethonium chloride; benzalkonium chloride; benzethonium chloride; phenol, butyl or benzyl alcohol; alkyl parabens (e.g., methyl or propyl paraben); catechol; resorcinol; cyclohexanol; 3-pentanol; and m-cresol; low molecular weight (less than about 10 residues) polypeptides; proteins, (e.g., serum albumin, gelatin, or immunoglobulins); hydrophilic polymers (e.g., polyvinylpyrrolidone); amino acids (e.g., glycine, glutamine, asparagine, histidine, arginine, or lysine); monosaccharides, disaccharides, and other carbohydrates (e.g., glucose, mannose, or dextrins); chelating agents (e.g., EDTA); sugars (e.g., sucrose, mannitol, trehalose or sorbitol); salt-forming counter-ions (e.g., sodium); metal complexes (e.g., Zn-protein complexes); and/or non-ionic surfactants (e.g., polyethylene glycol (PEG)). Exemplary pharmaceutically acceptable carriers herein further include insterstitial drug dispersion agents (e.g., soluble neutral-active hyaluronidase glycoproteins (sHASEGP)) (See, e.g., U.S. Pat. Pub. Nos. US 2005/0260186 and US 2006/0104968). In one aspect, a sHASEGP is combined with one or more additional glycosaminoglycanases (e.g., chondroitinases).

Also provided are pharmaceutical formulations including the anti-HIV-antibody, or fragment thereof, and/or fusion protein, and/or, chimeric receptor, and/or the engineered cells expressing the molecules. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell, binding molecule, and/or antibody, and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition.

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

Formulations of the antibodies can include lyophilized formulations and aqueous solutions.

The formulation or composition may also contain more than one active ingredients useful for the particular indication, disease, or condition being treated with the antibodies, or fragments thereof, or cells, preferably those with activities complementary to the antibody, or fragment thereof, or cell, where the respective activities do not adversely affect one another. In some embodiments, the formulation may also comprise ingredients as necessary for treating, ameliorating, managing, reducing viral burden, or lessening disease severity of a particular indication (e.g., HIV infection or AIDS). Such active ingredients are suitably present in combination in amounts that are effective for the purpose intended. Thus, in some embodiments, the pharmaceutical composition further includes other pharmaceutically active agents or drugs, such as antiviral agents. In some embodiments, the cells or antibodies are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

Antibody formulations can be lyophilized (See, e.g., U.S. Pat. No. 6,267,958). Antibody formulations can be aqueous antibody (See, e.g., U.S. Pat. No. 6,171,586 and WO06/044908).

Active ingredients may be entrapped in microcapsules (e.g., hydroxymethylcellulose or gelatin-microcapsules and poly-(methylmethacylate) Active ingredients may be entrapped in microcapsules in colloidal drug delivery systems (e.g., liposomes, albumin microspheres, microemulsions, nano-particles and nanocapsules) or in macroemulsions. Sustained-release preparations may be prepared. Suitable examples of sustained-release preparations include semipermeable matrices of solid hydrophobic polymers containing the antibody, which matrices are in the form of shaped articles (e.g., films or microcapsules).

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

The pharmaceutical composition in some embodiments contains the antibodies, or fragments thereof, and/or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

In certain embodiments, in the context of genetically engineered cells containing the antibody or fragment thereof, a subject is administered the range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges, and/or such a number of cells per kilogram of body weight of the subject.

The compositions may be administered using standard administration techniques, formulations, and/or devices. Provided are formulations and devices, such as syringes and vials, for storage and administration of the compositions. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo, or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the antibody, or fragment thereof, in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

Sustained-release preparations may be prepared. Suitable examples of sustained-release preparations include semipermeable matrices of solid hydrophobic polymers containing the antibody, which matrices are in the form of shaped articles, e.g., films, or microcapsules.

The formulations to be used for in vivo administration are generally sterile (e.g., by filtration through sterile filtration membranes).

Therapeutic Methods And Compositions

Any of the anti-HIV antibodies provided herein may be used in therapeutic methods. The present invention provides a method for treating a mammal infected with a virus infection (e.g., HIV), comprising administering to said mammal a pharmaceutical composition comprising the HIV antibodies disclosed herein. Methods for reducing an increase in HIV virus titer, virus replication, virus proliferation or an amount of an HIV viral protein in a subject are further provided.

In one aspect, an anti-HIV antibody for use as a medicament is provided. In further aspects, an anti-HIV antibody for use in treating HIV infection is provided. In some embodiments, the anti-HIV antibody neutralizes HIV. In some embodiments, the anti-HIV antibody is a broadly neutralizing antibody. In other embodiments, the HIV is HIV-1. In some embodiments, the HIV is HIV-2. In other embodiments, the HIV is HIV-1 group M. In some embodiments, the HIV is HIV-1 group N, HIV-1 group 0, and/or HIV-1 group P. In other embodiments, the HIV is Glade A (including A1 and/or A2), B, C, D, E, F (including F1 and/or F2), G, H, I, J, K, or any combination, subtype, or CRF thereof. In further aspects, an anti-HIV antibody for use in treating AIDS is provided. In some embodiments, an anti-HIV antibody for use in a method of treatment is provided. In some embodiments, the invention provides an anti-HIV antibody for use in a method of treating an individual infected with HIV or having AIDS comprising administering to the individual an effective amount of the anti-HIV antibody. An effective amount of an agent, is an amount effective, at dosages and for periods of time necessary, to achieve the desired therapeutic or prophylactic result. In one such embodiment, the method further comprises administering to the individual an effective amount of at least one additional therapeutic agent. The individual can be a human.

In a further aspect, the invention provides for the use of an anti-HIV antibody in the manufacture or preparation of a medicament. In some embodiments, the medicament is for treatment of HIV infection. In some embodiments, the medicament is for treatment of AIDS. In a further embodiment, the medicament is for use in a method of treating HIV infection or AIDS comprising administering to an individual having HIV infection or AIDS an effective amount of the medicament.

In a further aspect, the invention provides a method for treating HIV infection or AIDS. In some embodiments, the method comprises administering to an individual having such HIV infection or AIDS an effective amount of an anti-HIV antibody.

In some embodiments, the HIV of the infection or AIDS expresses gp120 on the surface of its constituent viruses.

According to another embodiment, the present invention provides methods for the preparation and administration of an HIV antibody composition that is suitable for administration to a human or non-human primate patient having HIV infection, or at risk of HIV infection, in an amount and according to a schedule sufficient to induce a protective immune response against HIV, or reduction of the HIV virus, in a human.

According to another embodiment, the present invention provides a vaccine comprising at least one antibody of the invention and a pharmaceutically acceptable carrier. According to one embodiment, the vaccine is a vaccine comprising at least one antibody described herein and a pharmaceutically acceptable carrier. The vaccine can include a plurality of the antibodies having the characteristics described herein in any combination and can further include additional antibodies, such as other available antibodies neutralizing to HIV.

It is to be understood that compositions can be a single or a combination of antibodies disclosed herein, which can be the same or different, in order to prophylactically or therapeutically treat the progression of various subtypes of HIV infection after vaccination. Such combinations can be selected according to the desired immunity. When an antibody is administered to an animal or a human, it can be combined with one or more pharmaceutically acceptable carriers, excipients or adjuvants.

Further, with respect to determining the effective level in a patient for treatment of HIV, in particular, suitable animal models are available and have been widely implemented for evaluating the in vivo efficacy against HIV of various gene therapy protocols (Sarver et al. (1993b), supra). These models include mice, monkeys and cats. Even though these animals are not naturally susceptible to HIV disease, chimeric mice models (for example, SCID, bg/nu/xid, NOD/ SCID, SCID-hu, immunocompetent SCID-hu, bone marrow-ablated BALB/c) reconstituted with human peripheral blood mononuclear cells (PBMCs), lymph nodes, fetal liver/ thymus or other tissues can be infected with lentiviral vector or HIV, and employed as models for HIV pathogenesis. Similarly, the simian immune deficiency virus (SIV)/monkey model can be employed, as can the feline immune deficiency virus (FIV)/cat model. The pharmaceutical composition can contain other pharmaceuticals, in conjunction with a vector according to the invention, when used to therapeutically treat AIDS. These other pharmaceuticals can be used in their traditional fashion (i.e., as agents to treat HIV infection). According to another embodiment, the present invention provides an antibody-based pharmaceutical composition comprising an effective amount of an isolated HIV antibody, or an affinity matured version, which provides a prophylactic or therapeutic treatment choice to reduce infection of the HIV virus. The antibody-based pharmaceutical composition of the present invention may be formulated by any number of generally known strategies(See, e.g., McGoff and Scher, 2000, Solution Formulation of Proteins/ Peptides: In McNally, E. J., ed. Protein Formulation and Delivery. New York, N.Y.: Marcel Dekker; pp. 139-158; Akers and Defilippis, 2000, Peptides and Proteins as Parenteral Solutions. In: Pharmaceutical Formulation Development of Peptides and Proteins. Philadelphia, Pa.: Talyor and Francis; pp. 145-177; Akers, et al., 2002, Pharm. Biotechnol. 14:47-127).

In another embodiment, the present invention provides a method for detecting an HIV antibody comprising a heavy chain comprising a highly conserved consensus sequence and a light chain comprising a highly conserved consensus sequence in a biological sample, comprising obtaining an immunoglobulin-containing biological sample from a mammalian subject, isolating an HIV antibody from said sample, and identifying the highly conserved consensus sequences of the heavy chain and the light chain. The biological sample may be blood, serum, saliva, urine, sputum, a cell swab sample, or a tissue biopsy. The amino acid sequences may be determined by known methods including, for example, PCR and mass spectrometry.

In a further aspect, the invention provides pharmaceutical formulations comprising any of the anti-HIV antibodies provided herein (e.g., for use in any of the above therapeutic methods). In some embodiments, a pharmaceutical formulation comprises any of the anti-HIV antibodies provided herein and a pharmaceutically acceptable carrier. In another embodiment, a pharmaceutical formulation comprises any of the anti-HIV antibodies provided herein and at least one additional therapeutic agent.

Antibodies, or fragments thereof, as described herein can be used either alone or in combination with other agents in a therapy. For instance, an antibody of the invention may be co-administered with at least one additional therapeutic agent. For example, the antibodies or fragments thereof can be used either alone or in combination with one or more than one antibody (for example, a plurality or pool of antibodies). For example, the antibodies can be used either alone or in combination with one or more other antibodies (e.g., HIV neutralizing antibodies), for example, but not limited to VRCO1, VRCO2, VRC03, VRC-PG-04, VRC-PG-05, b12, (CD4bs), (PGTs, PG9, and PG16. (See, Science 333(6049): 1633-1637; Nature 477(7365):466-470; Science 334(6060): 1289-1293; Science 326(5950):285-289; Science 334 (6059): 1097-1103; and Nature 480(7377):336-343.)

According to another embodiment, the present invention provides a method for treating a mammal infected with a virus infection, such as, for example, HIV, comprising administering to said mammal a pharmaceutical composition comprising the HIV antibodies disclosed herein. According to one embodiment, the method for treating a mammal infected with HIV comprises administering to said mammal a pharmaceutical composition that comprises an antibody of the present invention, or a fragment thereof.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant.

Also provided are methods and uses for adoptive cell therapy. In some embodiments, the methods include administration of the cells or a composition containing the cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition. In some aspects, the methods thereby treat, e.g., ameliorate one or more symptom of the disease or condition.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In some embodiments, the cell therapy, e.g., adoptive cell therapy such as adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive cell therapy such as adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject, to whom the cells, cell populations, or compositions are administered is a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent. In some examples, the patient or subject is a validated animal model for disease, adoptive cell therapy, and/or for assessing toxic outcomes such as cytokine release syndrome (CRS).

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route. For example, dosing can be by injections (e.g., intravenous or subcutaneous injections). Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. About 1 pg/kg to 15 mg/kg (e.g., 0.1 mg/kg-10 mg/kg) of antibody can be an initial candidate dosage for administration to the patient (e.g., by one or more separate administrations, or by continuous infusion). A daily dosage might range from about 1 pg/kg to 100 mg/kg or more. For repeated administrations over several days or longer the treatment would generally be sustained until a desired suppression of infection or disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently (e.g., every week or every three weeks). An initial higher loading dose, followed by one or more lower doses may be administered.

It is understood that any of the above formulations or therapeutic methods may be carried out using an immunoconjugate of the invention in place of or in addition to an anti-HIV antibody.

Methods for reducing an increase in HIV virus titer, virus replication, virus proliferation or an amount of an HIV viral protein in a subject are further provided. According to another aspect, a method includes administering to the subject an amount of an HIV antibody effective to reduce an increase in HIV titer, virus replication or an amount of an HIV protein of one or more HIV strains or isolates in the subject.

According to another embodiment, the present invention provides a method of reducing viral replication or spread of HIV infection to additional host cells or tissues comprising contacting a mammalian cell with the antibody, or a portion thereof, which binds to an antigenic epitope on gp120.

Passive immunization can be used to effectively and safely prevent and treat viral diseases. (See, e.g., Keller et al., Clin. Microbiol. Rev. 13:602-14 (2000); Casadevall, Nat. Biotechnol. 20: 114 (2002); Shibata et al, Nat. Med. 5:204-10 (1999); and Igarashi et al, Nat. Med. 5:211-16 (1999)).

Passive immunization using human monoclonal antibodies provides an immediate treatment strategy for emergency prophylaxis and treatment of HIV.

Subjects at risk for HIV-related diseases or disorders include patients who have come into contact with an infected person or who have been exposed to HIV in some other way. Administration of a prophylactic agent can occur prior to the manifestation of symptoms characteristic of HIV-related disease or disorder, such that a disease or disorder is prevented or, alternatively, delayed in its progression.

Articles of Manufacture

In one aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The present invention also includes isolated nucleic acid sequences encoding the polypeptides for the heavy and light chains of the HIV antibodies listed in Tables 1 and 2 the sequences for the heavy and light chains of SEQ ID NOs: 1-16 and 65.

TABLE 1

Heavy chain amino acid sequences

| SEQ ID NO: | KABAT | FWR1 | CDR1 | FWR2 | CDR2 | FWR3 | CDR3 | FWR4 |
|---|---|---|---|---|---|---|---|---|
| 1 | AbV-1H | QMQLQESG PGLVKPSET LSLTCVVSG GSVS | GNIWS | WIRQSPGK GPEWVG | FVSGEYIE YNPSLKS | RLTISRDTSK NQLSLTLRSV TAADTAMYY CAK | TLRARRIYGV IAFGEVYDY HYFDV | WGKGTM VTVSS |
| 3 | AbV-2H | QVQLQESG PGLVKPSET LSVTCSVSG DSMN | NYYWT | WIRQSPGK GLEWIG | YVSDRAS ATYNPSL KS | RVVISRDTSK NQLSLKLNS VTLADTAVY YCAT | ARRGQRIYG EVAFGEFFY YYSMDV | WGKGTA VTVSS |
| 5 | AbV-3H | QLQLQESGP GLVKPPETL SLTCSVSGA SIN | DAYWS | WIRQSPGK RPEWVG | YVHHSGD TNYNPSL KR | RVTFSLDTA KNEVSLKLV ALTAADSAV YFCAR | ALHGKRIYG TVALGELFV YFHMDV | WGKGTA VTVSS |
| 7 | AbV-4H | QLQLQESGP GLVKPPETL SLTCSVSGA SIN | DAYWS | WIRQSPGK RPEWVG | YVHHSGD TNYNPSL KR | RVTFSLDTA KNEVSLKLV ALTAADSAV YFCAR | ALHGKRIYG TVALGELFV YFYMDV | WGKGTA VTVSS |
| 9 | AbV-5H | QVHLQESG PGLVKPSET LSLTCNVSG TLVR | DNYWS | WIRQPLGK QPEWIG | YVHDSGD TNYNPSL KS | RVHLSLDKS KNLVSLRLT GVTAADSAI YYCAT | TKHGRRIYG VVAFKEWFT YFYMDV | WGKGTS VTVSS |
| 11 | AbV-6H | QVHLQESG PGLVKPSET LSLTCNVSG TLVR | DNYWS | WIRQPLGK QPEWIG | YVHDSGD TNYNPSL KS | RVHLSLDKS KNLVSLRLT GVTAADSAI YYCAT | TKHGRRIYG VVAFKEWFT YFYMDV | WGKGTS VTVSS |
| 13 | AbV-7H | QMQLQESG PGLVKPSET LSLTCSVSG ASIS | DSYWS | WFRRSPG KGLEWIG | YVHKSGD TNYSPSLK S | RVNLSLDAS KNQVSLSLV AATAADSGK YYCAR | TLHGRRIYGI VAFNEWFTY FYMDV | WGNGTQ VTVSS |
| 15 | AbV-8H | QVHLQESG PGLVKPSET LSLTCVVSG ASTS | GQYWS | WIRQSPGK GLEWIG | YRSDSGD ANYNPSL KS | RVIISLDTSR NQLSLNVTS VTTADTAMY FCAR | AQRGKRIYG VVSLGEYYH YYIMDV | WGTGTP VTVSS |
| 16 | AbV-9H | QVQLQESG PGLVKPSET LSVTCSVSG DSMN | NYYWT | WIRQSPGK GLEWIG | YISDRASA TYNPSLNS | RVVISRDTSK NQLSLKLNS VTPADTAVY YCAT | ARRGQRIYG EVSFGEFFYY YSMDV | WGKGTA VTVSS |

TABLE 2

Light chain amino acid sequences

| SEQ ID NO: | KABAT | FWR1 | CDR1 | FWR2 | CDR2 | FWR3 | CDR3 | FWR4 |
|---|---|---|---|---|---|---|---|---|
| 2 | AbV-1L | TDSVASDVAMSVAPGDTATISC | GEKSNGARAVQ | WYQQKPGQAPVLIIY | NNQDRPS | GIPERFSASPDAGFGTTATLTISRVEAGDEADYYC | HIWDSRFPLSWV | FAGGTKLTVL |
| 4 | AbV-2L | GSVTSFVRPLSVALGETASISC | GRQALGSRAVQ | WYQHRPGQAPVLLIY | NNQDRPS | GIPERFSGTPDINFGTRATLTISGVEAGDEADYYC | HMWDSRSGFSWS | FGGATRLTVL |
| 6 | AbV-3L | HCTGAVSSFVSVAPGQTARITC | GEESLGSRSVI | WYQQRPGQAPSLIIY | NNNDRPS | GIPERFSGSPGSTFGTTATLTITSVEAGDEADYYC | HIWDSRRPTNWV | FGEGTTLTVL |
| 8 | AbV-4L | HCTGAVSSFVSVAPGQTARITC | GEESLGSRSVI | WYQQRPGQAPSLIIY | NNNDRPS | GIPERFSGSPGSTFGTTATLTITSVEAGDEADYYC | HIWDSRRPTNWV | FGEGTTLTVL |
| 10 | AbV-5L | HCTASLASSMSVSPGETAKISC | GKESIGSRAVQ | WYQQKPGQPPSLIIY | NNQDRPA | GVPERFSASPDFRPGTTATLTITNVDAEDEADYYC | HIYDARGGTNWV | FDRGTTLTVL |
| 12 | AbV-6L | HCTGSLASSMSVSPGETAKISC | GKESIGSRAVQ | WYQQKPGQPPSLIIY | NNQDRPA | GVPERFSASPDFRPGTTATLTITNVDAEDEADYYC | HIYDARGGTNWV | FDRGTTLTVL |
| 14 | AbV-7L | HCTASVTSDISVAPGETARISC | GEKSLGSRAVQ | WYQHRAGQAPSLIIY | NNQDRPS | GIPERFSGSPDSAFGTTATLTITSVEAGDEADYYC | HIWDSRVPTKWV | FGGGTTLTVL |
| 4 | AbV-9L-a (AbV-2L) | GSVTSFVRPLSVALGETASISC | GRQALGSRAVQ | WYQHRPGQAPVLLIY | NNQDRPS | GIPERFSGTPDINFGTRATLTISGVEAGDEADYYC | HMWDSRSGFSWS | FGGATRLTVL |
| 65 | AbV-9L-b (10-847) | XXXXSYVRPLSVALGETASISC | GRQALGSRAVQ | WYQHRPGQAPILLIY | NNQDRPS | GIPERFSGTPDINFGTRATLTISGVEAGDEADYYC | HMWDSRSGFSWS | FGGATRLTVL |

TABLE 3

Heavy and Light Chain Pairings

| | SEQ ID NOs | | | |
|---|---|---|---|---|
| | Variable Region | | CDRs 1-3 | |
| Name | Heavy Chain (H) | Light Chain (L) | Heavy Chain (H) | Light Chain (L) |
| AbV-1 | SEQ ID NO: 1 | SEQ ID NO: 2 | SEQ ID NOs: 17-19 | SEQ ID NOs: 20-22 |
| AbV-2 | SEQ ID NO: 3 | SEQ ID NO: 4 | SEQ ID NOs: 23-25 | SEQ ID NOs: 26-28 |
| AbV-3 | SEQ ID NO: 5 | SEQ ID NO: 6 | SEQ ID NOs: 29-31 | SEQ ID NOs: 32-34 |
| AbV-4 | SEQ ID NO: 7 | SEQ ID NO: 8 | SEQ ID NOs: 35-37 | SEQ ID NOs: 38-40 |
| AbV-5 | SEQ ID NO: 9 | SEQ ID NO: 10 | SEQ ID NOs: 41-43 | SEQ ID NOs: 44-46 |
| AbV-6 | SEQ ID NO: 11 | SEQ ID NO: 12 | SEQ ID NOs: 47-49 | SEQ ID NOs: 50-52 |
| AbV-7 | SEQ ID NO: 13 | SEQ ID NO: 14 | SEQ ID NOs: 53-55 | SEQ ID NOs: 56-58 |
| AbV-8 | SEQ ID NO: 15 | N/A | SEQ ID NOs: 59-61 | N/A |
| AbV-9 | SEQ ID NO: 16 | SEQ ID NO: 4 SEQ ID NO: 65 | SEQ ID NOs: 62-64 SEQ ID NOs: 62-64 | SEQ ID NOs: 26-28 SEQ ID NOs: 66-68 |

TABLE 4

Excluded heavy chain amino acid sequences

| SEQ ID NO: | KABAT | FWR1 | CDR1 | FWR2 | CDR2 | FWR3 | CDR3 | FWR4 |
|---|---|---|---|---|---|---|---|---|
| 69 | GL | QVQLQESGPGLVKPSETLSLTCTVSGGSIS | SYYWS | WIRQPPGKGLEWIG | YIYYSGSTNYNPSLKS | RVTISVDTSKNQFSLKLSSVTAADTAVYYCAR | TQQGKRIYGVVSFGDYYYYYMDV | WGKGTTVTVSS |

TABLE 4-continued

Excluded heavy chain amino acid sequences

| SEQ ID NO: | KABAT | FWR1 | CDR1 | FWR2 | CDR2 | FWR3 | CDR3 | FWR4 |
|---|---|---|---|---|---|---|---|---|
| 76 | Consensus | QVQLQESGPGLVKPSETLSLTCSVSGX$_1$SX$_2$X$_3$ | DX$_4$YWS | WIRQSPGKGLEWIG | YVHDSGDTNYNPSLKS | X$_5$X$_6$SLDTSKNQVSLKLX$_7$X$_8$VTAADSAX$_9$YYCAR | AX$_{10}$HGX$_{11}$RIYGIVAFGEX$_{12}$FTYFYMDV | WGKGTTVTVSS |
| 77 | 10-1369 | QVQLQESGPGLVKPLETLSLTCNVSGAFIA | DHYWS | WIRLPLGKGPEWIG | YVHDSGDINYNPSLKN | RVHLSLDKSTNQVSLKLMAVTAGDSALYYCAT | TKHGRRIYGVVAFGEWFTYFYMDV | WGRGTTVTVSS |
| 78 | 10-259 | QVHLQESGPGLVKPSETLSLTCNVSGTLVR | DNYWS | WMRQPLGKQPEWIG | YVHDSGDTNYNPSLKS | RVHLSLDKSNNLVSLRLTAVTAADSATYYCAT | TKHGRRIYGIVAFNEWFTYFYMDV | WGKGTTVTVSS |
| 79 | 10-303 | QVQLQESGPGLVKPSETLSLTCSVSGASIS | DSYWS | WIRRSPGKGLEWIG | YVHKSGDTNYSPSLKS | RVNLSLDTSKNQVSLSLVAATAADSGKYYCAR | TLHGRRIYGIVAFNEWFTYFYMDV | WGNGTQVTVSS |
| 80 | 10-410 | QVQLQESGPGLVKPPETLSLTCSVSGASVN | DAYWS | WIRQSPGKRPEWVG | YVHHSGDTNYNPSLKR | RVTFSLDTAKNEVSLKLVALTAADSAVYFCAR | ALHGKRIYGIVALGELFTYFYMDV | WGKGTTVTVSS |
| 81 | 10-1130 | QVQLQESGPGLVKPPETLSLTCSVSGASIN | DAYWS | WIRQSPGkRPEWVG | YVHHSGDTNYNPSLKR | RVTFSLDTAKNEVSLKLVDLTAADSAVYFCAR | ALHGKRIYGIVALGELFTYFYMDV | WGKGTTVTVSS |
| 82 | 10-1121 | QVQLQESGPGLVKPPETLSLTCSVSGASIN | DAYWS | WIRQSPGKRPEWVG | YVHHSGDTNYNPSLKR | RVSFSLDTAKNEVSLKLVDLTAADSAIYFCAR | ALHGKRIYGIVALGELFTYFYMDV | WGKGTTVTVSS |
| 83 | 10-1146 | QVQLVESGPGLVTPSETLSLTCTVSNGSVS | GRFWS | WIRQSPGRGLEWIG | YFSDTDRSEYSPSLRS | RLTLSLDASRNQLSLKLKSVTAADSATYYCAR | AQQGKRIYGIVSFGEFFYYYMDA | WGKGTAVTVSS |
| 84 | 10-996 | QVQLQESGPGLVKPSETLSLTCSVSNGSVS | GRFWS | WIRQSPGRGLEWIG | YFSDTEKSNYNPSLRS | RLTLSVDASKNQLSLKLNSVTAADSATYYCAR | TQQGKRIYGVVSFGEFFHYYMDA | WGKGTAVTVSS |
| 85 | 10-1341 | QVQLQESGPGLVKPSETLSVTCSVSGDSMN | NVYWT | WIRQSPGKGLEWIG | YISDRESATYNPSLNS | RWISRDTSTNQLSLKLNSVTPADTAVYYCAT | ARRGQRIYGVVSFGEFFYYYSMDV | WGRGTTVTVSS |
| 86 | 10-847 | QVQLQESGPGLVKPSETLSVTCSVSGDSMN | NYYWT | WIRQSPGKGLEWIG | YISDRASATYNPSLNS | RVVISRDTSKNQLSLKLNSVTPADTAVYYCAT | ARRGQRIYGVVSFGEFFYYYSMDV | WGKGTTVTVSS |
| 87 | 10-1074 | QVQLQESGPGLVKPSETLSVTCSVSGDSMN | NYYWT | WIRQSPGKGLEWIG | YISDRESATYNPSLNS | RVVISRDTSKNQLSLKLNSVTPADTAVYYCAT | ARRGQRIYGVVSFGEFFYYYSMDV | WGKGTTVTVSS |
| 88 | 10-1074GM | QVQLQESGPGLVKPSETLSVTCSVSGDSMN | NSYWT | WIRQSPGKGLEWIG | YISKSESANYNPSLNS | RVVISRDTSKNQLSLKLNSVTPADTAVYYCAT | ARHGQRIYGVVSFGEFFTYYSMDV | WGKGTTVTVSS |

TABLE 5

Excluded light chain amino acid sequences

| SEQ ID NO: | KABAT | FWR1 | CDR1 | FWR2 | CDR2 | FWR3 | CDR3 | FWR4 |
|---|---|---|---|---|---|---|---|---|
| 70 | GL | SYVLTQPPSVSVAPGQTARITC | GGNNIGSKSVH | WYQQKPGQAPVLVVY | DDSDRPS | GIPERFSGSNSGNTATLTISRVEAGDEADYYC | QVWDSSSDHPWV | FGGGTKLTVL |
| 89 | Consensus | SX$_1$VRPQPPSLSVAPGETARIX$_2$C | GEX$_3$SLGSRAVQ | WYQQRPGQAPSLIIY | NNQDRPS | GIPERFSGSPDX$_4$X$_5$FGTTATLTITX$_6$VEAGDEADYYC | HIWDSRX$_7$PTX$_8$WV | FGGGTTLTVL |
| 90 | 10-1369 | SSMSVSPGETAKITC | GEKSIGSRAVQ | WYQKKPGQPPSLIIY | NNQDRPS | GVPERFSASPDIEFGTTATLTITNVEAGDEADYYC | HIYDARRPTNWV | FDRGTTLTVL |
| 21 | 10-259 | SSMSVSPGETAKISC | GKESIGSRAVQ | WYQQKSGQPPSLIIY | NNQDRPS | GVPERFSATPDFGAGTTATLTITNVEADDEADYYC | HIYDARGGTNWV | FDRGATLTVL |
| 22 | 10-303 | SDISVAPGETARISC | GEKSLGSRAVQ | WYQHRAGQAPSLIIY | NNQDRPS | GIPERFSGSPDSPFGTTATLTITSVEAGDEADYYC | HIWDSRVPTKWV | FGGGTTLTVL |
| 93 | 10-1121 | SFVSVAPGQTARITC | GEESLGSRSVI | WYQQRPGQAPSLIMY | NNHDRPS | GIPERFSGSPGSTFGTTATLTITSVEAGDEADYYC | HIWDSRRPTNWV | FGEGTTLTVL |
| 94 | 10-410 | SFVSVAPGQTARITC | GEESLGSRSVI | WYQQRPGQAPSLIIY | NNNDRPS | GIPERFSGSPGSTFGTTATLTITSVEAGDEADYYC | HIWDSRRPTNWV | FGEGTTLTVL |
| 21 | 10-1130 | SFVSVAPGQTARITC | GEESLGSRSVI | WYQQRPGQAPSLIIY | NNNDRPS | GIPERFSGSPGSTFGTTATLTITSVEAGDEADYYC | HIWDSRRPTNWV | FGEGTTLTVL |
| 95 | 10-847 | SYVRPLSVALGETASISC | GRQALGSRAVQ | WYQHRPGQAPILLIY | NNQDRPS | GIPERFSGTPDrNFGTRATLTISGVEAGDEADYYC | HMWDSRSGFSWS | FGGATRLTVL |
| 96 | 10-1074 | SYVRPLSVALGETARISC | GRQALGSRAVQ | WYQHRPGQAPILLIY | NNQDRPS | GIPERFSGTPDINFGTRATLTISGVEAGDEADYYC | HMWDSRSGFSWS | FGGATRLTVL |
| 96 | 10-1341 | SYVRPLSVALGETARISC | GRQALGSRAVQ | WYQHRPGQAPILLIY | NNQDRPS | GIPERFSGTPDINFGTRATLTISGVEAGDEADYYC | HMWDSRSGFSWS | FGGATRLTVL |
| 97 | 10-996 | SSLPLSVAPGATAKIAC | GEKSFASRAVQ | WYQQKPGQAPVLIIY | NNQDRPA | GVSERFSGTPDVGFGSTATLTISRVEAGDEADYYC | HKWDSRSPLSWV | FGGGTQLTVL |
| 98 | 10-1146 | SSLPLSLAPGATAKIPC | GEKSRGSRAVQ | WYQQKPGQAPTLIIY | NNQDRPA | GVSERYSGNPDVAIGVTATLTISRVEAGDEAEYYC | HYWDSRSPISWV | FGGWTQLTVL |

SEQUENCE LISTING

SEQ ID NOs: 1-16-Heavy and light chain variable region sequences:

SEQ ID NO: 1
QMQLQESGPGLVKPSETLSLTCVVSGGSVSGNIWSWIRQSPGKGPEWVGF
VSGEYIEYNPSLKSRLTISRDTSKNQLSLTLRSVTAADTAMYYCAKTLRA
RRIYGVIAFGEVYDYHYFDVWGKGTMVTVSS

SEQ ID NO: 2
TDSVASDVAMSVAPGDTATISCGEKSNGARAVQWYQQKPGQAPVLIIYNN
QDRPSGIPERFSASPDAGFGTTATLTISRVEAGDEADYYCHIWDSRFPLS
WVFAGGTKLTVL

SEQ ID NO: 3
QVQLQESGPGLVKPSETLSVTCSVSGDSMNNYYWTWIRQSPGKGLEWIGY
VSDRASATYNPSLKSRVVISRDTSKNQLSLKLNSVTLADTAVYYCATARR
GQRIYGEVAFGEFFYYYSMDVWGKGTAVTVSS

SEQ ID NO: 4
GSVTSFVRPLSVALGETASISCGRQALGSRAVQWYQHRPGQAPVLLIYNN
QDRPSGIPERFSGTPDINFGTRATLTISGVEAGDEADYYCHMWDSRSGFS
WSFGGATRLTVL

SEQ ID NO: 5
QLQLQE SGPGLVKPPETLSLTCSVSGASINDAYWSWIRQSPGKRPEWVG
YVEIHSGDTNYNPSLKRRVTFSLDTAKNEVSLKLVALTAADSAVYFCARA
LHGKRIYGTVALGELFVYFHMDVWGKGTAVTVSS

SEQ ID NO: 6
HCTGAVSSFVSVAPGQTARITCGEESLGSRSVIWYQQRPGQAPSLIIYNN
NDRPSGIPERFSGSPGSTFGTTATLTITSVEAGDEADYYCHIWDSRRPTN
WVFGEGTTLTVL

SEQ ID NO: 7
QLQLQE SGPGLVKPPETLSLTCSVSGASINDAYWSWIRQSPGKRPEWVG
YVEIHSGDTNYNPSLKRRVTFSLDTAKNEVSLKLVALTAADSAVYFCARA
LHGKRIYGTVALGELFVYFYMDVWGKGTAVTVSS

SEQ ID NO: 8
HCTGAVSSFVSVAPGQTARITCGEESLGSRSVIWYQQRPGQAPSLIIYNN
NDRPSGIPERFSGSPGSTFGTTATLTITSVEAGDEADYYCHIWDSRRPTN
WVFGEGTTLTVL

SEQ ID NO: 9
QVHLQESGPGLVKPSETLSLTCNVSGTLVRDNYWSWIRQPLGKQPEWIGY
VHDSGDTNYNPSLKSRVHLSLDKSKNLVSLRLTGVTAADSAIYYCATTKH
GRRIYGVVAFKEWFTYFYMDVWGKGTSVTVSS

SEQ ID NO: 10
HCTASLASSMSVSPGETAKISCGKESIGSRAVQWYQQKPGQPPSLITYNN
QDRPAGVPERFSASPDFRPGTTATLTITNVDAEDEADYYCHIYDARGGTN
WVFDRGTTLTVL

SEQ ID NO: 11
QVEILQESGPGLVKPSETLSLTCNVSGTLVRDNYWSWIRQPLGKQPEWIG
YVHDSGDTNYNPSLKSRVHLSLDKSKNLVSLRLTGVTAADSAIYYCATTK
HGRRIYGVVAFKEWFTYFYMDVWGKGTSVTVSS

SEQ ID NO: 12
HCTGSLASSMSVSPGETAKISCGKESIGSRAVQWYQQKPGQPPSLITYNN
QDRPAGVPERFSASPDFRPGTTATLTITNVDAEDEADYYCHIYDARGGTN
WVFDRGTTLTVL

SEQ ID NO: 13
QMQLQESGPGLVKPSETLSLTCSVSGASISDSYWSWFRRSPGKGLEWIGY
VEIKSGDTNYSPSLKSRVNLSLDASKNQVSLSLVAATAADSGKYYCARTL
HGRRIYGIVAFNEWFTYFYMDVWGNGTQVTVSS

SEQ ID NO: 14
HCTASVTSDISVAPGETARISCGKESLGSRAVQWYQHRAGQAPSLIIYNN
QDRPSGIPERFSGSPDSAFGTTATLTITSVEAGDEADYYCHIWDSRVPTK
WVFGGGTTLTVL

SEQ ID NO: 15
QVEILQESGPGLVKPSETLSLTCVVSGASTSGQYWSWIRQSPGKGLEWIG
YRSDSGDANYNPSLKSRVIISLDTSRNQLSLNVTSVTTADTAMYFCARAQ
RGKRIYGVVSLGEYYHYYIMDVWGTGTPVTVSS

SEQ ID NO: 16
QVQLQESGPGLVKPSETLSVTCSVSGDSMNNYYWTWIRQSPGKGLEWIGY
ISDRASATYNPSLNSRVVISRDTSKNQLSLKLNSVTPADTAVYYCATARR
GQRIYGEVSFGEFFYYYSMDVWGKGTAVTVSS

SEQ ID NOs 17-64-Heavy and light chain CDR1, CDR2, and CDR3 sequences:

SEQ ID NO: 17
GNIWS

SEQ ID NO: 18
FVSGEYIEYNPSLKS

SEQ ID NO: 19
TLRARRIYGVIAFGEVYDYHYFDV

SEQ ID NO: 20
GEKSNGARAVQ

SEQ ID NO: 21
NNQDRPS

SEQ ID NO: 22
HIWDSRFPLSWV

SEQ ID NO: 23
NYYWT

SEQ ID NO: 24
YVSDRASATYNPSLKS

SEQ ID NO: 25
ARRGQRIYGEVAFGEFFYYYSMDV

SEQ ID NO: 26
GRQALGSRAVQ

SEQ ID NO: 27
NNQDRPS

SEQ ID NO: 28
HMWDSRSGFSWS

SEQ ID NO: 29
GRQALGSRAVQ

SEQ ID NO: 30
NNQDRPS

SEQ ID NO: 31
HMWDSRSGFSWS

SEQ ID NO: 32
GEESLGSRSVI

SEQ ID NO: 33
NNNDRPS

SEQ ID NO: 34
HIWDSRRPTNWV

SEQ ID NO: 35
DAYWS

SEQ ID NO: 36
YVHHSGDTNYNPSLKR

SEQ ID NO: 37
ALHGKRIYGTVALGELFVYFYMDV

SEQ ID NO: 38
GEESLGSRSVI

SEQ ID NO: 39
NNNDRPS

SEQUENCE LISTING

SEQ ID NO: 40
HIWDSRRPTNWV

SEQ ID NO: 41
DNYWS

SEQ ID NO: 42
YVHDSGDTNYNPSLKSV

SEQ ID NO: 43
TKHGRRIYGVVAFKEWFTYFYMDV

SEQ ID NO: 44
GKESIGSRAVQ

SEQ ID NO: 45
NNQDRPA

SEQ ID NO: 46
HIYDARGGTNWV

SEQ ID NO: 47
DNYW

SEQ ID NO: 48
YVHDSGDTNYNPSLKS

SEQ ID NO: 49
TKHGRRIYGVVAFKEWFTYFYMDV

SEQ ID NO: 50
GKESIGSRA

SEQ ID NO: 51
NNQDRPA

SEQ ID NO: 52
HIYDARGGTNWV

SEQ ID NO: 53
DSYWS

SEQ ID NO: 54
YVEIKSGDTNYSPSLKS

SEQ ID NO: 55
TLHGRRIYGIVAFNEWFTYFYMDV

SEQ ID NO: 56
GEKSLGSRAVQ

SEQ ID NO: 57
NNQDRPS

SEQ ID NO: 58
HIWDSRVPTKWV

SEQ ID NO: 59
GQYWS

SEQ ID NO: 60
YRSDSGDANYNPSLKS

SEQ ID NO: 61
AQRGKRIYGVVSLGEYYHYYIMDV

SEQ ID NO: 62
NYYWT

SEQ ID NO: 63
YISDRASATYNPSLNS

SEQ ID NO: 64
ARRGQRIYGEVSFGEFFYYYSMDV

SEQ ID NO: 65-Light chain variable region sequence:
SEQ ID NO: 65
XXXXSYVRPLSVALGETASISCGRQALGSRAVQWYQHRPGQAPILLIYNN
QDRPSGIPERFSGTPDINFGTRATLTISGVEAGDEADYYCHMWDSRSGFS
WSFGGATRLTVL SEQ ID NOs 66-68-Light chain CDR1, CDR2, and CDR3 sequences:
SEQ ID NO: 66
GRQALGSRAVQ

SEQ ID NO: 67
NNQDRPS

SEQ ID NO: 68
HMWDSRSGESWS

SEQ ID NOs 69 and 70-Germline variable region sequences:
SEQ ID NO: 69
QVQLQESGPGLVKPSETLSLTCTVSGGSISSYYWSWIRQPPGKGLEWIGY
IYYSGSTNYNPSLKSRVTISVDTSKNQFSLKLSSVTAADTAVYYCARTQQ
GKRIYGVVSFGDYYYYYMDVWGKGTTVTVSS SEQ ID NO: 70
SYVLTQPPSVSVAPGQTARITCGGNNIGSKSVHWYQQKPGQAPVLVVYDD
SDRPSGIPERFSGSNSGNTATLTISRVEAGDEADYYCQVWDSSSDHPWVF
GGGTKLTVL

EXAMPLES

Example 1

Characterization of AbV-1-9 Antibodies

To better understand the neutralizing antibody response to HIV-1 and the epitope targeted by AbV1-9 antibodies, members of a large clonal family dominating the gp160-specific IgG memory response from a Glade A-infected patient were isolated. The sequence, binding affinity, neutralizing activity, and recognition of carbohydrates and the V3 loop were determined for the AbV-1-9 antibodies. Assays were carried out to isolate B-cell clones encoding AbV-1-9. The AbV-1-9 clones segregate into two different groups distinguished by sequence, binding affinity, carbohydrate recognition and neutralizing activity. The first group exhibit remarkable potency and breadth despite not binding detectably to protein-free glycans.

Example 2

Determination of $k_d$ Values $K_d$ is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (See, e.g., Chen et al., J. Mol. Biol. 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v)

bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20TH; Packard) is added, and the plates are counted on a TOP-COUNT™ gamma counter (Packard) for ten minutes. Concentrations of each Fab that give less than or equal to 20% of maximal binding are chosen for use in competitive binding assays.

Example 3

Determination of $k_d$ Values $K_d$ is measured using surface plasmon resonance assays using a BIACORE®-2000 or a BIACORE®-3000 (BIAcore, Inc., Piscataway, N.J.) at 25° C. with immobilized antigen CMS chips at ~10 response units (RU). Briefly, carboxymethylated dextran biosensor chips (CMS, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates (kon) and dissociation rates (koff) are calculated using a simple one-to-one Langmuir binding model (BIACORE® Evaluation Software version 3.2) by simultaneously fitting the association and dissociation sensorgrams. The equilibrium dissociation constant (kd) is calculated as the ratio koff/kon. See, e.g., Chen et al., J. Mol. Biol. 293:865-881 (1999). If the on-rate exceeds 106 M-1 s-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

Example 4

HIV Donor Sequencing

Seven aliquots from a biological sample from a patient, each containing about 90,000 cells, were separated into fractions and pairing fidelity was analyzed. The analysis resulted in about 100,000 possible heavy-light chain pairs and about 37,000 high confidence native heavy-light chain pairs using the AbPair technology methods disclosed in PCT/US2014/028925. An aliquot was sequenced with the AbSeq technology methods disclosed in WO2012048341 and WO2012048340.

Example 5

Novel bNAb Bioinformatic Discovery (Intradonor Similarity)

The CDR3 amino acid similarity of AbV1-9 was determined to known bNAbs derived from patient 17 (Ptl 7). Sequences of healthy patients were used to calibrate the threshold of false positives and to develop a similarity cutoff or thresh hold. The phylogenetic relationship of AbV1-9 antibodies was analyzed in relation to known bNAbs using the full amino acid sequence. Other characteristics of selected antibodies were compared to those characteristics of other known bNAb sequence characteristics including the germ line family, mutation level, etc. Result: 7 high confidence heavy and light chain pairs and 2 heavy chains with inferred light chain pairs were found (AbV1-9).

Example 6

Materials and Methods as Used in EXAMPLES 2-5

HIV antibodies are cloned and produced following gp140-specific single B-cell capture. Glycoengineered antibodies are generated by substituting residues at various heavy chain positions. Binding properties of anti-gp140 antibodies to HIV Env proteins are assayed by ELISA, SPR and glycan microarray assays. Neutralization is evaluated using (i) a luciferase-based assay in TZM.bl cells, and (ii) a PBMC-based assay using infection with primary HIV-1 variants. Structures of AbV1-9 bound and unbound to ligand, and GL Fab fragments, are solved by molecular replacement to high resolution.

Single B Cell RT-PCRs and Ig Gene Analyses

Single-cell sorting of gp140$^+$CD19$^+$IgG$^+$ B cells from a patient is performed. PBMCs, cDNA synthesis and nested PCR amplifications of Ig genes are performed. Igk genes expressed by AbV1-9 clonal variants are PCR amplified. All PCR products are sequenced and analyzed for Ig gene usage, CDR3 analyses and number of V$_H$/VK somatic hypermutations. Multiple sequence alignments are performed using the MacVector program with the ClustalW analysis function, and are used to generate dendrograms by the Neighbor Joining method. Alternatively, dendrograms are generated using the UPGMA method.

The germline (GL) precursor gene segments of the AbV1-9 antibodies are identified using IgBLAST and IMGTdVV-QUEST. To build a representative GL ancestor sequence, the IgH and IgL sequences of an antibody containing the fewest somatic hypermutations are aligned to the GL sequences using IgBLAST. The GL IgH sequence is constructed by replacing the mature V$_H$ and Jx gene segments with their GL counterparts and using the 10-996 sequence for the CDRH3 region involving N-region nucleotides and the DH gene segment. The GL IgT, sequence is assembled from the V$_L$ 3-21 *02 and JL3*02 gene segment sequences.

Cloning and Production of Antibodies

Purified digested PCR products were cloned into human Igyi-, or IgX-expressing vectors. Vectors containing IgH and IgX genes are then sequenced and compared to the original PCR product sequences. Site-directed mutagenesis (QuikChange Site-Directed Mutagenesis Kit; Stratagene) is used to produce variant antibodies. To generate His-tagged Fabs, the $V_H$ genes are subcloned into a 6xHis-IgCyl expression vector g ("6xHis" disclosed as SEQ ID NO: 99) to encode the IgG1 Cul domain followed by a 6×-His tag (SEQ ID NO: 99). IgH DNA fragments encoding mutant antibodies are obtained as a synthetic minigene (IDT) and subcloned into Igyi-expressing vectors.

Antibodies and Fab fragments are produced by transient transfection of IgH and IgL expression plasmids into exponentially growing HEK 293T cells (ATCC, CRL-11268) using the polyethyleneimine (PEI)-precipitation method. IgG antibodies are affinity purified using Protein G sepharose beads (GE Healthcare) according to the manufacturer's instructions. Fab fragments are affinity purified using His-Pur™ Cobalt Resin (Thermo scientific) as described below.

HIV-1 Env Proteins

Alanine mutations are introduced into a pYU-2 gp120 vector using the QuikChange Site-Directed Mutagenesis kit (Stratagene) according to the manufacturer's instructions. The same procedure is used to generate double glycan mutants by introducing single alanine mutations in a pYU-2 gp120$^{mutant}$ vector. Site-directed mutations are verified by DNA sequencing.

Expression vectors encoding YU-2 gp140, YU-2 gp120$^{core}$, HXB2c gp120$^{core}$, HXB2c 2CCcore proteins, and YU-2 gp120 mutant proteins are used to transfect HEK 293T cells. To produce high-mannose-only YU-2 gp120 protein, 25 μM kifunensine (Enzo Life Sciences) is added at the time of transfection. Culture supernatants are harvested and concentrated using centrifugation-based filtration devices that allowed buffer exchange of the samples into 10 mM imidazole, 50 mM sodium phosphate, 300 mM sodium chloride; pH 7.4. Proteins are purified by affinity chromatography using HisPur™ Cobalt Resin (Thermo scientific) according to the manufacturer's instructions.

For deglycosylation reactions, 50 μg of HEK 293T cell-produced YU-2 gp120 in PBS is digested overnight at 37° C. with 200 U of PNGase F (New England Biolabs) or 10,000 U of Endo H$_f$ (New England Biolabs) in their respective reaction buffers without denaturing agents. After buffer exchange into PBS using Centrifugal Filters (Amicon® Ultra, Millipore), glycosidase-treated g 120s (200 ng) are examined by SDS-PAGE using a 4-12% NuPAGE gel (Invitrogen) followed by silver staining (Pierce Silver Stain Kit, Thermo Scientific).

ELISAs

High-binding 96-well ELISA plates (Costar) are coated overnight with 100 ng/well of purified gp120 in PBS. After washing, the plates are blocked for 2 h with 2% BSA, 1 μM EDTA, 0.05% Tween-PBS (blocking buffer) and then incubated for 2 h with IgGs at concentrations of 26.7 nM and 7 consecutive 1:4 dilutions in PBS. After washing, the plates are developed by incubation with goat HRP-conjugated anti-human IgG antibodies (Jackson ImmunoReseach) (at 0.8 μg/ml in blocking buffer) for 1 h, and by addition of HRP chromogenic substrate (ABTS solution, Invitrogen). Antibody binding to the selected gp120 overlapping peptides is tested using a previously described peptide-ELISA method.

For competition ELISAs, gp120-coated plates are blocked for 2 h with blocking buffer and then incubated for 2 h with biotinylated antibodies in 1:2 serially diluted solutions of antibody competitors in PBS (IgG concentration range from 5.2 to 667 nM). Plates are developed as described above using HRP-conjugated streptavidin (Jackson ImmunoReseach) (at 0.8 μg/ml in blocking buffer). All experiments are performed at least in duplicate.

Glycan Microarray Analysis

Microarrays are generated by robotically printing glycan probes linked to lipid (neoglycolipids) onto nitrocellulose-coated glass slides at two levels (2 and 5 fmol/spot) in duplicate. Binding assays are performed with microarrays containing 15 neoglycolipids derived from N-glycans of high-mannose and complex-types. In brief, antibodies are tested at 50 μg/ml, and binding is detected with biotinylated anti-human IgG (Vector) followed by AlexaFluor 647-labeled streptavidin (Molecular Probes).

Surface Plasmon Resonance

Experiments are performed using a Biacore T100 (Biacore, Inc.). Briefly, YU-2 gp140 and gp120 proteins are primary amine-coupled on CMS chips (Biacore, Inc.) at a coupling density of 300 RUs. Anti-gp120 IgGs and the germline precursor (GL) are injected over flow cells at 1 μM and 10 μM, respectively, at flow rates of 35 μl/min with 3 min association and 5 min dissociation phases. The sensor surface is regenerated by a 30 sec injection of 10 mM glycine-HCl pH 2.5 at a flow rate of 50 μl/min. Dissociation (ka (s$^{-1}$)), association (k& (M$^{-1}$ s$^{-1}$)) and binding constants ($K_D$, (M) or $K_A$ (M$^{-1}$)) are calculated from kinetic analyses after subtraction of backgrounds using a 1:1 binding model without a bulk reflective index (RI) correction (Biacore T100 Evaluation software).

Neutralization Assays

Virus neutralization is evaluated using a luciferase-based assay in TZM.bl. The HIV-1 pseudoviruses to test contain mostly tier-2 and tier-3 viruses. High-mannose-only pseudoviruses are produced in wild-type cells treated with 25 μM kifunensine (Enzo Life Sciences) or in HEK 293 S GnTI$^{-/-}$ cells. Non-linear regression analysis is used to calculate concentrations at which half-maximal inhibition is observed (IC$_{50}$ values). Neutralization activities are also evaluated with a previously characterized PBMC-based assay using infection with primary HIV-1 variants (n=95) isolated from Glade B-infected donors with known seroconversion dates either between 1985 and 1989 (historical n=14) or between 2003 and 2006 (contemporary, n=21).

Neutralization activity for each antibody is calculated using GraphPad Prism software as area under the best-fit curve, which fits the proportion of viruses neutralized over IC$_{50}$ values ranging from 0.001 to 50 μg/ml. Relative area under the curve (RAUC) values are derived by normalizing all AUC values by the highest value.

Statistical Analyses

Statistical analyses are performed with the GraphPad Prism software. Neutralization potencies in the TZM-bl assay against the selected panel of virus strains versus the apparent binding affinities of the antibodies for gp120 and gp140 are analyzed using a Spearman's correlation test. The Mann Whitney test is used to compare: (i) affinities for gp120/gp140 of antibodies, and (ii) neutralization activities against viruses isolated from historical and contemporary seroconverters.

Crystallization and Structure Determinations

6×-His (SEQ ID NO: 99) tagged AbV1-9 Fabs for crystallization are expressed. Fabs are purified from the supernatants of transiently-transfected HEK 293-6E cells by sequential Ni-NTA affinity (Qiagen) and Superdex200 10/300 (GE Healthcare) size exclusion chromatography. For crystals of the non-ligand bound PGT121 Fab, PGT121 IgG is isolated from the supernatants of transiently-transfected HEK 293-6E cells by Protein A affinity chromatography (Pierce), and Fab fragments are obtained by papain cleavage of the IgG and further purification using Superdex200 10/300 (GE Healthcare) size exclusion chromatography.

Purified Fabs are concentrated to 8-20 mg/mL in PBS buffer. The "ligand bound" AbV1-9 Fab crystals are prepared from a protein sample (final concentration:15 mg/mL) that is mixed with a 3-fold molar excess of NA2 glycan and incubated at 20° C. for 2 hours. Crystallization conditions are screened at 20° C. using a Mosquito® crystallization robot (TTP labs) in 400 nL drops using a 1:1 protein to reservoir ratio. Crystals of non-ligand bound AbV1-9 Fab are obtained in 24% PEG 4,000, 0.1 M Tris-HCl pH 8.5, 10 mM $CuCl_2$ and crystals of ligand bound AbV1-9 Fab grow in 17% PEG 10,000, 0.1M Bis-Tris pH 5.5, 0.1M $CH_3COOHNH_4$. Crystals of AbV1-9 Fab are obtained in 25% PEG 3,350, 0.1 M Bis-Tris pH 5.5, 0.2 M NaCl, and crystals of GL Fab grow in 20% PEG 3,350, 0.24 M sodium malonate pH 7.0, 10 mM $MnCl_2$. Crystals are cryoprotected by soaking in mother liquor containing 20% glycerol or 20% ethylene glycol and subsequently flash-cooled in liquid nitrogen.

Diffraction data are collected at beamline 12-2 on a Pilatus 6M pixel detector (Dectris). Data are indexed, integrated and scaled using XDS. Using the data obtained from the non-ligand bound AbV1-9 Fab crystals, Phenix is used to find a molecular replacement solution for one Fab per asymmetric unit using two search models, the CH-CL domains of PGT128 Fab (PDB code 3PV3) and the VI-1-W domains of 2F5 (PDB code 3 ID J) after omitting residues in the CDRH3 and CDRL3 loops. Subsequently, the non-ligand bound AbV1-9 structures are used as a search model to find molecular replacement solutions for ligand bound AbV1-9 Fabs (one Fab per asymmetric unit), and GL (four Fabs per asymmetric unit).

Iterative refinement (including non-crystallographic symmetry restraints for GL) is performed using Phenix and manually fitting models into electron density maps using Coot. PyMOL is used for molecular visualization and to generate figures of the Fab structures. Buried surface area calculations are performed with Areaimol (CCP4 Suite) using a 1.4 A probe. Fab structures are aligned using the Super script in PyMOL. Pairwise Ca alignments are performed using PDBeFold.

Example 7

Identification of New Unique Variants

Predominance and diversity of AbV1-9 clonotype gp140-specific IgG memory B cells are isolated from a Clade A-infected African donor using YU-2 gp140 trimers as bait. Matching immunoglobulin heavy (IgH) and light (IgL) chain genes corresponding to unique clonal families are identified. Consistent with the high levels of hypermutation in the IgH genes, the amplified Ig genes are highly mutated and carry nucleotide alterations.

New unique variants are expressed and may demonstrate binding to YU-2 gp120 and gp140 by ELISA and surface plasmon resonance (SPR). Unless otherwise noted, the gp120 and gp140 proteins for these and other experiments are expressed in mammalian cells that can attach either a complex-type or a high-mannose N-glycan to a PNGS.

Example 8

Role of V3 Loop in Antigen Recognition

The role of V3 in antigen recognition by AbV1-9 antibodies is examined. ELISAs are performed using HXB2 gp120 core proteins that lack VI-V3 loops ($gp120^{core}$) or retain a portion of V3 (2CC-core), and using a YU-2 gp120 mutant protein carrying a double alanine substitution in the V3 stem ($gp120^{D324\_544}$). The antibodies may show decreased reactivity against variants lacking the V3 loop and $gp120^{GD324\ 544}$ in comparison to intact YU-2 gp120 and may suggest that recognition by AbV1-9 involves protein determinants in the vicinity of the V3 loop. None of the antibodies may bind to overlapping peptides spanning V3, and may suggest the targeted epitopes are discontinuous and/or require a particular conformation not achieved by isolated peptides.

To compare overall glycan recognition by the AbV1-9 antibodies, their binding to YU-2 gp120 treated with PNGase F, which cleaves both complex-type and high-mannose N-glycans is examined. Because gp120 cannot be fully deglycosylated enzymatically unless it is denatured, PNGase F treatment results in partial deglycosylation of natively-folded gp120. Nevertheless, the reactivity of each group of antibodies may differ in that partial deglycosylation of gp120 by PNGase F may decrease the binding activity of AbV1-9 antibodies. Similar experiments are conducted with YU-2 gp120 treated with Endo H, which cleaves high-mannose, but not complex-type, N-glycans, and may affect binding of other antibodies more than AbV1-9 antibodies.

An N-glycan microarray may reveal that a number AbV1-9 antibodies show detectable binding to various complex-type mono- or bi-antennary N-glycans. Epitope mapping experiments are performed with two representative members of each group by competition ELISA. Antibodies may show cross-competition. To further map the targeted epitopes, anti-gp120 antibodies that recognize the crown of the V3 loop, the CD4bs, the co-receptor binding site, a constellation of high-mannose N-glycans (2G12), or the V3 loop and N-linked glycans at positions 301 and 332 are used. Anti-V3 crown antibodies may inhibit binding of some of these antibodies, but not others Example 9

Broad and Potent 11W Neutralization

To evaluate the neutralizing activity of AbV1-9 variants, their ability to inhibit HIV infection of TZM-bl cells is tested using viral strains including R1166.cl, which lacks the PNGS at gp120 position 332. AbV1-9 variants neutralize pseudoviruses and none neutralize the control. Neutralizing activity correlates with affinity for the HIV spike A representative germline version (GL) of the PGT 121/10-1074 antibody clonotype fails to bind g 120/g 140 or neutralize any viruses in the panel, implying that somatic mutation is required for binding and neutralization. Pairing GL light chains with mutated heavy chains fails to rescue binding or neutralization, suggesting that both mutated chains contribute to proper assembly of the antibody paratope.

Next assays are carried out to compare the neutralization activities of AbV1-9 against an extended panel of difficult-to-neutralize pseudoviruses. As anticipated, most viruses bearing amino acid changes at gp120 positions 332 and/or 334 (spanning the Asn332-X-Ser334/Thr334 PNGS) are resistant to neutralization. Mutation at this PNGS accounts for the majority of viruses resistant to neutralization. Comparable neutralization activities are observed for the IgG and Fab forms of AbV1-9, suggesting that bivalency is not critical for their activity.

To evaluate the potential role of complex-type N-glycans on the HIV envelope in neutralization by AbV1-9, highmannose-only virions are produced in two different ways: by assembling pseudoviruses in cells treated with kifunensine, which results in $Man_9GlcNAc_2$N-linked glycans, or by assembly in HEK 293 S $GnTI^{-/-}$ cells, which results in $Man5GlcNAc_2$ N-linked glycans. AbV1-9 neutralize 2 of 3 kifunensine-derived strains equivalently to their counterparts produced in wild-type cells. Two viral strains produced in GnTI $^{-/-}$ cells are equally as sensitive to AbV1-9 as their counterparts produced in wild-type cells. Consistent with previous reports that complex-type N-glycans partially protect the CD4 binding site from antibody binding, the viruses produced in $GnTI^{-/-}$ cells are more sensitive to CD4-binding site antibodies.

Example 10

Newly-Transmitted HIV-1

The activity of AbV1-9 against transmitted founder viruses is tested by evaluating neutralization in a peripheral blood mononuclear cell (PBMC)-based assay using Glade B viruses isolated from a cohort of individuals who seroconverted between 1985 and 1989 (historical, n=14) or between 2003 and 2006 (contemporary, n=25). AbV1-9 are compared with anti-CD4bs bNAbs and other bNAbs including VRCO1, PG9/PG16, b12, 2G12, 4E10 and 2F5. Clustering analyses of neutralization activity shoed segregation into two groups; one group contains the most active HIV neutralizers including the anti-CD4bs and PG9 antibodies. AbV1-9 show exceptional neutralization potency on this Glade B virus panel.

Example 11

Crystal Structures of AbV1-9 and GL

To investigate the structural determinants of the differences between AbV1-9 antibodies, crystal structures of the Fab fragments of AbV1-9 and a representative germline precursor (GL) are determined. Superimposition of the heavy and light chain variable domains ($V_R$ and $V_L$) among the three Fabs show conservation of the backbone structure, with differences limited to small displacements of the CDRH3 and CDRL3 loops of the affinity-matured Fabs relative to GL.

Comparisons are made with the structure of antibodies that recognize $Asn332_{gp120}$- and $Asn301_{gp}120$-linked glycans and V3 and is solved as a complex with an outer domain/mini-V3 loop gp120 expressed in cells that cannot produce complex-type N-glycan-modified proteins.

Example 12

Crystal Structure of AbV1-9-Glycan Complex

Structures of AbV1-9 associated with a complex-type sialylated bi-antennary glycan is solved using crystals obtained under conditions including NA2.

Example 13

Substitution of Glycan-Contacting Antibody Residues Affects Neutralization

To evaluate the contributions of complex-type N-glycan contacting residues identified from the ligand bound AbV1-9 structures, mutant antibodies designed to exchange the complex-type glycan-contacting residues are generated. The glycoengineered antibodies exhibit near-wild-type apparent affinity for YU-2 gp120/gp140 as measured by SPR, demonstrating that the substitutions do not destroy binding to an envelope spike derived from a viral strain neutralized by both AbV1-9. Unlike wild-type AbV1-9, $AbV1-9_{GM}$ show no glycan binding in microarray experiments. Next, a TZM-bl-based assay is used to compare neutralization of the wild-type and glycoengineered antibodies. Viral strains are tested.

Example 14

Passive Transfer of Anti-HIV-1 Neutralizing mAbs In-Vivo

AbV1-9 anti-HIV neutralizing monoclonal antibodies are administered to rhesus macaques and challenged them intrarectally 24h later with either of two different SHIVs. By combining the results obtained from 60 challenged animals, the protective neutralization titer in plasma preventing virus acquisition in 50% of the exposed monkeys is approximately 1:100.

Animal Experiments

The macaques of use in this study are negative for the MEC class I Mamu-A*01 allele. Construction of the R5-tropic SHIVDH12-V3AD8 PCR mutagenesis, with primers corresponding to the 5' and 3' halves of the SHIVAD8EO is employed to introduce these V3 sequences into the genetic background of the pSHIVDH12_CL7 molecular clone, using Platinum PFX DNA polymerase (Invitrogen). Following gel purification, the PCR product is treated with T4 polynucleotide kinase (GibcoBRL) and blunt-end ligated, which is used to transform competent cells.

Viruses

Virus stocks are prepared by first transfecting 293T cells with the SHIVAD8EO or SHIVDH12-V3AD8 molecular clones using Lipofectamine 2000 (Invitrogen, Carlsbad, Calif.). Culture supernatants are collected 48 h later and aliquots stored at −80° C. until use. Concanavalin A-stimulated rhesus PBMCs (2×10$^6$ cells in 500 µl) are infected with transfected cell supernatants by spinoculation for 1 h, mixed with the same number/volume of activated PBMC, and cultures are maintained for at least 12 days with daily replacement of culture medium. Samples of supernatant medium are pooled around the times of peak RT production to prepare individual virus stocks.

Antibodies

Eleven monoclonal antibodies (VRCO1, NIH45-46, 45-46G54W, 45-46m2, 3BNC117, 12A12, 1NC9, and 8ANC195, 10-1074, PGT121, and PGT126) are isolated and produced. DEN3, a dengue virus NS1-specific human IgG1 monoclonal antibody, or control human IgG are used as the negative control antibodies in this study. The monoclonal antibodies to select for pre-exposure passive transfer are administered intravenously 24 h before virus challenge.

Quantitation of Plasma Viral RNA Levels

Viral RNA levels in plasma are determined by real-time reverse transcription-PCR (ABI Prism 7900HT sequence detection system; Applied Biosystems).

Antibody Concentrations in Plasma

The concentrations of administered monoclonal antibodies in monkey plasma are determined by enzyme-linked immunosorbent assay (ELISA) using recombinant HIV-1JRFL gp120 (Progenies Pharmaceuticals) or HIVIIIB (Advanced Biotechnology Inc. Briefly, microtiter plates are coated with HIV-1 gp120 (2 µg/ml) and incubated overnight at 4° C. The plates are washed with PBS/0.05% Tween-20 and blocked with 1%) (vol/vol) BSA. After blocking, serial dilution of antibodies or plasma samples are added to the plate and incubated for 1 h at room temperature. Binding is detected with a goat anti-human IgG F(ab)$_2$ fragments coupled to alkaline phosphatase (Pierce) and visualized with SIGMAFAST OPD (Sigma-Aldrich). The decay half-lives of neutralizing monoclonal antibodies are calculated by a single-exponential decay formula based on the plasma concentrations beginning on day 5 or day 7 post antibody administration.

Neutralization Assays

The in vitro potency of each mAb and the neutralization activity present in plasma samples collected from rhesus macaques are assessed by two types of neutralization assays; 1) TZM-bl entry assay with pseudotyped challenge virus or a 14 day PBMC replication assay with replication competent virus. For the TZM-bl assay, serially diluted mAb or plasma samples are incubated with pseudotyped viruses, expressing env gene derived from SHIVAD8EO or SHIVDH12 V3AD8 and prepared by cotransfecting 293T cells with pNLenvl and pCMV vectors expressing the respective envelope proteins. The 50%>neutralization inhibitory dose ($IC_{50}$) titer is calculated as the dilution causing a 50%>reduction in relative luminescence units (RLU) compared with levels in virus control wells after subtraction of cell control RLU. The neutralization phenotype (tier levels) of the SHIVDH12_V3AD8 molecular clone is determined by TZM-bl cell assay using plasma samples from a cohort study, which exhibit a wide range of neutralizing activities against subtype B HIV-1.

Determinations of Animal Protective Titers and Statistical Analyses.

Calculation of the neutralizing titer in plasma against each R5 SHIV, resulting in the prevention of virus acquisition of 50 or 80% of the virus-challenged animals, is performed. Probit regression is used to model the relationship between the titers in plasma required to confer sterilizing immunity in vivo using all passively immunized monkeys, with p-values from this model based on Likelihood ratio Tests. Plasma titers needed for different levels of in vivo protection (33%, 50%, 80%, 90%, and 95%>) are determined from the probit model estimates and the method of bootstrapping is used to construct 90%>confidence intervals.

The protocol for passive transfer experiments is to administer decreasing amounts of neutralizing mAbs intravenously and challenge animals intrarectally 24 h later. The goal is to block virus acquisition, coupled with the knowledge that repeated administrations of humanized anti-HIV mAbs to individual macaques could reduce their potency and/or possibly induce anaphylactic responses, a SHIV challenge dose of sufficient size to establish an in vivo infection following a single inoculation is chosen.

As a control for the first passive transfer experiment, an anti-dengue virus NS1 IgG1 mAb is administered intravenously to animals, which are challenged with SHIVAD8EO 24h later. VRCO1 is the first anti-HIV-1 neutralizing mAb tested for protection against virus acquisition and is administered to two macaques at a dose of 50 mg/kg. One (DEGF) of the two inoculated macaques is completely protected from the SHIVAD8EO challenge. The other recipient of 50 mg/kg VRCO1 (DEH3) becomes infected, but peak plasma viremia. Two additional macaques are administered lower amounts (20 mg/kg) of VRCO1 and are not protected from the SHIVAD8EO challenge. The capacity of VRCO1 and AbV1-9 mAbs to block SHIVDH12-V3AD8 acquisition is similarly evaluated.

Plasma samples collected at various times from passively transferred macaques are analyzed by HIV-1 gp120 ELISA to determine neutralizing mAb concentrations. In general, the plasma concentrations of each mAb at the time of challenge (24 h following antibody administration) correlates with the dose of antibody administered.

Neutralization titers are measured on plasma samples collected 24h following mAb administration when the macaques are challenged with SHIVAD8EO or SHIVDH12-V3AD8. The neutralization titers measured in plasma needed to prevent virus acquisition in 50% of challenged monkeys is then calculated.

Example 15

Administration of Neutralizing mAbs to Chronically Infected HIV In-Vivo Models

The neutralization activities of the broadly acting neutralizing mAbs against SHIVAD8EO are initially determined in the TZM-bl cell system against SHIVAD8EO. Their capacities to block virus acquisition or to control plasma viremia in chronically infected animals challenged with the R5-tropic SHIVAD8EO are assessed by monitoring plasma viral loads and cell-associated viral nucleic acids; levels of CD4+ T cell subsets are measured by flow cytometry. SGA analyses of circulating viral variants and the determination of antibody levels in plasma. Plasma concentration of NAbs is determined by measuring neutralizing activity against HIV-1 pseudovirus preparations only susceptible to either 10-1074 or 3BNC117.

Example 16

454 Sequencing Library Preparation

Reverse transcription is performed with 10 µL total RNA and 2 µL RT primer mix (50 µM oligo-dT and 25 µM random hexamer). The mixture is heated at 95° C. for 1 min, 65° C. for 5 min, then cooled on ice for 1 min. For each reaction, a mix is prepared with 4 µL 5×FS buffer, 1 µL 10 mM dNTP mix, 1 µL 0.1 M DTT, 1 µL RNase inhibitor (Enzymatics), and 1 µL SuperScript III RT (Invitrogen). This mix is added to the reaction and incubated at 25° C. for 10 min, 35° C. for 5 min, 55° C. for 45 min, and 85° C. for 5 min. RNA/DNA hybrid is removed by adding 4 µL *E. coli* RNase H (Enzymatics). PCR reactions are assembled using 13.75 µL water, 5 µL cDNA, 5 µL 5×HF buffer, 0.5 µL 10 mM dNTP, 0.25 µL of each 100 µM primer stock, and 0.25 µL Phusion Hot Start. The reaction is cycled at 98° C. (60s), 24 cycles of 98° C. (10s), 62° C. (20s), and 72° C. (20s), with a final extension at 72° C. (5 min). Samples are purified on a QIAquick column and run on a 2% agarose E-gel. The desired bands are purified using the Qiagen MinElute gel extraction kit, eluted twice with 10 µL EB buffer, and quantitated on a 2100 Bioanalyzer. Samples are sent to SeqWright for 454 sequencing, which is performed per manufacturer's instructions.

Example 17

Pseudovirus Production and Neutralization Assays

To produce pseudoviruses, plasmids encoding Env are co-transfected with an Env-deficient genomic backbone plasmid (pSG3ΔEnv) in a 1:2 ratio with the transfection reagent Fugene 6 (Promega). Pseudoviruses are harvested 72 hours post transfection for use in neutralization assays. Neutralizing activity is assessed using a single round of replication pseudovirus assay and TZM-bl target cells, as described previously.

Example 18

Human Specimens

Peripheral blood mononuclear cells (PBMCs) are obtained from donor 17, an HIV-1 infected donor from an cohort. All human samples are collected with informed consent under clinical protocols approved by the appropriate institutional review board.

Example 19

Cell Sorting and RNA Extraction

Frozen vials of 10×10$^6$ PBMCs are thawed and washed before staining with Pacific Blue labeled anti-CD3 (UCHT1), Pacific Blue labeled anti-CD14 (M5E2), FITC labeled anti-CD19 (HIB19), PE-Cy5 labeled antiCD10 (HI10a), PE labeled anti-CD27 (M-T271), and APC labeled anti-CD21 (B-1y4), all from BD Biosciences. Sorts are performed on a high speed BD FACSAria into miRVana lysis buffer (Ambion). Immature B cells, exhausted tissue-like memory, activated mature B cells, resting memory B cells, and short-lived peripheral plasmablasts are stained using previously described markers[31]. Total RNA from the cells is then extracted using the miRVana RNA extraction kit (Ambion) according to manufacturer's instructions and quantitated on a 2100 Bioanalyzer (Agilent).

Example 20

Antibody and Protein Expression and Purification

Antibody sequences are synthesized and cloned into previously described heavy and light chain vectors. The plasmids are co-transfected (1:1 ratio) in either HEK 293T or 293 FreeStyle cells using Fugene 6 (Promega) or 293fectin (Invitrogen), respectively. Transfections are performed according to the manufacturer's protocol and antibody supernatants are harvested four days following transfection. Antibodies produced in 293T cells are quantified by ELISA and used directly in neutralization assays. Antibodies produced in 293 freestyle cells are further purified over a protein A column. Mutations are introduced by site-directed mutagenesis using the QuikChange site-directed mutagenesis kit (Stratagene). Recombinant gp120 proteins are transfected in 293 FreeStyle cells using 293fection (Invitrogen) and purified with Galanthus nivalis lectin column followed by size exclusion using Superdex 300 26/60 (GE Healthcare).

Example 21

Cell Surface Binding Assays

Titrating amounts of mAbs are added to HIV-1 Env-transfected 293T cells and incubated for lh at 4° C. in 1×PBS. Following washing, cells are fixed with 2% PFA (PolySciences) for 20 min at RT. The cells are then washed and stained with a 1:200 dilution of phycoerythrin-conjugated goat anti-human IgG F(ab')$_2$ (Jackson) for 1 h at RT. Binding is analyzed using flow cytometry. Binding competitions are performed by titrating amounts of competitor monoclonal antibodies before adding biotinylated antibody at a concentration required to give IC$_{70}$ and then measuring binding with phycoerythrin-labeled streptavidin (Invitrogen). FlowJo software is used for data interpretation.

Example 22

ELISA Assays

Binding by ELISA is performed. Briefly, plates are coated with goat anti-human IgG Fc (Pierce) or with gp120 and binding is detected using goat anti-human IgGF(ab')$_2$ conjugated to alkaline phosphatase (Pierce). For binding to gp120 extracted from lysed virions, plates are coated with 5 ng/μL of sheep D7324 anti-gp120 antibody (Aalto Bio reagents). Virus supernatants are lysed using a final concentration of 1% NP-40 and incubated on coated plates for 2h at 37° C. Detection is measured using goat anti-human IgG F(ab')$_2$ conjugated to alkaline phosphatase (Pierce). Antibody concentration is calculated by linear regression using a standard concentration curve of purified IgG protein.

Example 23

AbV1-9 Germline Fab Expression, Purification, Crystallization and X-ray Diffraction Analysis AbV1-9 germline Fabs are produced in HEK 293T cells and purified. Briefly, three days after transfection with the heavy and light chain genes, the expression media is harvested and the secreted Fab is purified via an anti-human light chain affinity matrix (CaptureSelect Fab 2; BAC), followed by cation exchange chromatography and size-exclusion chromatography. X-ray diffraction quality crystals are obtained in a condition containing 0.2 M magnesium acetate, 20% w/v PEG 8000, 0.1 M sodium cacodylate, pH 6.5.Before mounting and flash freezing the crystals in liquid nitrogen, the mother liquor is supplemented with 20% glycerol for cryo-protection. A complete dataset is collected. Data processing is performed using XDS. The PGT121germline structure is solved using PHASER in space groups P212121 with the PGT123 Fab structure as a search model. Refinement is performed using a combination of PHENIX and COOT.

Example 24

Raw Data Processing: VDJ Alignment and Clone Definition

Raw sequencing data are processed using in-house tools written in python. Reads are split into barcodes, size-filtered, and aligned to IMGT's germline VDJ reference database. The scores are kept low for sequences that are very highly mutated. The V region is aligned first, then removed, followed by J, then removed, followed by D. The IMGT-defined CDR3 sequence of each read is then extracted. The CDR3 sequences are sorted by abundance and clustered with USEARCH5.1. Finally, each CDR3 sequence is aligned to the target antibody sequences of AbV1-9 to determine a divergence value from these antibodies.

Example 25

Antibody Variant Identification and Analysis

The divergence-mutation plots are used as a tool to identify reads that are similar to known antibodies. High-identity clusters of sequences and clusters that are above background are manually identified and used as input for a phylogeny inference with Immunitree. Immunitree implements a Bayesian model of somatic hypermutation of clones, including probabilistic models of SHM and sequencing error and performs Markov chain Monte Carlo over the tree structure, birth/death times of the subclones, birth/death, mutation, and sequencing error rates, subclone consensus sequences, and assignment of reads to nodes. The tree structure is also used for multiple computations and to overlay different information. The selection pressure that a given node has experienced is estimated using the BASELINe algorithm. It performs a Bayesian estimation of selection pressure by comparing the observed number of replacement/silent mutations in the CDRs/FWRs of the node consensus sequence.

Example 26

Recovery of Known Low Frequency $V_H V_L$ Pairs from an HIV Elite Controller

As a further validation of the pairing sensitivity and accuracy of the assay, a sample was processed where several rare (<1 cell in 10,000) native $V_H V_L$ pairings are already and publicly known. Peripheral B-cells from an HIV elite controller patient were obtained whose memory B cells have been mined heavily in recent years for antibodies displaying HIV neutralization activity. 350,000 B-cells were processed to generate a total of 38,620 filtered $V_H V_L$ pairs. Interestingly, this individual showed a greater proportion of IgG than the previous healthy sample (FIG. 7A) or typical healthy peripheral B-cell repertoires. $V_H$ sequences from this dataset were compared to all reported broadly neutralizing antibodies (bNAbs) from this individual including PGT121 and found eight close or identical $V_H$ sequences, indicating that this family of bNAbs represents less than 0.03% of circulating B-cells. Crucially, all light chains paired to these heavy chains were of the expected and similarly rare bNAb lineage, displaying the same Igλ-V3-21/J3 rearrangement and hallmark triple codon insertion as previously reported, supporting the high accuracy and sensitivity of our method. Furthermore, on a phylogenetic tree of all known and newly generated PGT121-like $V_H V_L$ pairs from this individual (FIG. 7B), the $V_H$ and $V_L$ trees show strikingly similar topology with paired $V_H$ and $V_L$ sequences occupying mirror-like positions, likely reflecting shared phylogenetic history. The variant pairs discovered here fit well with this rule. Interestingly, two published antibodies PGT122 and PGT123 appear as exceptions; support for these two pairings was not found, but instead PGT122$V_H$: PGT123$V_L$-like, and PGT123$V_H$:PGT122$V_L$-like pairs were found, addressing the unverified pairing in the original report. DNA encoding the complete V(D)J regions of 8 novel PGT-like $V_H V_L$ pairs were synthesized, expressed the antibodies as full IgG and tested their ability to neutralize multiple pseudostrains of HIV (FIG. 7C). The antibodies expressed well and all showed strong neutralizing activity against the virus, demonstrating the utility of our approach in rapidly generating natively paired functional antibody variants from a relevant biological sample.

Example 27

Human Samples

The blood sample for healthy repertoire validation was collected under the approval of the Personal Genome Project. PBMCs for the HIV bNAb experiment were obtained from donor 17, an HIV-1 infected donor from the IAVI Protocol G cohort. All human HIV samples were collected with written informed consent under clinical protocols approved by the Republic of Rwanda National Ethics Committee, the Emory University Institutional Review Board, the University of Zambia Research Ethics Committee, the Charing Cross Research Ethics Committee, the UVRI Science and Ethics Committee, the University of New South Wales Research Ethics Committee. St. Vincent's Hospital and Eastern Sydney Area Health Service, Kenyatta National Hospital Ethics and Research Committee, University of Cape Town Research Ethics Committee, the International Institutional Review Board, the Mahidol University Ethics Committee, the Walter Reed Army Institute of Research (WRAIR) Institutional Review Board, and the Ivory Coast Comite "National d'Ethique des Sciences de la Vie et de la Sante" (CNESVS). Cryopreserved, dissociated resected ovarian adenocarcinoma from a single donor was obtained from Conversant Biologics with written informed consent under an IRB approved protocol.

Example 28

Anti-HIV Chimeric Antigen Receptor (CAR) T Cells

Genes for anti-HIV single-chain variable fragment (sFv or scFv) versions of AbV-1-9 are created by the synthesis of codon-optimized sequences for the heavy and light chains, which are separated by a linker, such as a (GGGGS)3 linker (SEQ ID NO: 71). For each anti-HIV antibody, a scFv gene is included in a vector encoding a CAR, such as one encoding a CAR comprising a 4-1BB-derived signaling domain fused to the CD3 ζ signaling domain to create an anti-HIV CAR-encoding vector, such as a lentiviral vector. Primary CD4$^+$ and CD8$^+$ T cells are transduced with the anti-HIV CAR-encoding vector.

Characterization of T Cells Expressing Anti-HIV CARs

Enriched anti-HIV CAR-transduced T cells are tested for their capacity to proliferate in response to HIV-1 infected cells. The anti-HIV CAR-transduced T cells are labeled with CellTrace Violet and then are co-cultured with HIV-1$_{NL4-3}$-infected cells (such as Jurkat, SupT1, HEK293T, or HeLa cells). The proliferation of anti-HIV CAR-transduced T cells is measured by flow cytometry, and is shown to be increased over non-transduced T cells.

Enriched anti-HIV CAR-transduced T cells are tested for their ability to mediated specific killing of HIV-1 infected cells. Anti-HIV CAR-transduced T cells are assayed in a chromium release assay when co-cultured with HIV-1-infected target cells. Specific lysis of HIV-1 infected cells is measured, and specific lysis is shown to occur due to the anti-HIV CAR-transduced T cells. Treatment with T cells expressing CARs T cells from a subject infected with HIV are transduced with anti-HIV CAR vectors to express anti-HIV CARs. The anti-HIV CAR-transduced Tcells are administered to the subject. Cells expressing the target antigen of the anti-HIV CAR are killed by the anti-HIV CAR-transduced T cells, which reduces or clears the HIV infection, and/or reduces the symptoms thereof, in the subject.

What is claimed is:

1. An antibody or antigen-binding fragment thereof that specifically binds to an N-glycan epitope of HIV-1 Env, comprising:
   (a) a heavy chain variable domain ($V_H$) comprising: a CDR-H1 comprising the amino acid sequence of SEQ ID NO: 23, a CDR-H2 comprising the amino acid sequence of SEQ ID NO: 24, and a CDR-H3 comprising the amino acid sequence of SEQ ID NO: 25; and
   (b) a light chain variable domain ($V_L$) comprising: a CDR-L1 comprising the amino acid sequence of SEQ ID NO: 26, a CDR-L2 comprising the amino acid sequence of SEQ ID NO: 27, and a CDR-L3 comprising the amino acid sequence of SEQ ID NO: 28.

2. The antibody or antigen-binding fragment of claim 1, comprising:
   (a) a $V_H$ sequence having the amino acid sequence of SEQ ID NO: 3 or up to 5% variation thereof, wherein CDR-H1 comprises the amino acid sequence of SEQ ID NO: 23, CDR-H2 comprises the amino acid sequence of SEQ ID NO: 24, and CDR-H3 comprises the amino acid sequence of SEQ ID NO: 25, and wherein CDR-H1, CDR-H2, and CDR-H3 are invariant; and
   (b) a $V_L$ sequence having the amino acid sequence of SEQ ID NO: 4 or up to 5% variation thereof, wherein CDR-L1 comprises the amino acid sequence of SEQ ID NO: 26, CDR-L2 comprises the amino acid sequence of SEQ ID NO: 27, and CDR-L3 comprises the amino acid sequence of SEQ ID NO: 28, and wherein CDR-L1, CDR-L2, and CDR-L3 are invariant;
wherein the antibody or antigen-binding fragment retains the ability to bind to HIV-1.

3. The antibody or antigen-binding fragment of claim 1, comprising a $V_H$ sequence having the amino acid sequence of SEQ ID NO: 3 and a $V_L$ sequence having the amino acid sequence of SEQ ID NO: 4.

4. The antibody or antigen-binding fragment of claim 1, wherein the antibody or antigen-binding fragment binds to or is capable of binding to an N-glycan epitope of HIV-1 Env with an affinity of 1 nM or less.

5. The antibody or antigen-binding fragment of claim 1, wherein the antibody or antigen-binding fragment inhibits the infectivity of two or more strains or subtypes of HIV-1.

6. The antibody or antigen-binding fragment of claim 1, wherein the HIV-1 is group M HIV-1.

7. The antibody of claim 1, wherein the antibody is glycoengineered to modify the oligosaccharides in the Fc region, and wherein the antibody has increased ADCC effector function as compared to a non-glycoengineered antibody.

8. The antibody of claim 1, wherein the antibody is a monoclonal antibody.

9. The antibody of claim 1, wherein the antibody is a human antibody, a humanized antibody, or a chimeric antibody.

10. The antibody of claim 9, wherein the antibody is a full-length IgG class antibody.

11. The antigen-binding fragment of claim 1, wherein the antigen-binding fragment is a single chain variable fragment (scFv).

12. An isolated nucleic acid encoding the antibody or antigen-binding fragment of claim 1.

13. A vector comprising the nucleic acid of claim 12.

14. An isolated host cell comprising the vector of claim 13.

15. A method for making an antibody or antigen-binding fragment that specifically binds to an N-glycan epitope of HIV-1 Env, the method comprising:
   (a) culturing the cell of claim 14 in a medium under conditions permitting expression of a polypeptide encoded by the vector and assembling of an antibody or antigen-binding fragment thereof; and
   (b) purifying the antibody or antigen-binding fragment from the cultured cell or the medium of the cell.

16. An immunoconjugate comprising the antibody or antigen-binding fragment of claim 1 and a therapeutic agent.

17. A fusion protein or conjugate comprising the antibody or antigen-binding fragment of claim 1.

18. A pharmaceutical formulation comprising the antibody or antigen-binding fragment of claim 1 and a pharmaceutically acceptable carrier.

19. A method of neutralizing HIV-1, comprising administering to the individual an effective amount of the antibody or antigen-binding fragment of claim 1.

20. A method of neutralizing HIV-1, comprising administering to the individual an effective amount of the immunoconjugate of claim 16.

21. A method of detecting HIV-1, comprising
   (a) contacting a sample with the antibody or antigen-binding fragment of claim 1 under conditions permissive for formation of a complex between the antibody or antigen-binding fragment and HIV-1 present in the sample, and
   (b) detecting the presence or absence of the complex, optionally by an immunodetection method.

22. A kit comprising a pharmaceutically acceptable dosage unit of a pharmaceutically effective amount of at least one isolated antibody or antigen-binding fragment according to claim 1.

23. A kit comprising at least one isolated antibody or antigen-binding fragment according to claim 1, and one or more detection reagents that specifically bind to the antibody or antigen-binding fragment.

* * * * *

SEQUENCE LISTING

<160> NUMBER OF SEQ ID NOS: 124

<210> SEQ ID NO 1
<211> LENGTH: 131
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Gln Met Gln Leu Gln Glu Ser Gly Pro Gly Leu Val Lys Pro Ser Glu
1               5                   10                  15

Thr Leu Ser Leu Thr Cys Val Val Ser Gly Gly Ser Val Ser Gly Asn
            20                  25                  30

Ile Trp Ser Trp Ile Arg Gln Ser Pro Gly Lys Gly Pro Glu Trp Val
        35                  40                  45

Gly Phe Val Ser Gly Glu Tyr Ile Glu Tyr Asn Pro Ser Leu Lys Ser
    50                  55                  60

Arg Leu Thr Ile Ser Arg Asp Thr Ser Lys Asn Gln Leu Ser Leu Thr
65                  70                  75                  80

Leu Arg Ser Val Thr Ala Ala Asp Thr Ala Met Tyr Tyr Cys Ala Lys
                85                  90                  95

Thr Leu Arg Ala Arg Arg Ile Tyr Gly Val Ile Ala Phe Gly Glu Val
            100                 105                 110

Tyr Asp Tyr His Tyr Phe Asp Val Trp Gly Lys Gly Thr Met Val Thr
        115                 120                 125

Val Ser Ser
    130

<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

Thr Asp Ser Val Ala Ser Asp Val Ala Met Ser Val Ala Pro Gly Asp
1               5                   10                  15

Thr Ala Thr Ile Ser Cys Gly Glu Lys Ser Asn Gly Ala Arg Ala Val
            20                  25                  30

Gln Trp Tyr Gln Gln Lys Pro Gly Gln Ala Pro Val Leu Ile Ile Tyr
        35                  40                  45

Asn Asn Gln Asp Arg Pro Ser Gly Ile Pro Glu Arg Phe Ser Ala Ser
    50                  55                  60

Pro Asp Ala Gly Phe Gly Thr Thr Ala Thr Leu Thr Ile Ser Arg Val
65                  70                  75                  80

Glu Ala Gly Asp Glu Ala Asp Tyr Tyr Cys His Ile Trp Asp Ser Arg
                85                  90                  95

Phe Pro Leu Ser Trp Val Phe Ala Gly Gly Thr Lys Leu Thr Val Leu
            100                 105                 110

<210> SEQ ID NO 3
<211> LENGTH: 132
<212> TYPE: PRT
<213> ORGANISM: Artificial Sequence
<220> FEATURE:
<223> OTHER INFORMATION: Description of Artificial Sequence: Synthetic -continued

```
<400> SEQUENCE: 3

Gln Val Gln Leu Gln Glu Ser Gly Pro Gly Leu Val Lys Pro Ser Glu
1               5                   10                  15

Thr Leu Ser Val Thr Cys Ser Val Ser Gly Asp Ser Met Asn Asn Tyr
            20                  25                  30

Tyr Trp Thr Trp Ile Arg Gln Ser Pro Gly Lys Gly Leu Glu Trp Ile
        35                  40                  45

Gly Tyr Val Ser Asp Arg Ala Ser Ala Thr Tyr Asn Pro Ser Leu Lys
    50                  55                  60

Ser Arg Val Val Ile Ser Arg Asp Thr Ser Lys Asn Gln Leu Ser Leu
65                  70                  75                  80

Lys Leu Asn Ser Val Thr Leu Ala Asp Thr Ala Val Tyr Tyr Cys Ala
                85                  90                  95

Thr Ala Arg Arg Gly Gln Arg Ile Tyr Gly Glu Val Ala Phe Gly Glu
            100                 105                 110

Phe Phe Tyr Tyr Tyr Ser Met Asp Val Trp Gly Lys Gly Thr Ala Val
        115                 120                 125

Thr Val Ser Ser
    130

<210> SEQ ID NO 4
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Ser Val Thr Ser Phe Val Arg Pro Leu Ser Val Ala Leu Gly Glu
1               5                   10                  15

Thr Ala Ser Ile Ser Cys Gly Arg Gln Ala Leu Gly Ser Arg Ala Val
            20                  25                  30

Gln Trp Tyr Gln His Arg Pro Gly Gln Ala Pro Val Leu Leu Ile Tyr
        35                  40                  45

Asn Asn Gln Asp Arg Pro Ser Gly Ile Pro Glu Arg Phe Ser Gly Thr
    50                  55                  60

Pro Asp Ile Asn Phe Gly Thr Arg Ala Thr Leu Thr Ile Ser Gly Val
65                  70                  75                  80

Glu Ala Gly Asp Glu Ala Asp Tyr Tyr Cys His Met Trp Asp Ser Arg
                85                  90                  95

Ser Gly Phe Ser Trp Ser Phe Gly Gly Ala Thr Arg Leu Thr Val Leu
            100                 105                 110

<210> SEQ ID NO 5
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Leu Gln Leu Gln Glu Ser Gly Pro Gly Leu Val Lys Pro Pro Glu
1               5                   10                  15

Thr Leu Ser Leu Thr Cys Ser Val Ser Gly Ala Ser Ile Asn Asp Ala
            20                  25                  30
```

```
Tyr Trp Ser Trp Ile Arg Gln Ser Pro Gly Lys Arg Pro Glu Trp Val
            35                  40                  45

Gly Tyr Val His His Ser Gly Asp Thr Asn Tyr Asn Pro Ser Leu Lys
    50                  55                  60

Arg Arg Val Thr Phe Ser Leu Asp Thr Ala Lys Asn Glu Val Ser Leu
65                  70                  75                  80

Lys Leu Val Ala Leu Thr Ala Ala Asp Ser Ala Val Tyr Phe Cys Ala
                85                  90                  95

Arg Ala Leu His Gly Lys Arg Ile Tyr Gly Thr Val Ala Leu Gly Glu
            100                 105                 110

Leu Phe Val Tyr Phe His Met Asp Val Trp Gly Lys Gly Thr Ala Val
            115                 120                 125

Thr Val Ser Ser
            130

<210> SEQ ID NO 6
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

His Cys Thr Gly Ala Val Ser Ser Phe Val Ser Val Ala Pro Gly Gln
1               5                   10                  15

Thr Ala Arg Ile Thr Cys Gly Glu Glu Ser Leu Gly Ser Arg Ser Val
            20                  25                  30

Ile Trp Tyr Gln Gln Arg Pro Gly Gln Ala Pro Ser Leu Ile Ile Tyr
            35                  40                  45

Asn Asn Asn Asp Arg Pro Ser Gly Ile Pro Glu Arg Phe Ser Gly Ser
    50                  55                  60

Pro Gly Ser Thr Phe Gly Thr Thr Ala Thr Leu Thr Ile Thr Ser Val
65                  70                  75                  80

Glu Ala Gly Asp Glu Ala Asp Tyr Tyr Cys His Ile Trp Asp Ser Arg
                85                  90                  95

Arg Pro Thr Asn Trp Val Phe Gly Gly Gly Thr Thr Leu Thr Val Leu
            100                 105                 110

<210> SEQ ID NO 7
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Leu Gln Leu Gln Glu Ser Gly Pro Gly Leu Val Lys Pro Glu
1               5                   10                  15

Thr Leu Ser Leu Thr Cys Ser Val Ser Gly Ala Ser Ile Asn Asp Ala
            20                  25                  30

Tyr Trp Ser Trp Ile Arg Gln Ser Pro Gly Lys Arg Pro Glu Trp Val
            35                  40                  45

Gly Tyr Val His His Ser Gly Asp Thr Asn Tyr Asn Pro Ser Leu Lys
    50                  55                  60

Arg Arg Val Thr Phe Ser Leu Asp Thr Ala Lys Asn Glu Val Ser Leu
65                  70                  75                  80
```

```
Lys Leu Val Ala Leu Thr Ala Ala Asp Ser Ala Val Tyr Phe Cys Ala
                85                  90                  95

Arg Ala Leu His Gly Lys Arg Ile Tyr Gly Thr Val Ala Leu Gly Glu
            100                 105                 110

Leu Phe Val Tyr Phe Tyr Met Asp Val Trp Gly Lys Gly Thr Ala Val
        115                 120                 125

Thr Val Ser Ser
    130

<210> SEQ ID NO 8
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

His Cys Thr Gly Ala Val Ser Ser Phe Val Ser Val Ala Pro Gly Gln
1               5                   10                  15

Thr Ala Arg Ile Thr Cys Gly Glu Glu Ser Leu Gly Ser Arg Ser Val
            20                  25                  30

Ile Trp Tyr Gln Gln Arg Pro Gly Gln Ala Pro Ser Leu Ile Ile Tyr
        35                  40                  45

Asn Asn Asn Asp Arg Pro Ser Gly Ile Pro Glu Arg Phe Ser Gly Ser
50                  55                  60

Pro Gly Ser Thr Phe Gly Thr Thr Ala Thr Leu Thr Ile Thr Ser Val
65                  70                  75                  80

Glu Ala Gly Asp Glu Ala Asp Tyr Tyr Cys His Ile Trp Asp Ser Arg
                85                  90                  95

Arg Pro Thr Asn Trp Val Phe Gly Glu Gly Thr Thr Leu Thr Val Leu
            100                 105                 110

<210> SEQ ID NO 9
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val His Leu Gln Glu Ser Gly Pro Gly Leu Val Lys Pro Ser Glu
1               5                   10                  15

Thr Leu Ser Leu Thr Cys Asn Val Ser Gly Thr Leu Val Arg Asp Asn
            20                  25                  30

Tyr Trp Ser Trp Ile Arg Gln Pro Leu Gly Lys Gln Pro Glu Trp Ile
        35                  40                  45

Gly Tyr Val His Asp Ser Gly Asp Thr Asn Tyr Asn Pro Ser Leu Lys
    50                  55                  60

Ser Arg Val His Leu Ser Leu Asp Lys Ser Lys Asn Leu Val Ser Leu
65                  70                  75                  80

Arg Leu Thr Gly Val Thr Ala Ala Asp Ser Ala Ile Tyr Tyr Cys Ala
                85                  90                  95

Thr Thr Lys His Gly Arg Arg Ile Tyr Gly Val Val Ala Phe Lys Glu
            100                 105                 110

Trp Phe Thr Tyr Phe Tyr Met Asp Val Trp Gly Lys Gly Thr Ser Val
        115                 120                 125
```

Thr Val Ser Ser
    130

<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

His Cys Thr Ala Ser Leu Ala Ser Ser Met Ser Val Ser Pro Gly Glu
1               5                   10                  15

Thr Ala Lys Ile Ser Cys Gly Lys Glu Ser Ile Gly Ser Arg Ala Val
            20                  25                  30

Gln Trp Tyr Gln Gln Lys Pro Gly Gln Pro Ser Leu Ile Ile Tyr
        35                  40                  45

Asn Asn Gln Asp Arg Pro Ala Gly Val Pro Glu Arg Phe Ser Ala Ser
    50                  55                  60

Pro Asp Phe Arg Pro Gly Thr Thr Ala Thr Leu Thr Ile Thr Asn Val
65                  70                  75                  80

Asp Ala Glu Asp Glu Ala Asp Tyr Tyr Cys His Ile Tyr Asp Ala Arg
                85                  90                  95

Gly Gly Thr Asn Trp Val Phe Asp Arg Gly Thr Thr Leu Thr Val Leu
            100                 105                 110

<210> SEQ ID NO 11
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val His Leu Gln Glu Ser Gly Pro Gly Leu Val Lys Pro Ser Glu
1               5                   10                  15

Thr Leu Ser Leu Thr Cys Asn Val Ser Gly Thr Leu Val Arg Asp Asn
            20                  25                  30

Tyr Trp Ser Trp Ile Arg Gln Pro Leu Gly Lys Gln Pro Glu Trp Ile
        35                  40                  45

Gly Tyr Val His Asp Ser Gly Asp Thr Asn Tyr Asn Pro Ser Leu Lys
    50                  55                  60

Ser Arg Val His Leu Ser Leu Asp Lys Ser Lys Asn Leu Val Ser Leu
65                  70                  75                  80

Arg Leu Thr Gly Val Thr Ala Ala Asp Ser Ala Ile Tyr Tyr Cys Ala
                85                  90                  95

Thr Thr Lys His Gly Arg Arg Ile Tyr Gly Val Val Ala Phe Lys Glu
            100                 105                 110

Trp Phe Thr Tyr Phe Tyr Met Asp Val Trp Gly Lys Gly Thr Ser Val
        115                 120                 125

Thr Val Ser Ser
    130

<210> SEQ ID NO 12
<211> LENGTH: 112
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 12

His Cys Thr Gly Ser Leu Ala Ser Ser Met Ser Val Ser Pro Gly Glu
1               5                   10                  15

Thr Ala Lys Ile Ser Cys Gly Lys Glu Ser Ile Gly Ser Arg Ala Val
            20                  25                  30

Gln Trp Tyr Gln Gln Lys Pro Gly Gln Pro Ser Leu Ile Ile Tyr
        35                  40                  45

Asn Asn Gln Asp Arg Pro Ala Gly Val Pro Glu Arg Phe Ser Ala Ser
 50                  55                  60

Pro Asp Phe Arg Pro Gly Thr Thr Ala Thr Leu Thr Ile Thr Asn Val
65                  70                  75                  80

Asp Ala Glu Asp Glu Ala Asp Tyr Tyr Cys His Ile Tyr Asp Ala Arg
                85                  90                  95

Gly Gly Thr Asn Trp Val Phe Asp Arg Gly Thr Thr Leu Thr Val Leu
            100                 105                 110

<210> SEQ ID NO 13
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Phe Arg Arg Ser Pro Gly Lys Gly Leu Glu Trp Ile
        35                  40                  45

Gly Tyr Val His Lys Ser Gly Asp Thr Asn Tyr Ser Pro Ser Leu Lys
 50                  55                  60

Ser Arg Val Asn Leu Ser Leu Asp Ala Ser Lys Asn Gln Val Ser Leu
65                  70                  75                  80

Ser Leu Val Ala Ala Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Asn Gly Thr Gln Val
        115                 120                 125

Thr Val Ser Ser
    130

<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

His Cys Thr Ala Ser Val Thr Ser Asp Ile Ser Val Ala Pro Gly Glu
1               5                   10                  15
```

```
Thr Ala Arg Ile Ser Cys Gly Glu Lys Ser Leu Gly Ser Arg Ala Val
                20                  25                  30

Gln Trp Tyr Gln His Arg Ala Gly Gln Ala Pro Ser Leu Ile Ile Tyr
            35                  40                  45

Asn Asn Gln Asp Arg Pro Ser Gly Ile Pro Glu Arg Phe Ser Gly Ser
 50                  55                  60

Pro Asp Ser Ala Phe Gly Thr Thr Ala Thr Leu Thr Ile Thr Ser Val
 65                  70                  75                  80

Glu Ala Gly Asp Glu Ala Asp Tyr Tyr Cys His Ile Trp Asp Ser Arg
                85                  90                  95

Val Pro Thr Lys Trp Val Phe Gly Gly Gly Thr Thr Leu Thr Val Leu
            100                 105                 110
```

<210> SEQ ID NO 15
<211> LENGTH: 132
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 15

```
Gln Val His Leu Gln Glu Ser Gly Pro Gly Leu Val Lys Pro Ser Glu
 1               5                  10                  15

Thr Leu Ser Leu Thr Cys Val Val Ser Gly Ala Ser Thr Ser Gly Gln
                20                  25                  30

Tyr Trp Ser Trp Ile Arg Gln Ser Pro Gly Lys Gly Leu Glu Trp Ile
            35                  40                  45

Gly Tyr Arg Ser Asp Ser Gly Asp Ala Asn Tyr Asn Pro Ser Leu Lys
 50                  55                  60

Ser Arg Val Ile Ile Ser Leu Asp Thr Ser Arg Asn Gln Leu Ser Leu
 65                  70                  75                  80

Asn Val Thr Ser Val Thr Thr Ala Asp Thr Ala Met Tyr Phe Cys Ala
                85                  90                  95

Arg Ala Gln Arg Gly Lys Arg Ile Tyr Gly Val Val Ser Leu Gly Glu
            100                 105                 110

Tyr Tyr His Tyr Tyr Ile Met Asp Val Trp Gly Thr Gly Thr Pro Val
            115                 120                 125

Thr Val Ser Ser
    130
```

<210> SEQ ID NO 16
<211> LENGTH: 132
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 16

```
Gln Val Gln Leu Gln Glu Ser Gly Pro Gly Leu Val Lys Pro Ser Glu
 1               5                  10                  15

Thr Leu Ser Val Thr Cys Ser Val Ser Gly Asp Ser Met Asn Asn Tyr
                20                  25                  30

Tyr Trp Thr Trp Ile Arg Gln Ser Pro Gly Lys Gly Leu Glu Trp Ile
            35                  40                  45

Gly Tyr Ile Ser Asp Arg Ala Ser Ala Thr Tyr Asn Pro Ser Leu Asn
 50                  55                  60
```

```
Ser Arg Val Val Ile Ser Arg Asp Thr Ser Lys Asn Gln Leu Ser Leu
 65                  70                  75                  80

Lys Leu Asn Ser Val Thr Pro Ala Asp Thr Ala Val Tyr Tyr Cys Ala
                 85                  90                  95

Thr Ala Arg Arg Gly Gln Arg Ile Tyr Gly Glu Val Ser Phe Gly Glu
            100                 105                 110

Phe Phe Tyr Tyr Tyr Ser Met Asp Val Trp Gly Lys Gly Thr Ala Val
        115                 120                 125

Thr Val Ser Ser
    130

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Asn Ile Trp Ser
1               5

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Val Ser Gly Glu Tyr Ile Glu Tyr Asn Pro Ser Leu Lys Ser
1               5                   10                  15

<210> SEQ ID NO 19
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Leu Arg Ala Arg Arg Ile Tyr Gly Val Ile Ala Phe Gly Glu Val
1               5                   10                  15

Tyr Asp Tyr His Tyr Phe Asp Val
            20

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Glu Lys Ser Asn Gly Ala Arg Ala Val Gln
1               5                   10

<210> SEQ ID NO 21
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 21

Asn Asn Gln Asp Arg Pro Ser
1               5

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

His Ile Trp Asp Ser Arg Phe Pro Leu Ser Trp Val
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asn Tyr Tyr Trp Thr
1               5

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Val Ser Asp Arg Ala Ser Ala Thr Tyr Asn Pro Ser Leu Lys Ser
1               5                   10                  15

<210> SEQ ID NO 25
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Arg Arg Gly Gln Arg Ile Tyr Gly Glu Val Ala Phe Gly Glu Phe
1               5                   10                  15

Phe Tyr Tyr Tyr Ser Met Asp Val
            20

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

```
Gly Arg Gln Ala Leu Gly Ser Arg Ala Val Gln
1               5                   10
```

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Asn Asn Gln Asp Arg Pro Ser
1               5
```

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
His Met Trp Asp Ser Arg Ser Gly Phe Ser Trp Ser
1               5                   10
```

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Gly Arg Gln Ala Leu Gly Ser Arg Ala Val Gln
1               5                   10
```

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Asn Asn Gln Asp Arg Pro Ser
1               5
```

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
His Met Trp Asp Ser Arg Ser Gly Phe Ser Trp Ser
1               5                   10
```

<210> SEQ ID NO 32
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 32

Gly Glu Glu Ser Leu Gly Ser Arg Ser Val Ile
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asn Asn Asn Asp Arg Pro Ser
1               5

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

His Ile Trp Asp Ser Arg Arg Pro Thr Asn Trp Val
1               5                   10

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Ala Tyr Trp Ser
1               5

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Val His His Ser Gly Asp Thr Asn Tyr Asn Pro Ser Leu Lys Arg
1               5                   10                  15

<210> SEQ ID NO 37
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Leu His Gly Lys Arg Ile Tyr Gly Thr Val Ala Leu Gly Glu Leu
1               5                   10                  15

Phe Val Tyr Phe Tyr Met Asp Val

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Glu Glu Ser Leu Gly Ser Arg Ser Val Ile
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asn Asn Asn Asp Arg Pro Ser
1               5

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

His Ile Trp Asp Ser Arg Arg Pro Thr Asn Trp Val
1               5                   10

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Asn Tyr Trp Ser
1               5

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Val His Asp Ser Gly Asp Thr Asn Tyr Asn Pro Ser Leu Lys Ser
1               5                   10                  15

Val

<210> SEQ ID NO 43
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Lys His Gly Arg Arg Ile Tyr Gly Val Val Ala Phe Lys Glu Trp
1               5                   10                  15

Phe Thr Tyr Phe Tyr Met Asp Val
            20

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Lys Glu Ser Ile Gly Ser Arg Ala Val Gln
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asn Asn Gln Asp Arg Pro Ala
1               5

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

His Ile Tyr Asp Ala Arg Gly Gly Thr Asn Trp Val
1               5                   10

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Asn Tyr Trp
1

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

```
Tyr Val His Asp Ser Gly Asp Thr Asn Tyr Asn Pro Ser Leu Lys Ser
1               5                   10                  15

<210> SEQ ID NO 49
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Lys His Gly Arg Arg Ile Tyr Gly Val Val Ala Phe Lys Glu Trp
1               5                   10                  15

Phe Thr Tyr Phe Tyr Met Asp Val
            20

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Lys Glu Ser Ile Gly Ser Arg Ala
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asn Asn Gln Asp Arg Pro Ala
1               5

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

His Ile Tyr Asp Ala Arg Gly Gly Thr Asn Trp Val
1               5                   10

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Ser Tyr Trp Ser
1               5

<210> SEQ ID NO 54
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Tyr Val His Lys Ser Gly Asp Thr Asn Tyr Ser Pro Ser Leu Lys Ser
1               5                   10                  15

<210> SEQ ID NO 55
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Leu His Gly Arg Arg Ile Tyr Gly Ile Val Ala Phe Asn Glu Trp
1               5                   10                  15

Phe Thr Tyr Phe Tyr Met Asp Val
            20

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Glu Lys Ser Leu Gly Ser Arg Ala Val Gln
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asn Asn Gln Asp Arg Pro Ser
1               5

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

His Ile Trp Asp Ser Arg Val Pro Thr Lys Trp Val
1               5                   10

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 59

Gly Gln Tyr Trp Ser
1               5

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Tyr Arg Ser Asp Ser Gly Asp Ala Asn Tyr Asn Pro Ser Leu Lys Ser
1               5                   10                  15

<210> SEQ ID NO 61
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Gln Arg Gly Lys Arg Ile Tyr Gly Val Val Ser Leu Gly Glu Tyr
1               5                   10                  15

Tyr His Tyr Tyr Ile Met Asp Val
            20

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asn Tyr Tyr Trp Thr
1               5

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Tyr Ile Ser Asp Arg Ala Ser Ala Thr Tyr Asn Pro Ser Leu Asn Ser
1               5                   10                  15

<210> SEQ ID NO 64
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Arg Arg Gly Gln Arg Ile Tyr Gly Glu Val Ser Phe Gly Glu Phe
1               5                   10                  15

Phe Tyr Tyr Tyr Ser Met Asp Val
```

<210> SEQ ID NO 65
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (1)..(4)
<223> OTHER INFORMATION: Any amino acid

<400> SEQUENCE: 65

Xaa Xaa Xaa Xaa Ser Tyr Val Arg Pro Leu Ser Val Ala Leu Gly Glu
1               5                   10                  15

Thr Ala Ser Ile Ser Cys Gly Arg Gln Ala Leu Gly Ser Arg Ala Val
            20                  25                  30

Gln Trp Tyr Gln His Arg Pro Gly Gln Ala Pro Ile Leu Leu Ile Tyr
        35                  40                  45

Asn Asn Gln Asp Arg Pro Ser Gly Ile Pro Glu Arg Phe Ser Gly Thr
    50                  55                  60

Pro Asp Ile Asn Phe Gly Thr Arg Ala Thr Leu Thr Ile Ser Gly Val
65                  70                  75                  80

Glu Ala Gly Asp Glu Ala Asp Tyr Tyr Cys His Met Trp Asp Ser Arg
                85                  90                  95

Ser Gly Phe Ser Trp Ser Phe Gly Gly Ala Thr Arg Leu Thr Val Leu
            100                 105                 110

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 66

Gly Arg Gln Ala Leu Gly Ser Arg Ala Val Gln
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 67

Asn Asn Gln Asp Arg Pro Ser
1               5

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 68

His Met Trp Asp Ser Arg Ser Gly Phe Ser Trp Ser
1               5                   10

<210> SEQ ID NO 69
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Thr Gln Gln Gly Lys Arg Ile Tyr Gly Val Val Ser Phe Gly Asp
            100                 105                 110

Tyr Tyr Tyr Tyr Tyr Tyr Met Asp Val Trp Gly Lys Gly Thr Thr Val
        115                 120                 125

Thr Val Ser Ser
    130

<210> SEQ ID NO 70
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Trp Val Phe Gly Gly Gly Thr Lys Leu Thr Val Leu
            100                 105

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 71

Gly Gly Gly Gly Ser
1               5

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Gly Gly Ser
1

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Gly Gly Gly Ser Gly Gly Gly Gly Ser Gly Gly Gly Gly Ser
1               5                   10                  15

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Ser Thr Ser Gly Ser Gly Lys Pro Gly Ser Gly Glu Gly Ser Thr
1               5                   10                  15

Lys Gly

<210> SEQ ID NO 75
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Cys Ala Arg Ala Gln His Gly Lys Arg Ile Tyr Gly Val Val Ser Phe
1               5                   10                  15

Gly Glu Phe Phe Tyr Tyr Tyr Tyr Met Asp Val Trp
            20                  25

<210> SEQ ID NO 76
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Any amino acid
```

```
<220> FEATURE:
<221> NAME/KEY: MOD_RES
<222> LOCATION: (29)..(30)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (66)..(67)
<223> OTHER INFORMATION: Any amino acid
<220> FEATURE:
<221> NAME/KEY: MOD_RES
<222> LOCATION: (81)..(82)
<223> OTHER INFORMATION: Any amino acid
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (97)..(97)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (111)..(111)
<223> OTHER INFORMATION: Any amino acid

<400> SEQUENCE: 76

Gln Val Gln Leu Gln Glu Ser Gly Pro Gly Leu Val Lys Pro Ser Glu
1               5                   10                  15

Thr Leu Ser Leu Thr Cys Ser Val Ser Gly Xaa Ser Xaa Xaa Asp Xaa
            20                  25                  30

Tyr Trp Ser Trp Ile Arg Gln Ser Pro Gly Lys Gly Leu Glu Trp Ile
        35                  40                  45

Gly Tyr Val His Asp Ser Gly Asp Thr Asn Tyr Asn Pro Ser Leu Lys
    50                  55                  60

Ser Xaa Xaa Ser Leu Asp Thr Ser Lys Asn Gln Val Ser Leu Lys Leu
65                  70                  75                  80

Xaa Xaa Val Thr Ala Ala Asp Ser Ala Xaa Tyr Tyr Cys Ala Arg Ala
                85                  90                  95

Xaa His Gly Xaa Arg Ile Tyr Gly Ile Val Ala Phe Gly Glu Xaa Phe
            100                 105                 110

Thr Tyr Phe Tyr Met Asp Val Trp Gly Lys Gly Thr Thr Val Thr Val
        115                 120                 125

Ser Ser
    130

<210> SEQ ID NO 77
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Gln Glu Ser Gly Pro Gly Leu Val Lys Pro Leu Glu
1               5                   10                  15

Thr Leu Ser Leu Thr Cys Asn Val Ser Gly Ala Phe Ile Ala Asp His
            20                  25                  30
```

```
Tyr Trp Ser Trp Ile Arg Leu Pro Leu Gly Lys Gly Pro Glu Trp Ile
            35                  40                  45

Gly Tyr Val His Asp Ser Gly Asp Ile Asn Tyr Asn Pro Ser Leu Lys
 50                  55                  60

Asn Arg Val His Leu Ser Leu Asp Lys Ser Thr Asn Gln Val Ser Leu
 65                  70                  75                  80

Lys Leu Met Ala Val Thr Ala Gly Asp Ser Ala Leu Tyr Tyr Cys Ala
                 85                  90                  95

Thr Thr Lys His Gly Arg Arg Ile Tyr Gly Val Val Ala Phe Gly Glu
                100                 105                 110

Trp Phe Thr Tyr Phe Tyr Met Asp Val Trp Gly Arg Gly Thr Thr Val
            115                 120                 125

Thr Val Ser Ser
        130

<210> SEQ ID NO 78
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Val His Leu Gln Glu Ser Gly Pro Gly Leu Val Lys Pro Ser Glu
 1               5                  10                  15

Thr Leu Ser Leu Thr Cys Asn Val Ser Gly Thr Leu Val Arg Asp Asn
             20                  25                  30

Tyr Trp Ser Trp Met Arg Gln Pro Leu Gly Lys Gln Pro Glu Trp Ile
            35                  40                  45

Gly Tyr Val His Asp Ser Gly Asp Thr Asn Tyr Asn Pro Ser Leu Lys
 50                  55                  60

Ser Arg Val His Leu Ser Leu Asp Lys Ser Asn Asn Leu Val Ser Leu
 65                  70                  75                  80

Arg Leu Thr Ala Val Thr Ala Ala Asp Ser Ala Thr Tyr Tyr Cys Ala
                 85                  90                  95

Thr Thr Lys His Gly Arg Arg Ile Tyr Gly Ile Val Ala Phe Asn Glu
                100                 105                 110

Trp Phe Thr Tyr Phe Tyr Met Asp Val Trp Gly Lys Gly Thr Thr Val
            115                 120                 125

Thr Val Ser Ser
        130

<210> SEQ ID NO 79
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Gln Glu Ser Gly Pro Gly Leu Val Lys Pro Ser Glu
 1               5                  10                  15

Thr Leu Ser Leu Thr Cys Ser Val Ser Gly Ala Ser Ile Ser Asp Ser
             20                  25                  30

Tyr Trp Ser Trp Ile Arg Arg Ser Pro Gly Lys Gly Leu Glu Trp Ile
            35                  40                  45
```

-continued

Gly Tyr Val His Lys Ser Gly Asp Thr Asn Tyr Ser Pro Ser Leu Lys
    50                  55                  60

Ser Arg Val Asn Leu Ser Leu Asp Thr Ser Lys Asn Gln Val Ser Leu
65                  70                  75                  80

Ser Leu Val Ala Ala Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Asn Gly Thr Gln Val
        115                 120                 125

Thr Val Ser Ser
    130

<210> SEQ ID NO 80
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Val Gln Leu Gln Glu Ser Gly Pro Gly Leu Val Lys Pro Pro Glu
1               5                   10                  15

Thr Leu Ser Leu Thr Cys Ser Val Ser Gly Ala Ser Val Asn Asp Ala
            20                  25                  30

Tyr Trp Ser Trp Ile Arg Gln Ser Pro Gly Lys Arg Pro Glu Trp Val
        35                  40                  45

Gly Tyr Val His His Ser Gly Asp Thr Asn Tyr Asn Pro Ser Leu Lys
    50                  55                  60

Arg Arg Val Thr Phe Ser Leu Asp Thr Ala Lys Asn Glu Val Ser Leu
65                  70                  75                  80

Lys Leu Val Ala Leu Thr Ala Ala Asp Ser Ala Val Tyr Phe Cys Ala
                85                  90                  95

Arg Ala Leu His Gly Lys Arg Ile Tyr Gly Ile Val Ala Leu Gly Glu
            100                 105                 110

Leu Phe Thr Tyr Phe Tyr Met Asp Val Trp Gly Lys Gly Thr Thr Val
        115                 120                 125

Thr Val Ser Ser
    130

<210> SEQ ID NO 81
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Gln Glu Ser Gly Pro Gly Leu Val Lys Pro Pro Glu
1               5                   10                  15

Thr Leu Ser Leu Thr Cys Ser Val Ser Gly Ala Ser Ile Asn Asp Ala
            20                  25                  30

Tyr Trp Ser Trp Ile Arg Gln Ser Pro Gly Lys Arg Pro Glu Trp Val
        35                  40                  45

Gly Tyr Val His His Ser Gly Asp Thr Asn Tyr Asn Pro Ser Leu Lys
    50                  55                  60

-continued

```
Arg Arg Val Thr Phe Ser Leu Asp Thr Ala Lys Asn Glu Val Ser Leu
 65                  70                  75                  80

Lys Leu Val Asp Leu Thr Ala Ala Asp Ser Ala Val Tyr Phe Cys Ala
                 85                  90                  95

Arg Ala Leu His Gly Lys Arg Ile Tyr Gly Ile Val Ala Leu Gly Glu
            100                 105                 110

Leu Phe Thr Tyr Phe Tyr Met Asp Val Trp Gly Lys Gly Thr Thr Val
        115                 120                 125

Thr Val Ser Ser
    130
```

<210> SEQ ID NO 82
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Gln Val Gln Leu Gln Glu Ser Gly Pro Gly Leu Val Lys Pro Pro Glu
 1               5                  10                  15

Thr Leu Ser Leu Thr Cys Ser Val Ser Gly Ala Ser Ile Asn Asp Ala
             20                  25                  30

Tyr Trp Ser Trp Ile Arg Gln Ser Pro Gly Lys Arg Pro Glu Trp Val
         35                  40                  45

Gly Tyr Val His His Ser Gly Asp Thr Asn Tyr Asn Pro Ser Leu Lys
     50                  55                  60

Arg Arg Val Ser Phe Ser Leu Asp Thr Ala Lys Asn Glu Val Ser Leu
 65                  70                  75                  80

Lys Leu Val Asp Leu Thr Ala Ala Asp Ser Ala Ile Tyr Phe Cys Ala
                 85                  90                  95

Arg Ala Leu His Gly Lys Arg Ile Tyr Gly Ile Val Ala Leu Gly Glu
            100                 105                 110

Leu Phe Thr Tyr Phe Tyr Met Asp Val Trp Gly Lys Gly Thr Thr Val
        115                 120                 125

Thr Val Ser Ser
    130
```

<210> SEQ ID NO 83
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

```
Gln Val Gln Leu Val Glu Ser Gly Pro Gly Leu Val Thr Pro Ser Glu
 1               5                  10                  15

Thr Leu Ser Leu Thr Cys Thr Val Ser Asn Gly Ser Val Ser Gly Arg
             20                  25                  30

Phe Trp Ser Trp Ile Arg Gln Ser Pro Gly Arg Gly Leu Glu Trp Ile
         35                  40                  45

Gly Tyr Phe Ser Asp Thr Asp Arg Ser Glu Tyr Ser Pro Ser Leu Arg
     50                  55                  60

Ser Arg Leu Thr Leu Ser Leu Asp Ala Ser Arg Asn Gln Leu Ser Leu
 65                  70                  75                  80
```

```
Lys Leu Lys Ser Val Thr Ala Ala Asp Ser Ala Thr Tyr Tyr Cys Ala
                85                  90                  95

Arg Ala Gln Gln Gly Lys Arg Ile Tyr Gly Ile Val Ser Phe Gly Glu
            100                 105                 110

Phe Phe Tyr Tyr Tyr Tyr Met Asp Ala Trp Gly Lys Gly Thr Ala Val
        115                 120                 125

Thr Val Ser Ser
    130

<210> SEQ ID NO 84
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Gln Glu Ser Gly Pro Gly Leu Val Lys Pro Ser Glu
1               5                   10                  15

Thr Leu Ser Leu Thr Cys Ser Val Ser Asn Gly Ser Val Ser Gly Arg
            20                  25                  30

Phe Trp Ser Trp Ile Arg Gln Ser Pro Gly Arg Gly Leu Glu Trp Ile
        35                  40                  45

Gly Tyr Phe Ser Asp Thr Glu Lys Ser Asn Tyr Asn Pro Ser Leu Arg
    50                  55                  60

Ser Arg Leu Thr Leu Ser Val Asp Ala Ser Lys Asn Gln Leu Ser Leu
65                  70                  75                  80

Lys Leu Asn Ser Val Thr Ala Ala Asp Ser Ala Thr Tyr Tyr Cys Ala
                85                  90                  95

Arg Thr Gln Gln Gly Lys Arg Ile Tyr Gly Val Val Ser Phe Gly Glu
            100                 105                 110

Phe Phe His Tyr Tyr Tyr Met Asp Ala Trp Gly Lys Gly Thr Ala Val
        115                 120                 125

Thr Val Ser Ser
    130

<210> SEQ ID NO 85
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Val Gln Leu Gln Glu Ser Gly Pro Gly Leu Val Lys Pro Ser Glu
1               5                   10                  15

Thr Leu Ser Val Thr Cys Ser Val Ser Gly Asp Ser Met Asn Asn Tyr
            20                  25                  30

Tyr Trp Thr Trp Ile Arg Gln Ser Pro Gly Lys Gly Leu Glu Trp Ile
        35                  40                  45

Gly Tyr Ile Ser Asp Arg Glu Ser Ala Thr Tyr Asn Pro Ser Leu Asn
    50                  55                  60

Ser Arg Val Val Ile Ser Arg Asp Thr Ser Thr Asn Gln Leu Ser Leu
65                  70                  75                  80

Lys Leu Asn Ser Val Thr Pro Ala Asp Thr Ala Val Tyr Tyr Cys Ala
                85                  90                  95
```

```
Thr Ala Arg Arg Gly Gln Arg Ile Tyr Gly Val Val Ser Phe Gly Glu
            100                 105                 110

Phe Phe Tyr Tyr Tyr Ser Met Asp Val Trp Gly Arg Gly Thr Thr Val
        115                 120                 125

Thr Val Ser Ser
    130

<210> SEQ ID NO 86
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Val Gln Leu Gln Glu Ser Gly Pro Gly Leu Val Lys Pro Ser Glu
1               5                   10                  15

Thr Leu Ser Val Thr Cys Ser Val Ser Gly Asp Ser Met Asn Asn Tyr
            20                  25                  30

Tyr Trp Thr Trp Ile Arg Gln Ser Pro Gly Lys Gly Leu Glu Trp Ile
        35                  40                  45

Gly Tyr Ile Ser Asp Arg Ala Ser Ala Thr Tyr Asn Pro Ser Leu Asn
    50                  55                  60

Ser Arg Val Val Ile Ser Arg Asp Thr Ser Lys Asn Gln Leu Ser Leu
65                  70                  75                  80

Lys Leu Asn Ser Val Thr Pro Ala Asp Thr Ala Val Tyr Tyr Cys Ala
                85                  90                  95

Thr Ala Arg Arg Gly Gln Arg Ile Tyr Gly Val Val Ser Phe Gly Glu
            100                 105                 110

Phe Phe Tyr Tyr Tyr Ser Met Asp Val Trp Gly Lys Gly Thr Thr Val
        115                 120                 125

Thr Val Ser Ser
    130

<210> SEQ ID NO 87
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Val Gln Leu Gln Glu Ser Gly Pro Gly Leu Val Lys Pro Ser Glu
1               5                   10                  15

Thr Leu Ser Val Thr Cys Ser Val Ser Gly Asp Ser Met Asn Asn Tyr
            20                  25                  30

Tyr Trp Thr Trp Ile Arg Gln Ser Pro Gly Lys Gly Leu Glu Trp Ile
        35                  40                  45

Gly Tyr Ile Ser Asp Arg Glu Ser Ala Thr Tyr Asn Pro Ser Leu Asn
    50                  55                  60

Ser Arg Val Val Ile Ser Arg Asp Thr Ser Lys Asn Gln Leu Ser Leu
65                  70                  75                  80

Lys Leu Asn Ser Val Thr Pro Ala Asp Thr Ala Val Tyr Tyr Cys Ala
                85                  90                  95

Thr Ala Arg Arg Gly Gln Arg Ile Tyr Gly Val Val Ser Phe Gly Glu
            100                 105                 110
```

```
Phe Phe Tyr Tyr Tyr Ser Met Asp Val Trp Gly Lys Gly Thr Thr Val
        115                 120                 125

Thr Val Ser Ser
    130

<210> SEQ ID NO 88
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Gln Glu Ser Gly Pro Gly Leu Val Lys Pro Ser Glu
1               5                   10                  15

Thr Leu Ser Val Thr Cys Ser Val Ser Gly Asp Ser Met Asn Asn Ser
            20                  25                  30

Tyr Trp Thr Trp Ile Arg Gln Ser Pro Gly Lys Gly Leu Glu Trp Ile
        35                  40                  45

Gly Tyr Ile Ser Lys Ser Glu Ser Ala Asn Tyr Asn Pro Ser Leu Asn
    50                  55                  60

Ser Arg Val Val Ile Ser Arg Asp Thr Ser Lys Asn Gln Leu Ser Leu
65                  70                  75                  80

Lys Leu Asn Ser Val Thr Pro Ala Asp Thr Ala Val Tyr Tyr Cys Ala
                85                  90                  95

Thr Ala Arg His Gly Gln Arg Ile Tyr Gly Val Val Ser Phe Gly Glu
            100                 105                 110

Phe Phe Thr Tyr Tyr Ser Met Asp Val Trp Gly Lys Gly Thr Thr Val
        115                 120                 125

Thr Val Ser Ser
    130

<210> SEQ ID NO 89
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (67)..(68)
<223> OTHER INFORMATION: Any amino acid
<220> FEATURE:
<221> NAME/KEY: MOD_RES
<222> LOCATION: (79)..(79)
<223> OTHER INFORMATION: Any amino acid
<220> FEATURE:
<221> NAME/KEY: MOD_RES
<222> LOCATION: (97)..(97)
<223> OTHER INFORMATION: Any amino acid
<220> FEATURE:
<221> NAME/KEY: MOD_RES
<222> LOCATION: (100)..(100)
```

<223> OTHER INFORMATION: Any amino acid

<400> SEQUENCE: 89

Ser Xaa Val Arg Pro Gln Pro Ser Leu Ser Val Ala Pro Gly Glu
1               5                   10                  15

Thr Ala Arg Ile Xaa Cys Gly Glu Xaa Ser Leu Gly Ser Arg Ala Val
            20                  25                  30

Gln Trp Tyr Gln Gln Arg Pro Gly Gln Ala Pro Ser Leu Ile Ile Tyr
        35                  40                  45

Asn Asn Gln Asp Arg Pro Ser Gly Ile Pro Glu Arg Phe Ser Gly Ser
    50                  55                  60

Pro Asp Xaa Xaa Phe Gly Thr Thr Ala Thr Leu Thr Ile Thr Xaa Val
65              70                  75                  80

Glu Ala Gly Asp Glu Ala Asp Tyr Tyr Cys His Ile Trp Asp Ser Arg
                85                  90                  95

Xaa Pro Thr Xaa Trp Val Phe Gly Gly Gly Thr Thr Leu Thr Val Leu
            100                 105                 110

<210> SEQ ID NO 90
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Ser Ser Met Ser Val Ser Pro Gly Glu Thr Ala Lys Ile Thr Cys Gly
1               5                   10                  15

Glu Lys Ser Ile Gly Ser Arg Ala Val Gln Trp Tyr Gln Lys Lys Pro
            20                  25                  30

Gly Gln Pro Pro Ser Leu Ile Ile Tyr Asn Asn Gln Asp Arg Pro Ser
        35                  40                  45

Gly Val Pro Glu Arg Phe Ser Ala Ser Pro Asp Ile Glu Phe Gly Thr
    50                  55                  60

Thr Ala Thr Leu Thr Ile Thr Asn Val Glu Ala Gly Asp Glu Ala Asp
65              70                  75                  80

Tyr Tyr Cys His Ile Tyr Asp Ala Arg Arg Pro Thr Asn Trp Val Phe
                85                  90                  95

Asp Arg Gly Thr Thr Leu Thr Val Leu
            100                 105

<210> SEQ ID NO 91
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Ser Ser Met Ser Val Ser Pro Gly Glu Thr Ala Lys Ile Ser Cys Gly
1               5                   10                  15

Lys Glu Ser Ile Gly Ser Arg Ala Val Gln Trp Tyr Gln Gln Lys Ser
            20                  25                  30

Gly Gln Pro Pro Ser Leu Ile Ile Tyr Asn Asn Gln Asp Arg Pro Ser
        35                  40                  45

Gly Val Pro Glu Arg Phe Ser Ala Thr Pro Asp Phe Gly Ala Gly Thr
    50                  55                  60

Thr Ala Thr Leu Thr Ile Thr Asn Val Glu Ala Asp Asp Glu Ala Asp
65                  70                  75                  80

Tyr Tyr Cys His Ile Tyr Asp Ala Arg Gly Gly Thr Asn Trp Val Phe
                85                  90                  95

Asp Arg Gly Ala Thr Leu Thr Val Leu
            100                 105

<210> SEQ ID NO 92
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Asp Ser Pro Phe Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu
            100                 105

<210> SEQ ID NO 93
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Ser Phe Val Ser Val Ala Pro Gly Gln Thr Ala Arg Ile Thr Cys Gly
1               5                   10                  15

Glu Glu Ser Leu Gly Ser Arg Ser Val Ile Trp Tyr Gln Gln Arg Pro
            20                  25                  30

Gly Gln Ala Pro Ser Leu Ile Met Tyr Asn Asn His Asp Arg Pro Ser
        35                  40                  45

Gly Ile Pro Glu Arg Phe Ser Gly Ser Pro Gly Ser Thr Phe Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Arg Pro Thr Asn Trp Val Phe
                85                  90                  95

Gly Glu Gly Thr Thr Leu Thr Val Leu
            100                 105

<210> SEQ ID NO 94
<211> LENGTH: 105
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 94

Ser Phe Val Ser Val Ala Pro Gly Gln Thr Ala Arg Ile Thr Cys Gly
1               5                   10                  15

Glu Glu Ser Leu Gly Ser Arg Ser Val Ile Trp Tyr Gln Gln Arg Pro
            20                  25                  30

Gly Gln Ala Pro Ser Leu Ile Ile Tyr Asn Asn Asn Asp Arg Pro Ser
        35                  40                  45

Gly Ile Pro Glu Arg Phe Ser Gly Ser Pro Gly Ser Thr Phe Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Arg Pro Thr Asn Trp Val Phe
                85                  90                  95

Gly Glu Gly Thr Thr Leu Thr Val Leu
            100                 105

<210> SEQ ID NO 95
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ser Tyr Val Arg Pro Leu Ser Val Ala Leu Gly Glu Thr Ala Ser Ile
1               5                   10                  15

Ser Cys Gly Arg Gln Ala Leu Gly Ser Arg Ala Val Gln Trp Tyr Gln
            20                  25                  30

His Arg Pro Gly Gln Ala Pro Ile Leu Leu Ile Tyr Asn Asn Gln Asp
        35                  40                  45

Arg Pro Ser Gly Ile Pro Glu Arg Phe Ser Gly Thr Pro Asp Ile Asn
    50                  55                  60

Phe Gly Thr Arg Ala Thr Leu Thr Ile Ser Gly Val Glu Ala Gly Asp
65                  70                  75                  80

Glu Ala Asp Tyr Tyr Cys His Met Trp Asp Ser Arg Ser Gly Phe Ser
                85                  90                  95

Trp Ser Phe Gly Gly Ala Thr Arg Leu Thr Val Leu
            100                 105

<210> SEQ ID NO 96
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ser Tyr Val Arg Pro Leu Ser Val Ala Leu Gly Glu Thr Ala Arg Ile
1               5                   10                  15

Ser Cys Gly Arg Gln Ala Leu Gly Ser Arg Ala Val Gln Trp Tyr Gln
            20                  25                  30

His Arg Pro Gly Gln Ala Pro Ile Leu Leu Ile Tyr Asn Asn Gln Asp
        35                  40                  45
```

```
Arg Pro Ser Gly Ile Pro Glu Arg Phe Ser Gly Thr Pro Asp Ile Asn
    50                  55                  60

Phe Gly Thr Arg Ala Thr Leu Thr Ile Ser Gly Val Glu Ala Gly Asp
65                  70                  75                  80

Glu Ala Asp Tyr Tyr Cys His Met Trp Asp Ser Arg Ser Gly Phe Ser
                85                  90                  95

Trp Ser Phe Gly Gly Ala Thr Arg Leu Thr Val Leu
                100                 105
```

```
<210> SEQ ID NO 97
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Ser Ser Leu Pro Leu Ser Val Ala Pro Gly Ala Thr Ala Lys Ile Ala
1               5                   10                  15

Cys Gly Glu Lys Ser Phe Ala Ser Arg Ala Val Gln Trp Tyr Gln Gln
                20                  25                  30

Lys Pro Gly Gln Ala Pro Val Leu Ile Ile Tyr Asn Asn Gln Asp Arg
            35                  40                  45

Pro Ala Gly Val Ser Glu Arg Phe Ser Gly Thr Pro Asp Val Gly Phe
    50                  55                  60

Gly Ser Thr Ala Thr Leu Thr Ile Ser Arg Val Glu Ala Gly Asp Glu
65                  70                  75                  80

Ala Asp Tyr Tyr Cys His Lys Trp Asp Ser Arg Ser Pro Leu Ser Trp
                85                  90                  95

Val Phe Gly Gly Gly Thr Gln Leu Thr Val Leu
                100                 105
```

```
<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Ser Ser Leu Pro Leu Ser Leu Ala Pro Gly Ala Thr Ala Lys Ile Pro
1               5                   10                  15

Cys Gly Glu Lys Ser Arg Gly Ser Arg Ala Val Gln Trp Tyr Gln Gln
                20                  25                  30

Lys Pro Gly Gln Ala Pro Thr Leu Ile Ile Tyr Asn Asn Gln Asp Arg
            35                  40                  45

Pro Ala Gly Val Ser Glu Arg Tyr Ser Gly Asn Pro Asp Val Ala Ile
    50                  55                  60

Gly Val Thr Ala Thr Leu Thr Ile Ser Arg Val Glu Ala Gly Asp Glu
65                  70                  75                  80

Ala Glu Tyr Tyr Cys His Tyr Trp Asp Ser Arg Ser Pro Ile Ser Trp
                85                  90                  95

Val Phe Gly Gly Trp Thr Gln Leu Thr Val Leu
                100                 105
```

```
<210> SEQ ID NO 99
<211> LENGTH: 6
```

<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 99

His His His His His His
1               5

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tacattgata gtcattcgtg                                                20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tcattttata cttcgttatt                                                20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gaattacgct accaatgggc                                                20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
attattaaaa gactgctcaa                                                20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
aatctctctt gaatcaggtg                                                20

<210> SEQ ID NO 105
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tagttttcga aagagtgaca                                                    20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
aacgtcctgt aaacgcgtcc                                                    20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
cggcacttca ttgtggttca                                                    20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
ccacagccaa ccagggttca                                                    20

<210> SEQ ID NO 109
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Cys Ala Thr Thr Lys His Gly Arg Arg Ile Tyr Gly Val Val Ala Phe
1               5                  10                  15

Arg Glu Trp Phe Thr Tyr Phe Tyr Met Asp Val Trp
            20                  25

<210> SEQ ID NO 110
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Cys Ala Thr Thr Lys His Gly Arg Arg Ile Tyr Gly Val Val Ala Phe
1               5                  10                  15
```

```
Lys Glu Trp Phe Thr Tyr Phe Tyr Met Asp Val Trp
            20                  25
```

<210> SEQ ID NO 111
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

```
Cys Ala Arg Thr Gln His Gly Arg Arg Ile Tyr Gly Ile Val Ala Phe
1               5                   10                  15

Arg Glu Trp Phe Thr Tyr Phe Tyr Met Asp Val Trp
            20                  25
```

<210> SEQ ID NO 112
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

```
Cys Ala Arg Thr Leu His Gly Arg Arg Ile Tyr Gly Ile Val Ala Phe
1               5                   10                  15

Asn Glu Trp Phe Thr Tyr Phe Tyr Met Asp Val Trp
            20                  25
```

<210> SEQ ID NO 113
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

```
Cys Ala Thr Thr Lys His Ser Arg Arg Ile Tyr Gly Ile Val Ala Phe
1               5                   10                  15

Asn Glu Trp Phe Thr Tyr Phe Tyr Met Asp Ile Trp
            20                  25
```

<210> SEQ ID NO 114
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

```
Cys Ala Thr Thr Lys His Gly Arg Arg Ile Tyr Gly Glu Val Ala Tyr
1               5                   10                  15

Gly Glu Met Phe Thr Tyr Phe Tyr Met Asp Leu Trp
            20                  25
```

<210> SEQ ID NO 115
<211> LENGTH: 28
<212> TYPE: PRT
<213> ORGANISM: Artificial Sequence
<220> FEATURE:
<223> OTHER INFORMATION: Description of Artificial Sequence: Synthetic

```
                      peptide

<400> SEQUENCE: 115

Cys Ala Arg Ala Leu His Gly Lys Arg Ile Tyr Gly Ile Val Ala Leu
1               5                   10                  15

Gly Glu Leu Phe Thr Tyr Phe Tyr Met Asp Val Trp
            20                  25

<210> SEQ ID NO 116
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Cys Ala Thr Ala Arg Arg Gly Gln Arg Ile Tyr Gly Val Val Ser Phe
1               5                   10                  15

Gly Glu Phe Phe Tyr Tyr Tyr Tyr Met Asp Val Trp
            20                  25

<210> SEQ ID NO 117
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Cys Ala Thr Ala Arg Arg Gly Gln Arg Ile Tyr Gly Val Val Ser Phe
1               5                   10                  15

Gly Glu Phe Phe Tyr Tyr Tyr Ser Met Asp Val Trp
            20                  25

<210> SEQ ID NO 118
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Cys Ala Arg Ala Gln Gln Gly Lys Arg Ile Tyr Gly Met Val Ser Phe
1               5                   10                  15

Gly Glu Phe Phe Tyr Tyr Tyr Tyr Met Asp Val Trp
            20                  25

<210> SEQ ID NO 119
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Cys Ala Arg Ala Gln Gln Gly Lys Arg Ile Tyr Gly Met Val Ser Phe
1               5                   10                  15

Gly Glu Leu Phe Tyr Tyr Tyr Tyr Met Asp Val Trp
            20                  25
```

```
<210> SEQ ID NO 120
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Cys Ala Arg Ala Gln Gln Gly Lys Arg Ile Tyr Gly Ile Val Ser Phe
1               5                  10                  15

Gly Glu Leu Phe Tyr Tyr Tyr Tyr Met Asp Ala Trp
            20                  25

<210> SEQ ID NO 121
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Cys Ala Arg Ala Gln Gln Gly Lys Arg Ile Tyr Gly Ile Val Ser Phe
1               5                  10                  15

Gly Glu Phe Phe Tyr Tyr Tyr Tyr Met Asp Ala Trp
            20                  25

<210> SEQ ID NO 122
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Cys Ala Arg Ala Gln Arg Gly Lys Arg Ile Tyr Gly Val Val Ser Leu
1               5                  10                  15

Gly Glu Tyr Tyr Tyr Tyr Tyr Ile Met Asp Val Trp
            20                  25

<210> SEQ ID NO 123
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Cys Ala Arg Ala Gln Arg Gly Lys Arg Ile Tyr Gly Val Val Ser Leu
1               5                  10                  15

Gly Glu Tyr Tyr His Tyr Tyr Ile Met Asp Val Trp
            20                  25

<210> SEQ ID NO 124
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 124

Cys Ala Arg Ala Gln Arg Ala Gln Arg Ile Tyr Gly Thr Ile Ser Leu
1               5                   10                  15

Gly Asn Phe Phe Asp Tyr Leu Tyr Met Asp Val Trp
            20                  25
```